(12) United States Patent
Hulford et al.

(10) Patent No.: US 11,751,966 B2
(45) Date of Patent: Sep. 12, 2023

(54) MEDICAL DEVICE HANDLE

(71) Applicant: Intuitive Surgical Operations, Inc., Sunnyvale, CA (US)

(72) Inventors: Timothy B. Hulford, San Jose, CA (US); Russell L. E. Blanchard, San Jose, CA (US); Roman Lapaev, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 783 days.

(21) Appl. No.: 16/634,489

(22) PCT Filed: Jul. 25, 2018

(86) PCT No.: PCT/US2018/043772
§ 371 (c)(1),
(2) Date: Jan. 27, 2020

(87) PCT Pub. No.: WO2019/023390
PCT Pub. Date: Jan. 31, 2019

(65) Prior Publication Data
US 2020/0253678 A1    Aug. 13, 2020

Related U.S. Application Data

(60) Provisional application No. 62/537,884, filed on Jul. 27, 2017.

(51) Int. Cl.
*A61B 34/00*    (2016.01)
*A61B 34/35*    (2016.01)
(Continued)

(52) U.S. Cl.
CPC .............. *A61B 34/74* (2016.02); *A61B 34/25* (2016.02); *A61B 34/35* (2016.02); *A61B 34/37* (2016.02);
(Continued)

(58) Field of Classification Search
None
See application file for complete search history.

(56) References Cited

U.S. PATENT DOCUMENTS 6,102,850 A * 8/2000 Wang .................... B25J 9/1689
600/102
6,325,808 B1 * 12/2001 Bernard ................ A61B 34/30
606/139
(Continued)

FOREIGN PATENT DOCUMENTS

CN    101999938 A    4/2011
CN    103536364 A    1/2014
(Continued)

OTHER PUBLICATIONS

Festo, "BionicCobot: Sensitive helper for human-robot collaboration," Product Brochure, Mar. 27, 2017, retreived from the internet< url: https://www.youtube.com/watch?v=54u3H69tcgM, 6 pages</url:>.

(Continued)

*Primary Examiner* — Carl H Layno
*Assistant Examiner* — Manolis Pahakis
(74) *Attorney, Agent, or Firm* — SCHWEGMAN LUNDBERG & WOESSNER, P.A.

(57) ABSTRACT

An example medical device configured for use with a teleoperated surgical system may include a control system, a movable manipulator arm, and a handle coupled to the manipulator arm, wherein in a first pose of the movable manipulator arm, the handle is oriented at a first convenient hold angle to a clinical user, wherein in a second pose of the movable manipulator arm different from the first pose, the handle is oriented at a second convenient hold angle to the clinical user, different from the first convenient hold angle, and wherein the control system includes programmed instructions to automatically move the handle from the first (Continued)

orientation to the second orientation as the movable manipulator arm moves from the first pose to the second pose.

22 Claims, 46 Drawing Sheets

(51) Int. Cl.
  *A61B 34/37* (2016.01)
  *A61B 90/30* (2016.01)
  *B25J 9/16* (2006.01)
(52) U.S. Cl.
  CPC ........ *A61B 90/30* (2016.02); *A61B 2034/252* (2016.02); *A61B 2034/254* (2016.02); *A61B 2034/258* (2016.02); *A61B 2034/742* (2016.02); *B25J 9/1676* (2013.01)

(56) References Cited

U.S. PATENT DOCUMENTS

| | | | |
|---|---|---|---|
| 6,424,885 B1* | 7/2002 | Niemeyer | A61B 34/35 600/109 |
| 6,434,416 B1* | 8/2002 | Mizoguchi | A61B 34/20 359/372 |
| 6,985,133 B1* | 1/2006 | Rodomista | G06F 3/016 345/161 |
| 7,747,311 B2* | 6/2010 | Quaid, III | A61B 34/74 345/157 |
| 7,831,292 B2* | 11/2010 | Quaid | A61B 34/37 345/157 |
| 8,100,133 B2 | 1/2012 | Mintz et al. | |
| 8,287,522 B2* | 10/2012 | Moses | A61B 34/76 606/1 |
| 8,343,096 B2* | 1/2013 | Kirschenman | A61B 34/76 604/95.04 |
| 9,375,841 B1 | 6/2016 | Kemper et al. | |
| 9,375,853 B1 | 6/2016 | Edsinger | |
| 9,764,474 B2 | 9/2017 | Yamamoto et al. | |
| 10,011,018 B2* | 7/2018 | McGrogan | A61B 34/70 |
| 10,064,684 B2 | 9/2018 | Nakamura et al. | |
| 10,192,195 B1 | 1/2019 | Brazeau | |
| 10,258,419 B2* | 4/2019 | Auld | A61B 34/30 |
| 10,299,868 B2* | 5/2019 | Tsuboi | B25J 9/1674 |
| 10,426,321 B2* | 10/2019 | Sholev | A61B 1/00149 |
| 10,434,666 B2 | 10/2019 | Katayama | |
| 10,569,431 B2 | 2/2020 | Katayama | |
| 2003/0220564 A1* | 11/2003 | Wilkins | F16M 11/046 600/437 |
| 2004/0034282 A1 | 2/2004 | Quaid, III | |
| 2004/0106916 A1* | 6/2004 | Quaid | A61B 34/71 606/1 |
| 2004/0115606 A1* | 6/2004 | Davies | A63B 69/0057 434/258 |
| 2005/0094159 A1 | 5/2005 | Su | |
| 2006/0142657 A1* | 6/2006 | Quaid | A61B 90/37 600/424 |
| 2009/0247993 A1* | 10/2009 | Kirschenman | A61B 34/71 606/1 |
| 2009/0259412 A1* | 10/2009 | Brogardh | G05B 19/423 702/41 |
| 2010/0166496 A1* | 7/2010 | Bennett | A61B 34/30 403/122 |
| 2010/0225209 A1* | 9/2010 | Goldberg | G16H 20/40 312/209 |
| 2010/0228265 A1* | 9/2010 | Prisco | B25J 9/1689 606/130 |
| 2011/0071543 A1 | 3/2011 | Prisco et al. | |
| 2011/0071676 A1 | 3/2011 | Sanders et al. | |
| 2011/0162476 A1* | 7/2011 | Nakamura | A61B 90/50 901/19 |
| 2013/0053866 A1 | 2/2013 | Leung et al. | |
| 2013/0131867 A1* | 5/2013 | Olds | A61B 90/00 700/260 |
| 2013/0172903 A1* | 7/2013 | Suarez | A61B 17/142 606/1 |
| 2013/0221183 A1 | 8/2013 | Volkenand et al. | |
| 2013/0253485 A1 | 9/2013 | Fehre et al. | |
| 2014/0018821 A1 | 1/2014 | Yeung et al. | |
| 2014/0107665 A1* | 4/2014 | Shellenberger | A61B 34/70 606/130 |
| 2014/0121834 A1* | 5/2014 | Ogawa | A61B 34/30 700/257 |
| 2014/0135793 A1* | 5/2014 | Cooper | A61B 34/30 901/31 |
| 2014/0314538 A1* | 10/2014 | Carter | A61B 90/50 414/744.3 |
| 2015/0066050 A1* | 3/2015 | Jardine | A61B 34/37 606/130 |
| 2015/0073340 A1 | 3/2015 | Pacheco et al. | |
| 2015/0100066 A1* | 4/2015 | Kostrzewski | A61B 34/30 606/130 |
| 2015/0148948 A1 | 5/2015 | Singh et al. | |
| 2015/0223897 A1* | 8/2015 | Kostrzewski | A61B 46/10 606/1 |
| 2016/0081753 A1 | 3/2016 | Kostrzewski | |
| 2016/0157943 A1 | 6/2016 | Mintz et al. | |
| 2017/0000575 A1 | 1/2017 | Griffiths et al. | |
| 2017/0006689 A1 | 1/2017 | Andre et al. | |
| 2017/0007335 A1 | 1/2017 | Popovic et al. | |
| 2017/0020615 A1 | 1/2017 | Koenig et al. | |
| 2017/0086928 A1* | 3/2017 | Auld | A61B 90/50 |
| 2017/0087731 A1 | 3/2017 | Wagner et al. | |
| 2017/0135776 A1 | 5/2017 | Cohen et al. | |
| 2017/0165014 A1* | 6/2017 | Nakanishi | A61B 34/74 |
| 2017/0172674 A1 | 6/2017 | Hanuschik et al. | |
| 2017/0181801 A1 | 6/2017 | Griffiths et al. | |
| 2017/0209226 A1 | 7/2017 | Overmyer et al. | |
| 2017/0258528 A1 | 9/2017 | Bai et al. | |
| 2017/0319283 A1* | 11/2017 | Suresh | A61B 34/25 |
| 2017/0333139 A1* | 11/2017 | Suresh | A61B 34/30 |
| 2017/0333141 A1 | 11/2017 | Itkowitz et al. | |
| 2017/0333275 A1 | 11/2017 | Itkowitz et al. | |
| 2018/0021096 A1 | 1/2018 | Kostrzewski et al. | |
| 2018/0036090 A1 | 2/2018 | Hasegawa et al. | |
| 2018/0078319 A1* | 3/2018 | Nobles | A47B 21/03 |
| 2018/0214221 A1* | 8/2018 | Crawford | B25J 15/0441 |
| 2018/0228343 A1* | 8/2018 | Seeber | A61B 34/35 |
| 2018/0235719 A1* | 8/2018 | Jarc | A61B 1/04 |
| 2018/0235724 A1 | 8/2018 | Nowatschin et al. | |
| 2018/0256266 A1* | 9/2018 | Cohen | A61B 90/361 |
| 2018/0256268 A1* | 9/2018 | Cohen | B25J 18/06 |
| 2018/0310997 A1 | 11/2018 | Peine et al. | |
| 2018/0353246 A1* | 12/2018 | Ishihara | A61B 34/25 |
| 2018/0353247 A1* | 12/2018 | Ishihara | A61B 34/70 |
| 2019/0282311 A1* | 9/2019 | Nowlin | A61B 34/20 |
| 2020/0022762 A1* | 1/2020 | Cassell | A61B 90/50 |
| 2020/0100852 A1* | 4/2020 | Ishihara | A61B 90/60 |
| 2021/0085424 A1 | 3/2021 | Hulford | |
| 2023/0072201 A1* | 3/2023 | Regmi | B25J 5/007 |

FOREIGN PATENT DOCUMENTS

| | | |
|---|---|---|
| CN | 104095682 A | 10/2014 |
| EP | 2459098 A1 | 6/2012 |
| JP | 2009504418 A | 2/2009 |
| JP | 5560260 B2 | 7/2014 |
| JP | 6157786 B1 | 7/2017 |
| KR | 20110003229 A | 1/2011 |
| KR | 20120013205 A | 2/2012 |
| KR | 20130080909 A | 7/2013 |
| KR | 20140078491 A | 6/2014 |
| KR | 20150066727 A | 6/2015 |
| WO | WO-03019505 A1 | 3/2003 |
| WO | WO-2011115387 A2 | 9/2011 |
| WO | WO-2012127404 A2 | 9/2012 |
| WO | WO-2015183419 A1 | 12/2015 |
| WO | WO-2016069659 A1 | 5/2016 |
| WO | WO-2016164824 A1 | 10/2016 |
| WO | WO-2018013214 A1 | 1/2018 |

(56) References Cited

FOREIGN PATENT DOCUMENTS

OTHER PUBLICATIONS

International Preliminary Report on Patentability for Application No. PCT/US2018/043747, dated Feb. 6, 2020, 11 pages.
International Search Report and Written Opinion for Application No. PCT/US2018/043747, dated Nov. 7, 2018, 22 pages.
International Search Report and Written Opinion for Application No. PCT/US2018/043757, dated Jan. 21, 2019, 18 pages.
International Search Report and Written Opinion for Application No. PCT/US2018/043764, dated Jan. 21, 2019, 13 pages.
International Search Report and Written Opinion for Application No. PCT/US2018/043772, dated Jan. 21, 2019, 12 pages.
International Search Report and Written Opinion for Application No. PCT/US2018/043776, dated Jan. 16, 2019, 13 pages.
Manjunath T.C., et al., "Design and Development of Computer Vision Based Behavior Between Robots Using Swarm Intelligence," Communications in Dependability and Quality Management (CDQM), Nov. 1, 2013, vol. 16 (1), pp. 55-63.
Medgadget, "Cambridge Medical Robotics Shows Off Its New Versius System," Dec. 15, 2016, Retrieved from the internet< url:<a href="https://www.medgadget.com/2016/12/cambridge-medical-robotics-versius-system.html">https://www.medgadget.com/2016/12/cambridge-medical-robotics-versius-system.html, 2 pages. </url:<a>.
Medgadget, "Medineering Launches Research Edition of Its Platform for Surgical Robots," Oct. 26, 2016, Retrieved from the internet< url:<a href="https://www.medgadget.com/2016/10/medineering-launches-research-edition-platform-surgical-robots.html">https://www.medgadget.com/2016/10/medineering-launches-research-edition-platform-surgical-robots.htm . . . , 3 pages.</url:<a>.
Prichystal J.P., et al., "Invisible Display in Aluminum," Photon Processing in Microelectronics and Photonics IV, Apr. 2005, vol. 5713, pp. 215-222.

Tilo Wüsthoff, "DLR/miro," 2017, Retrieved from the Internet< url:< a="" href="https://www.behance.net/gallery/45566449/DLR-miro">https://www.behance.net/gallery/45566449/DLR-miro, 4 pgs. </url:>.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18837902.8 dated Mar. 12, 2021, 10 pages.
Office Action for Chinese Application No. CN2018800598933, dated Jun. 9, 2022, 18 pages.
Extended European Search Report for Application No. EP18839053.8 dated May 27, 2021, 09 pages.
"BionicCobot (English)", Festo AG & Co. KG, Esslingen, Germany. Product Video, Mar. 27, 2017, .mp4 format (64 MB), retrieved from the internet. URL: < https://www.youtube.com/watch?v=54u3H69tcgM >.
"BionicCobot: Sensitive helper for human-robot collaboration," Festo AG & Co. KG, Esslingen, Germany. Product Brochure. retrieved from the internet. URL: < https://www.festo.com/PDF_Flip/corp/Festo_BionicCobot/en/files/assets/common/downloads/Festo_BionicCobot_en.pdf >, 5 pgs.
"Cambridge Medical Robotics Shows Off Its New Versius System", Medgadget, Dec. 15, 2016 (retrieved on Jan. 30, 2019) Retrieved from the internet: <URL: https://www.medgadget.com/2016/12/cambridge-medical-robotics-versiussystem.html>, 2 pgs.
"Medineering launches research edition of its platform for surgical robots", Medgadget, Oct. 26, 2016. (retrieved on May 8, 2018). Retrieved from the Internet: < URL: https://www.medgadget.com/2016/10/medineering-launches-research-edition-platform-surgical-robots.html >, 3 pgs.
Office Action for Chinese Application No. CN20188059893, dated Nov. 10, 2022, 15 pages.

* cited by examiner

MEDICAL DEVICE HANDLE

CROSS-REFERENCE TO RELATED APPLICATIONS

This application is a U.S. National Stage Filing under 35 U.S.C. 371 from International Application No. PCT/US2018/043772 filed on Jul. 25, 2018, and published as WO 2019/023390 A1 on Jan. 31, 2019, which claims the benefit of priority to U.S. Provisional Patent Application No. 62/537,884, filed on Jul. 27, 2017, each of which is incorporated by reference herein in its entirety.

This application is also related to the following international patent applications filed with the U.S. receiving office on even date herewith: Application No. PCT/US2018/043747, entitled LIGHT DISPLAYS IN A MEDICAL DEVICE; Application No. PCT/US2018/043757, entitled INTEGRAL DISPLAY AND DISPLAY OF CONTENT; Application No. PCT/US2018/043764, entitled DISPLAY BETWEEN ARM LINKS IN A MEDICAL DEVICE; and Application No. PCT/US2018/043776, entitled MEDICAL DEVICE WITH ERGONOMIC FEATURES.

TECHNICAL FIELD

This document relates generally to medical devices, and more particularly, to user interface or ergonomic features in a medical device such as a teleoperated surgical system.

BACKGROUND

A teleoperated surgical system that operates at least in part under computer control includes one or more teleoperated manipulator arms that each include two or more interconnected links. The system may interface with other systems or devices, which may provide power or control signals. A surgical instrument may be mounted to an arm and controlled using a user control system.

SUMMARY

An example, ("Example 1") of subject matter (e.g., a medical device configured for use with a teleoperated surgical system) may include a control system, a movable manipulator arm, and a handle coupled to the manipulator arm, wherein in a first pose of the movable manipulator arm, the handle is oriented at a first convenient hold angle to a clinical user, wherein in a second pose of the movable manipulator arm different from the first pose, the handle is oriented at a second convenient hold angle to the clinical user, different from the first convenient hold angle, and wherein the control system comprises programmed instructions to automatically move the handle from the first orientation to the second orientation as the movable manipulator arm moves from the first pose to the second pose.

In Example 2, the subject matter of Example 1 may be configured or implemented such that the handle orientation is adjusted to present the handle at the second convenient hold angle based upon a user profile.

In Example 3, the subject matter of Example 2 may be configured or implemented such that the user profile includes a user height.

In Example 4, the subject matter of Examples 1-3 may be configured or implemented such that the orientation of the handle is user-adjustable.

In Example 5, the subject matter of any one or any combination of Examples 1-4 may be configured or implemented to move the handle relative to the manipulator arm to maintain the handle at a specified orientation.

In Example 6, the subject matter of Example 5 may be configured or implemented such that the specified orientation is an angle or range of angles.

In Example 7, the subject matter of Example 5 or 6 may be configured or implemented such that the specified orientation is determined with respect to a specified frame of reference.

In Example 8, the subject matter of any one or any combination of Examples 1-7 may be configured or implemented to receive information from an orientation sensor and adjust an orientation of the handle based on the information received from the orientation sensor.

In Example 9, the subject matter of any one or any combination of Examples 1-8 may include a user interface on the handle.

In Example 10, the subject matter of Example 9 may be configured or implemented to, responsive to input via the user interface, release the handle to enable manual adjustment of the orientation of the handle.

In Example 11, the subject matter of Example 9 or 10 may be configured or implemented such that manipulator arm is controllable via the user interface.

In Example 12, the subject matter of any one or any combination of Examples 9-11 may be configured or implemented to perform an auto-egress operation responsive to an input via the user interface.

An example ("Example 13") of subject matter (e.g., a teleoperated surgical system) may include a manipulator arm, a handle coupled to the manipulator arm, and a control circuit operatively coupled to the handle, wherein the control circuit executes instructions to control an orientation of the handle as the manipulator arm changes from a first pose to a second pose.

In Example 14, the subject matter of Example 13 may be configured or implemented such that the control circuit executes instructions to maintain an orientation of the handle with respect to a specified frame of reference.

In Example 15, the subject matter of Example 14 may be configured or implemented such that the control circuit executes instructions to maintain an orientation of the handle relative to horizontal.

In Example 16, the subject matter of Example 14 may be configured or implemented such that the specified frame of reference is a user height or position, wherein the control circuit executes instructions to maintain the handle at an orientation based on the user height or position.

In Example 17, the subject matter of Example 16 may include retrieving the user height or position from a memory circuit and using the retrieves user height or position to determine a handle orientation.

In Example 18, the subject matter of Examples 13-17 may further include an input device on the handle, wherein the control circuit is configured to control an operation based on an input received through the input device.

In Example 19, the subject matter of Example 18 may be configured or implemented such that the control circuit is configured to release, restrict, or lock a range of motion of the handle responsive to an input received through the input device.

In Example 20, the subject matter of Example 18 or 19 may be configured or implemented such that the control circuit executes instructions to perform an egress procedure responsive to a user input via the input device.

In Example 21, the subject matter of Examples 13-17 may further include a helm, the control circuit executing instructions to align the handle with the helm.

In Example 22, the subject matter of Example 13-17 may be configured or implemented such that the manipulator arm is positionable in a specified pose, the control circuit executing instructions to position the handle in a specified orientation that corresponds to the specified pose.

In Example 23, the subject matter of Example 22 may be configured or implemented such that the manipulator arm is positionable in a transport pose and the control circuit is configured to present the handle to a user in a push orientation when the manipulator arm is positioned in the transport pose.

In Example 24, the subject matter of Examples 13-17 may further include one or more motors configured to adjust the orientation of the handle, the one or motors being operatively coupled to the control circuit, the control circuit executing instructions to control the one or motors to control the orientation of the handle.

An example ("Example 25") of subject matter (e.g., a method of controlling a configuration of a manipulator arm and a handle of a teleoperated surgical system) may include moving a manipulator arm to a first pose, and automatically adjusting an orientation of a handle to a specified orientation responsive to movement of the manipulator arm to the first pose.

In Example 26, the subject matter of Example 25 may be configured or implemented such that adjusting the orientation of the handle includes positioning the handle in a consistent orientation through a range of positions of the manipulator arm.

In Example 27, the subject matter of Example 26 may include be configured or implemented to include positioning the handle in a horizontal orientation.

In Example 28, the subject matter of any one or any combination Examples 25-27 may be configured or implemented to include determining a handle orientation based on a frame of reference.

In Example 29, the subject matter of Example 28 may be configured or implemented such that the frame of reference includes one or more user parameters.

In Example 30, the subject matter of Example 29 the one or more user parameters may include a user height and handle may be moved to an orientation based at least in part on the user height.

In Example 31, the subject matter of any one or any combination of Examples 25-30 may further include performing an egress procedure responsive to a user input and adjusting the orientation of the handle to an egress orientation as part of the egress procedure.

In Example 32, the subject matter of any one or any combination of Examples 25-30 may further include receiving a user input through a user input device, the specified orientation of the handle determined based at least in part on the user input.

In Example 33, the subject matter of Example 32 may further include releasing the handle responsive to the user input may be configured or implemented such that the orientation of the handle is manually adjustable when the handle is released.

In Example 34, the subject matter of Example 32 may be configured or implemented such that a first user input indicating a first handle orientation when the arm is a first pose may be received, a second user input indicating a second handle orientation when the arm is in a second pose may also be received, and a specified third orientation of the handle for a third pose of the arm is determined based at least in part on the first user input and the second user input.

Each of these non-limiting examples can stand on its own, or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Overview

Figure 1A:
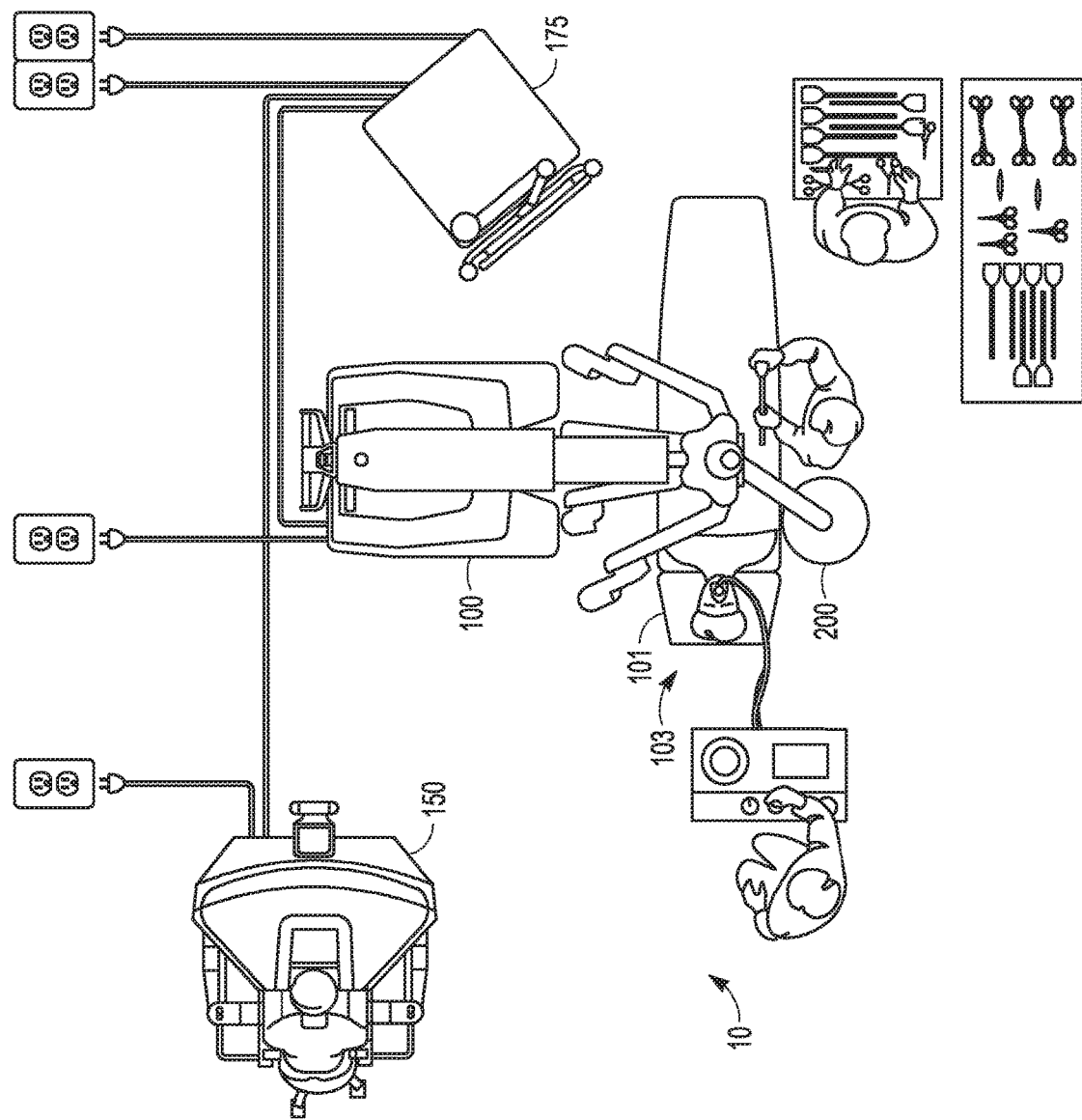
FIG. 1A is a plan view illustration of an example medical system that may include a user control system, an auxiliary system, and a manipulating system.

A manipulating system, such as a medical device or medical system (e.g., teleoperated surgical system that operates at least in part under computer control), may include one or more user-friendly features, such as a light feature (e.g., a light ring), an integral display that may be controllable to display content to or from a user, a display (e.g., an OLED display) between arm links in a medical device, or a controllable medical device handle. The system may be positionable in one or more kinematic postures or may include ergonomic features.

An example manipulating system may have two or three (or more) independently movable links that that may move relative to one another. Joints between the links may operate under motor power ("active joints") or may be unpowered ("passive joints") so as to be movable by hand. In some examples, the active joints may be teleoperated active joints that are controlled by inputs from a user through a user control system.

A modulating system may, for example, include a manipulatable arm, which may have discrete jointed links, or a multiplicity of links, or a continuous construction. The arm may be manipulatable into one or more predefined kinematic poses. A medical instrument, such as a grasper, cutter, cautery tool, stapler, or camera may be mounted at the distal end of the arm and may be and used to perform a therapeutic or diagnostic medical procedure. An example manipulator arm may include three main sections. The first section may be a teleoperated section (a "manipulator"), which may be controlled by a user such as clinician. A medical instrument may be mounted at a distal portion of the manipulator, and a clinician may move or control the instrument and operate features of the instrument via teleoperated control of the manipulator and associated equipment. A proximal portion of the first section of the manipulator arm may be coupled to a second section, which may be oriented or positioned to maintain the proximal end of the manipulator at a desired location in space. The second section may be active, passive, or both active and passive. The second section may also be teleoperated. A proximal portion of the second section may be coupled to a third section, which may for example include a column that extends generally upward from a base. The column may include one or more joints, which may be active, passive, or both active and passive. The column section may also be teleoperated. The second section and the third (column) section are optional. The manipulator may be coupled directly to the column or to the base, or the second section may be coupled directly to the base.

A manipulating system (e.g., arm) may actively move into one or more predefined poses, which may indicate readiness to perform a particular function, e.g., "ready to dock to a cannula" or "ready for transport across the floor" or "in standby and waiting for deployment to another pose." In various examples, system behavior or functionality (e.g., joint states, light states, user interface behavior) may vary based at least in part on a pose of the manipulating system.

A manipulating system may be designed to be modular, e.g., a modular manipulating system may be designed to work as a stand-alone unit, together with or as a part of a larger system, or with another modular system (e.g., side-by-side at a table, or across from each other at a table, or otherwise located together). For example, the system 200 shown in FIG. 2A-J and the system 900 shown in FIGS. 9A-C may optionally be configured as components in one or more modular systems. In some examples, two or more modular system may be configured to work in a coordinated manner, or to communicate with each other, or to move together, or share sensor information or instructions or other information, or any combination of these configurations. In various examples, a modular manipulating system may be on a movable base; or it may be mounted to a surgical patient or other medical table; or it may be mounted on a floor, wall, or ceiling of an operating room; or it may be mounted to another object in a clinical environment. And, in accordance with various aspects described herein, the base may be movable with reference to the surgical table, floor, wall, ceiling or other object to which it is mounted.

Aspects disclosed herein are by their nature interoperative because all are generally associated with designs for effective and safe human interaction with a teleoperated surgical system. It is contemplated that even though an individual aspect as described herein may stand alone as inventive, two or more aspects as described herein may be combined as inventive, too. For example, aspects associated with light features may be combined with aspects associated with controllable displays, and both may be combined with aspects associated with ergonomic touch points or controllable handles. To avoid prolix description, therefore, aspects described in one section of this description are not limited to technical application only within the context of that one section. For example, one or more aspects of a light feature described in one section may be combined with one or more aspects of a light feature described in another section. And, one or more aspects of one feature described in one section may be combined with one or more aspects of one or more other features described in one or more other sections. For example, one or more aspects of a light feature may be combined with one or more aspects of a handle.

Manipulating System Designed on a Human Scale

A manipulating system (e.g., the system 200 shown in FIGS. 2A-2J or system 900 shown in FIGS. 9A-E) may be designed to incorporate features that promote and guide human interaction, taking account of human psychological and physiological principles. An important psychological aspect of human-machine interaction occurs even before a machine is touched. For example, a system may include a manipulator arm (such as arm 204, 904 shown, e.g., in FIGS. 2A and 9A) that is designed by its appearance to communicate approachability or safety to a human operator, for example as shown in FIGS. 2A-2J, and 9A-9E. In contrast to the examples shown in FIGS. 2A-2J and 9A-9E, other robots (industrial or surgical, see, e.g., prior art FIGS. 14-15) present sharp edges, pinch points, lumps and bumps, and other intimidating features that are less inviting for human physical interaction and do not appear to be safe or wise to stand next to or touch. For example, even smoothed links present certain perceived danger areas that a user is reluctant to touch due to real or perceived points that might pinch, crush, shear, cut, or otherwise injure, or even due to perceived bulkiness and unwieldiness.

The system shown and described herein may have consistent circular or rounded cross section from the column along the arm and across the joints until the distal end. (See, e.g., FIGS. 2A-2J, 9A-9E; compare FIGS. 14-15.) For example, the system may include straight links that are connected by curved links (e.g., shaped similar to "elbow macaroni") that maintain the consistent circular or rounded cross section of the other links of the arm. The curved links may be shorter than the straight links. In various examples, the user's body parts (e.g., fingers, hands or arms) cannot get pinched or trapped by arm links, due at least in part due to the configuration of the arm with a consistent cross section and rounded surfaces that space coupled links apart from one another. Joint range of motion limits may further prevent pinching or trapping. The consistent and rounded appearance may also communicate a lack of pinch or injury points and a general sense of safety for the user. (Compare FIGS. 14-15.)

Some systems may include a column that has a cross section and size that is similar to the arm portions to further promote the overall human factors design principals. (See, e.g., FIG. 2B and FIG. 9A.) The column portion may include an optional telescoping joint. The column may rotate with respect to the arm, the base, or both. An optional handle link may be included at a joint location. (See FIGS. 2A and 2B.) The configuration and location of the handle may convey safety and friendliness for human physical contact and interaction.

Displays

Various displays may be optionally incorporated into the patient-side unit, and especially into the arm. For example, LED and/or OLED lights and light displays of various colors may be used, and they may be directly visible, or they may indirectly illuminate another piece or pieces. For example, LED lights may be visible to a person looking at the patient-side unit, or LED lights may illuminate other pieces or structures such as translucent rings or bars. Similarly, OLED screens may be integrated into the unit, such as in a link of an arm or at a joint between two major links of the arm. Words and symbols, both either static or animated, both with either static or changing color or brightness (e.g., hard on/off flash, or softer more gradual flash), may be variously displayed as clinically necessary or appropriate to convey information such as system, arm, or instrument status. For example, the display or displays may be used to identify an arm or device, to lead a user through a sequence of steps associated with operating the patient-side unit, to convey joint range of motion limits, to an identify instrument type associated with the patient-side unit, to indicate the source of a command or operation (e.g., a teleoperated command from a user control unit, or automatic, or manual), to indicate a posture of a device, or to communicate other information.

Light Features

An arm portion of a manipulating system, or other portions, may include one or more light features. A light feature may be configured or controlled to provide information to a user, such as a clinician, about the state of the system or the state of a medical device. For example, a light feature may be at an interface, and may be controlled to provide information about the interface, such as information about a connectivity state, a configuration state, or a movement state. A light feature (e.g., light ring) may, for example, be at an interface between portions (e.g., at or near a joint between arm links) of a medical device and may be controlled to communicate information about the relative state between the portions (e.g., joint angle, joint position relative to joint range of motion, or joint movement state). A light feature may additionally or alternatively be at an interface with another device, and may communicate information about a whether another device is coupled to the medical device at the interface, the type of coupled device, or a control parameter (e.g., which device is receiving or delivering control signals). In some examples, a medical device may include multiple light features, each of which is controlled or configured to provide information about a different aspect or state of the medical device. Some examples may include an integral display that may be configured to be viewable by a user when information is presented, and to disappear when information is not presented. An integral display may, for example, identify a manipulator arm, or provide information about an operating mode or a phase or status of a procedure. A display between links or on a handle may be configured to provide context-sensitive information, or assume a context-sensitive position, or "follow a user" so that the handle or display is easily reachable or viewable to a user or from a specified user reference position in two or more different arm positions or configurations.

Handles

A manipulating system may include one or more handles that facilitate operation of either the system as a whole or a part of the system. Any of the handles described below may include a display or light feature. A handle orientation, or a display or light feature on or near the handle, may be controlled to facilitate use of or interaction with the system by a user. The orientation of one or more handles, or the state of one or more displays or light features (on or near the handle, or elsewhere on a system), may be coordinated to provide a consistent communication to a user, or may be coordinated based on a state of the system or a mode of operation. Handles, lights, and displays may be controlled by a processor in a modular system into which they are integrated (e.g., a control circuit for the modular system, or a control circuit for a portion of a system, or a control circuit for a joint, or a control circuit in or at the handle, light, or display), or by a separated user control system, or separate processing equipment.

Example Systems

FIG. 1A is a plan view illustration of an example medical procedure environment that may include a multi-arm manipulating system 100 adjacent to a surgical table 101 that may support a patient 103. A second manipulating system 200 may also be situated at the surgical table 101. The manipulating systems 100, 200 may be free-standing on a movable base, or they may be mounted to a table, floor, wall, or ceiling, or they may be supported on another piece of equipment in the clinical environment.

The manipulating system 100 or system 200 may be part of a larger system 10, which may include other sub-systems (e.g., fluoroscopy or other imaging equipment). For example, one or both of the manipulating systems 100, 200 may be operatively coupled to a user control system 150 or an auxiliary system 175, or both. The user control system 150 may include one or more user input devices (e.g., controls) that may be configured to receive inputs from a user (e.g., clinician). The user control system 150 may also include or one or more user feedback devices (e.g., viewing system or tactile or auditory feedback) that may be configured to provide information to the user regarding the movement or position of an end effector, or an image of a surgical area. The auxiliary system 175 may, for example, include computer processing equipment (e.g., a processor circuit or graphics hardware) or communication equipment (e.g., wired or wireless communication circuits).

Figure 1B:
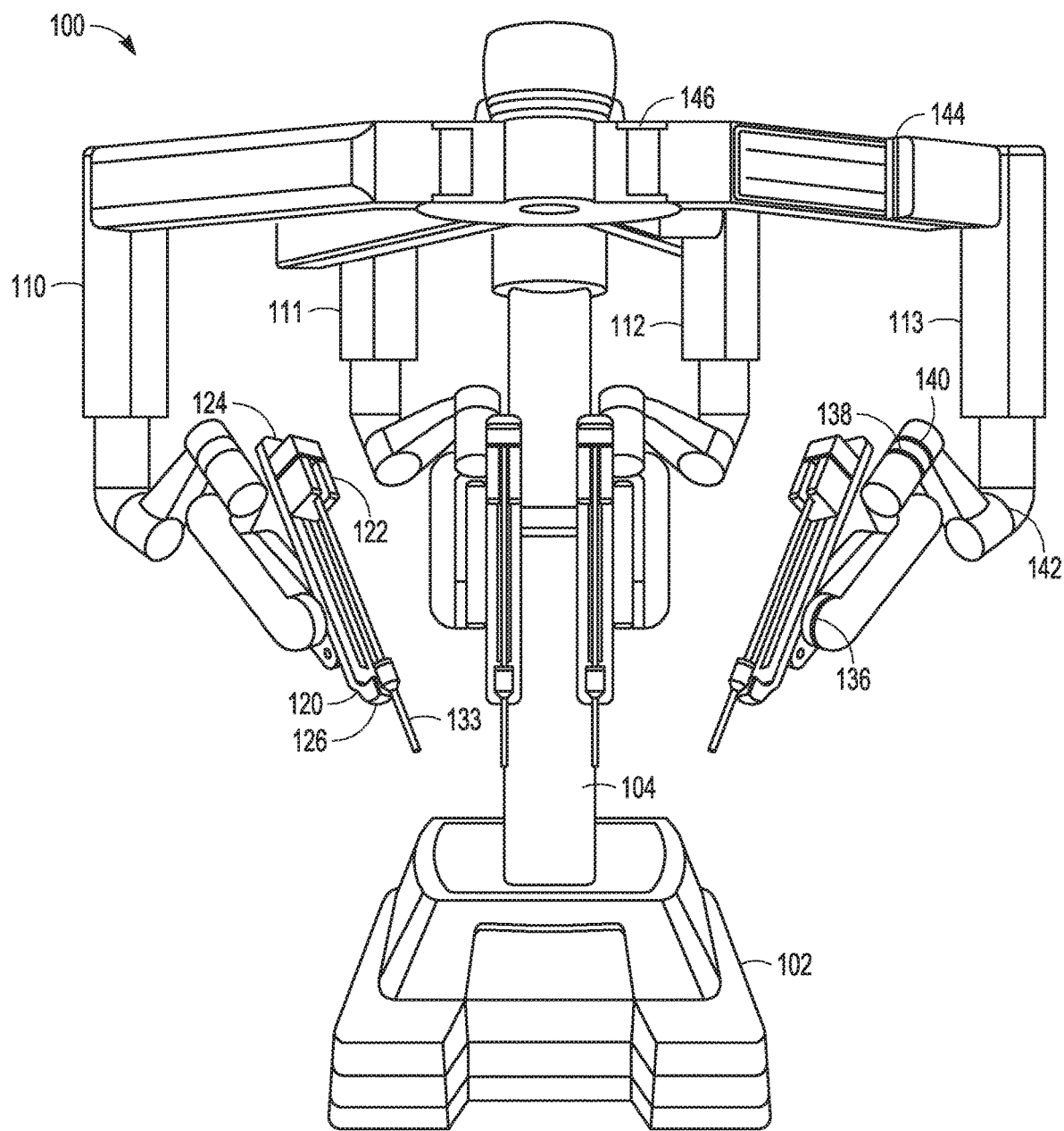
FIG. 1B is an illustration of an example manipulating system.

FIG. 1B is an illustration of example manipulating system 100. The manipulating system 100 may include a base 102, a support tower 104, and one or more manipulator arms 110, 111, 112, 113, which may be mounted on the support tower 104. An instrument 130 (shown in FIG. 1E) may be mounted to an instrument mount 120 on one of the manipulator arms 110-113. The instrument mount 120 may, for example, include an instrument carriage 122, which may be mounted to a spar 124, which may be a telescoping spar as described below in reference to FIG. 10. A cannula 133 may be mounted to a cannula mount 126, and the instrument 130 may be inserted through a cannula seal in the cannula 133, and into the patient 103 (FIG. 1A) for use in a surgical or other medical procedure. Through movement of the manipulator arms 110-113, the orientation of the instrument 130 may be controlled in multiple dimensions, e.g. lateral, horizontal, vertical, angular movements in one, two, or three planes. The system 100 may include one or more light features 136, 138, 140, 142, 144, 146 at one or more of a variety of locations on the manipulator arms 110-113 (i.e., at joints between arm links, as shown).

Figure 1C:
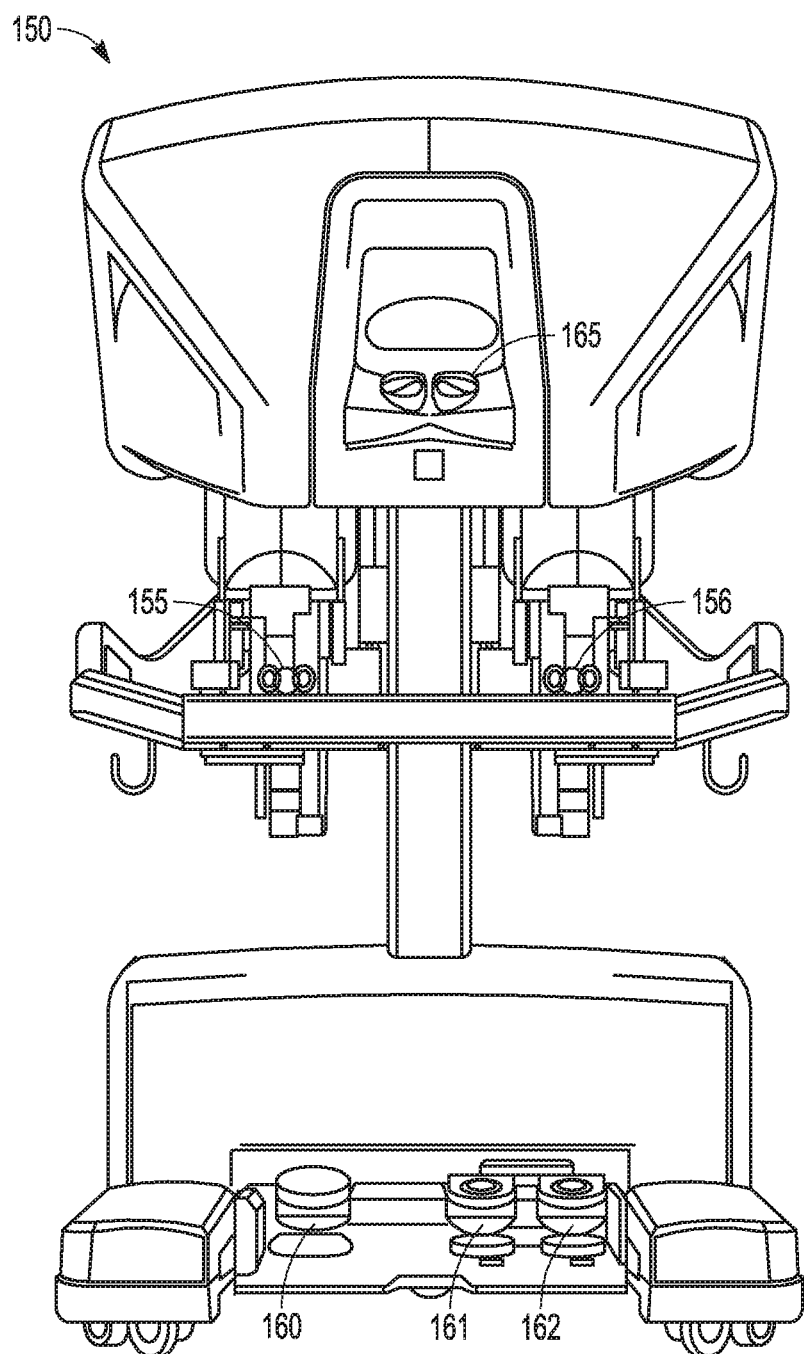
FIG. 1C is an illustration of an example user control system.

FIG. 1C is an illustration of example user control system 150. The user control system 150 may include hand controls 155, 156 and pedal controls 160, 161, 162. The hand controls 155, 156 and pedal controls 160, 161, 162 may be used to control equipment at one or more of the manipulating systems 100, 200. For example, portions of a distal end of an instrument 130 may be manipulated using the instrument controls. The controls may include haptic feedback features so that a physician may interpret physical information at the instrument 130, such as resistance or vibration, through the controls. The user control system 150 may also include a viewing system 165 that may display video or other images of a surgical site.

Figure 1D:
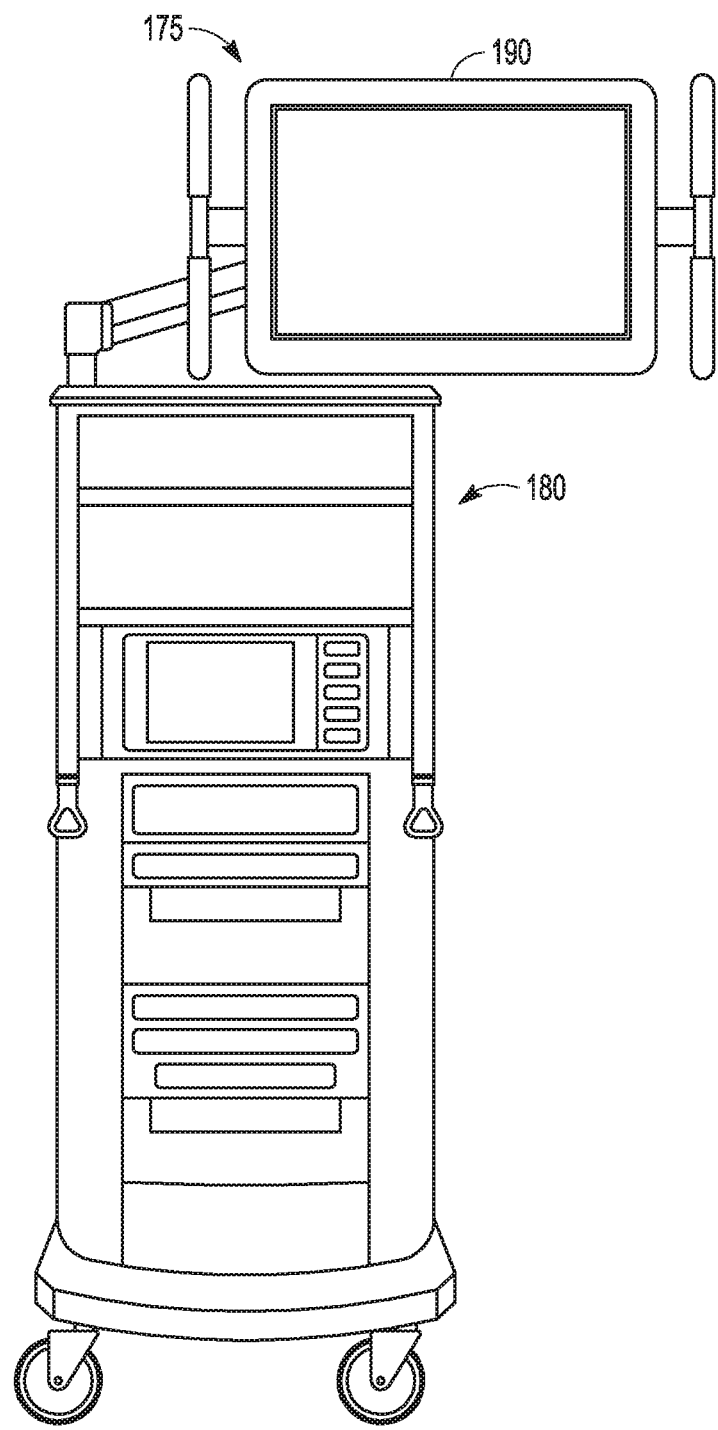
FIG. 1D is an illustration of an example auxiliary system.

FIG. 1D shows example auxiliary system 175. The auxiliary system 175 may include computer processing system 180 for processing controls, facilitating communication between the user control system and the manipulating system, or a remote site. The auxiliary system 175 may also include a display 190, which may show images that the user (e.g., clinician) is seeing on the user control system 150, a video feed from a camera in the patient 103, or other information. In an example configuration, signals input at a user control system 150 may be transmitted to the processing system 180 on the auxiliary system 175, which may interpret the inputs and generate commands that are transmitted to the manipulating system 100 to cause manipulation of an instrument 130 or portions of a manipulator arm 110. The processing system 180 is shown on a cart for exemplary purposes, but may also be arranged in various configurations, e.g., it may be integrated as part of the user control system 150, the manipulating system 100, 200, or both, or divided between the user control system 150 and manipulating system 100, 200. The equipment may also be provided as software, hardware, or both, on an installed or remote system.

Figure 1E:
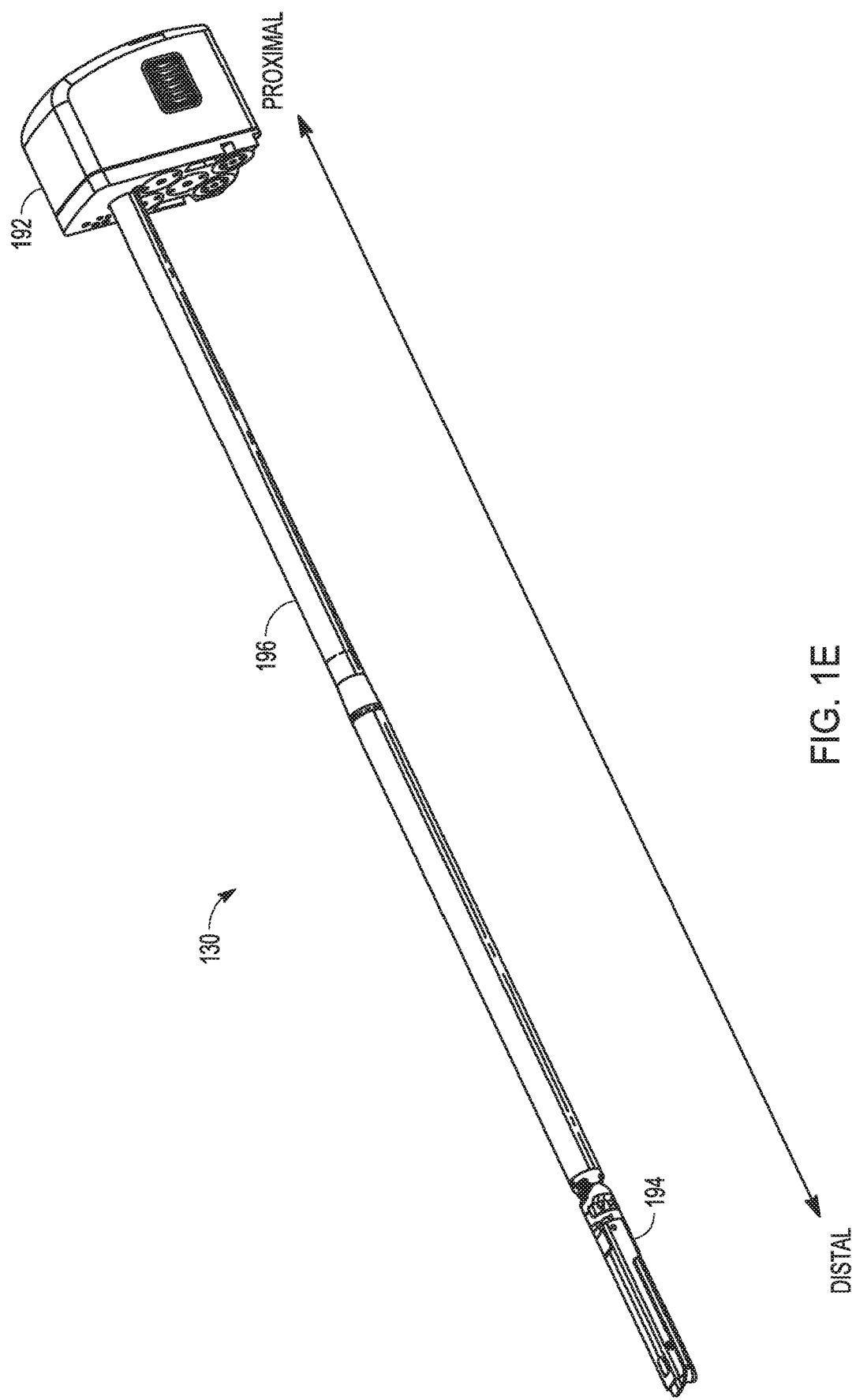
FIG. 1E is an illustration of an example instrument.

FIG. 1E is an illustration of an example instrument 130. The instrument 130 may include a proximal portion 192 that may be configured to couple to an instrument mount on a manipulator arm, such as the instrument mount assembly 1002 shown in FIG. 10. The instrument 130 may also include a distal portion 194 and an instrument shaft 196 between the proximal portion 192 and the distal portion 194. The distal portion 194 may be a cautery tool, cutter, camera, stapler, or other medically relevant end effector. The instrument 130 may be teleoperatively controlled via command signals received from a control computer, such as a user control system 150 or auxiliary system 175 to conduct a surgical procedure. Inputs may be received from a user (e.g., clinician), and the instrument 130 may be controlled based on the user inputs.

In an example, the position, orientation, or motion of an end-effector may follow the motion of the input device coupled to a controller, i.e., the position and pose of the end effector follow the position and pose of the input device, which may be controlled by a clinician. This may be referred to as "following mode", meaning the end effector motion follows the input device motion. Hardware or software to implement a following mode feature may be implemented in the system 100 shown in FIGS. 1A and 1B, in the system 200 shown in FIGS. 2A-2J, in the system 900 shown in FIGS. 9A-E, and in other similar systems.

Figure 2A:
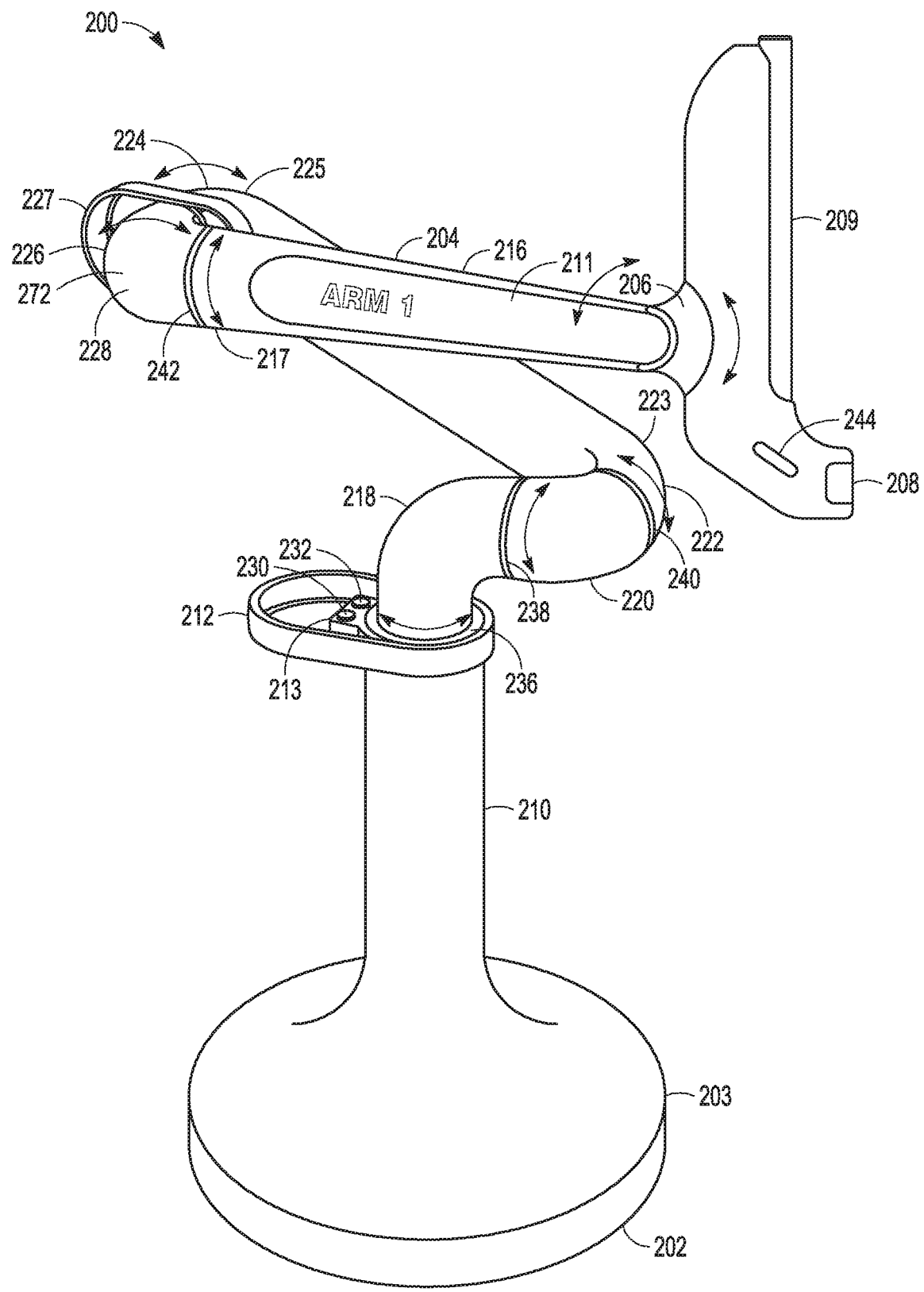
FIG. 2A is a perspective illustration of an example manipulating system.
Figure 2B:
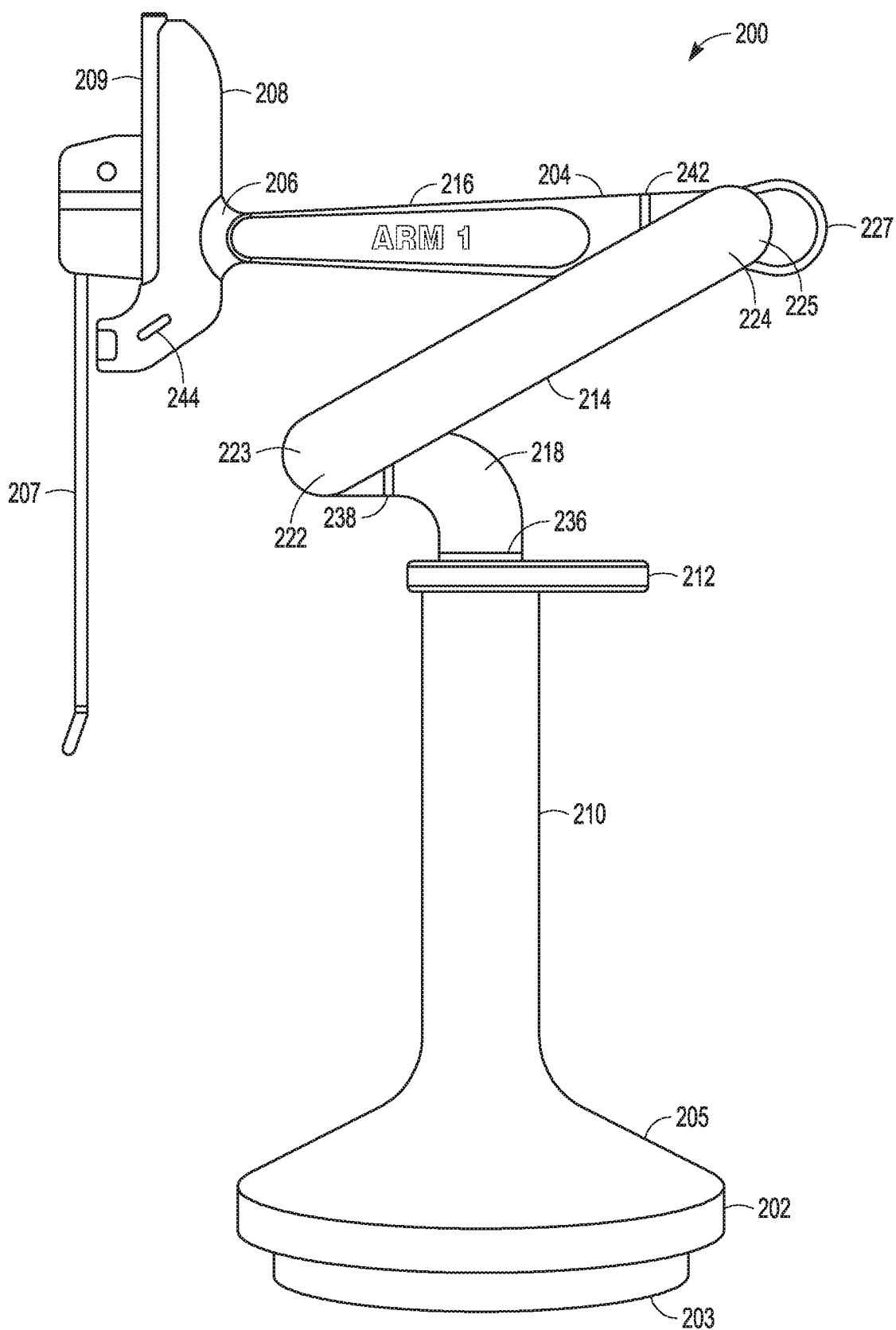
FIG. 2B is a side view illustration of the example manipulating system shown in FIG. 2A.

FIGS. 2A and 2B are respective perspective and side view illustrations of example manipulating system 200. The manipulating system 200 may be used with or be part of a medical system, such as the system 100 shown in FIG. 1A, which for example may be or include a da Vinci® surgical system commercialized by Intuitive Surgical, Inc., Sunnyvale, Calif. In various examples, the manipulating system 200 may be used in combination with the manipulating system 100 shown in FIG. 1B, or with the user control system 150 shown in FIG. 1C, or the auxiliary system 175 shown in FIG. 1D. The same computer or a different computer may control the movement of the arms, joints, lights, or other aspects of the unit, and the same computer or a different computer may control the manipulating system 200 and other manipulating systems (e.g., system 100 or system 900). In some examples, two or more manipulating systems 200, 200' may be used together to conduct a computer-assisted teleoperated surgical procedure controlled by a clinician (e.g., see FIG. 2F).

Figure 2C:
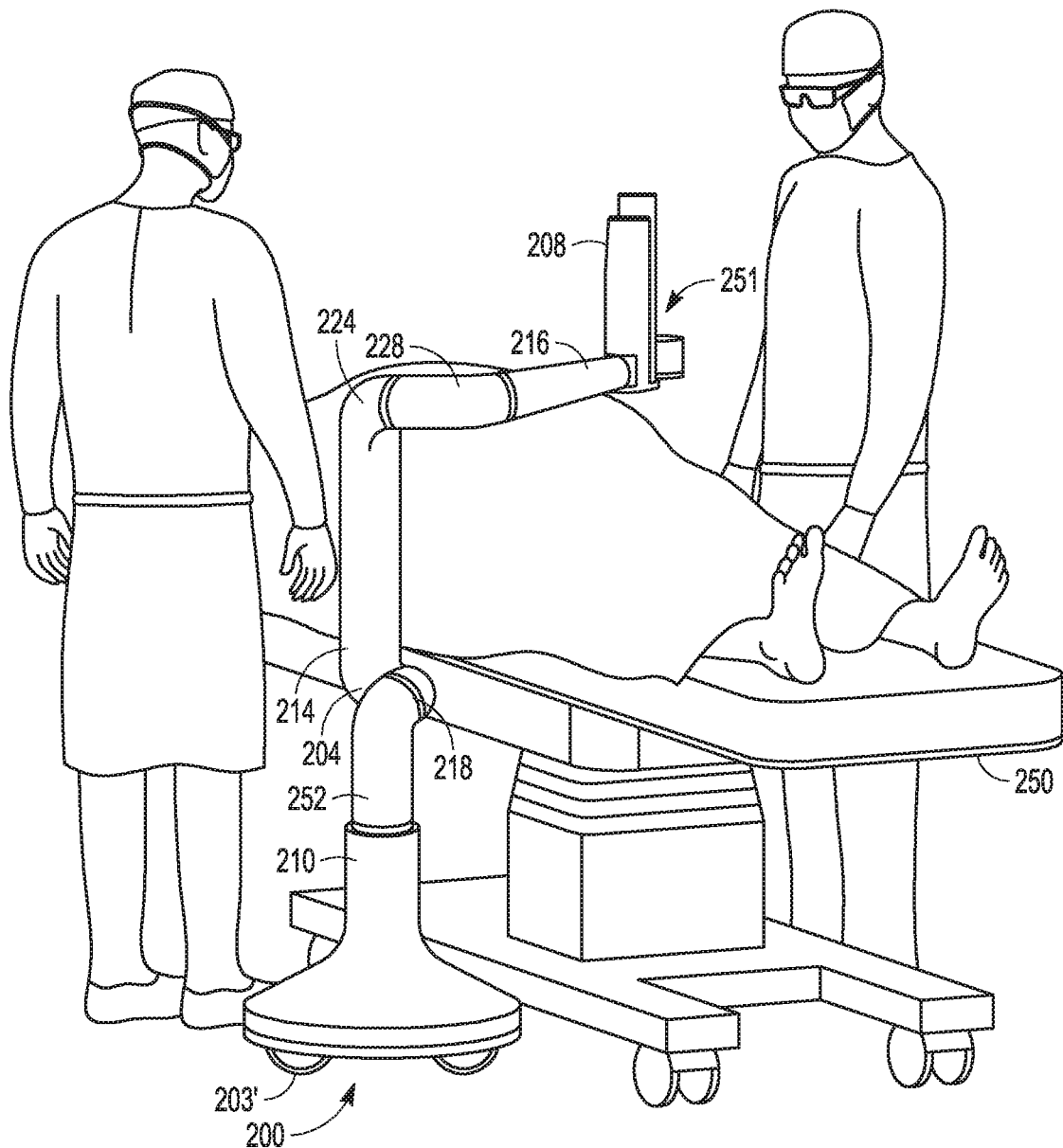
FIG. 2C is an illustration of a manipulating system positioned over a surgical table.

The manipulating system 200 may include a base 202, which may be configured to roll on the floor, for example, using a plurality (e.g., three, four, or five) roller balls 203 (hidden under the base 202 in FIG. 2B) or horizontally rotatable caster wheels 203' (shown in FIG. 2C). The rotatable casters 203' or roller balls 203 (e.g., three or five casters or roller balls) may provide a low height profile, may provide omni-directional movement, or both. In an example, five roller balls may be used, which may provide more stability than three roller balls. The balls may, for example, be a flange ball transfer available from Ashland Conveyor, Ashland, Ohio. The balls may be one (1) inch (2.54 cm) in diameter, and may be formed from carbon steel.

In some examples, a user-engageable switch may engage or release one or more brakes (not shown) on the base rollers, wheels, or casters (or the user-engageable switch may engage or release other equipment (e.g., a drive motor)) to allow the base 202 to move along the floor, or lock the base in position, or allow only a defined range of movement (e.g., movement in a circle or around a circle by locking one or more rollers, wheels, or casters). The system 200 may include an optional touch sensor on an arm 204, on the base 202 or elsewhere, that releases the brake on base rollers, wheels, or casters to allow the base 202 to move along the floor. For example, the system 200 may include a foot switch on the base 202. In some examples, the system 200 may include a "two-factor" switch (physical or logical) to assure deliberate activation (e.g., the system may require simultaneous or sequential engagement of two buttons or two inputs to release a brake). In some examples, the system 200 may include a "dead man switch" so that the base 202 stops when the switch is released. User-engageable switches may be associated with useful system transport modes or poses, such as the "IV stand" (mimicking the common intravenous fluid support stand) pose and transport poses described below. In some examples, the functionality of a switch (e.g., which feature or component the switch controls or affects, or the result of actuating the switch) may vary based upon a pose of the system (e.g., IV stand or other transport pose), or based upon a mode of the system (e.g., following, clutch state, awake state), or based upon another condition or state. In various examples, a component of the system 200, such as a handle, touch point, or helm may be or include a user input for a brake, brake release, dead man switch, or other switch.

In some examples, the base 202 may include variations in color (e.g., grey) or material (e.g., ridges, other textures) to visually communicate foot or hand push-points to a user. For example, a feature or aspect of an arm (e.g., arm geometry or handle) may invite a user to touch or grab the arm (as further described below). The base 202 may similarly indicate a physical touch point for a foot of a user, e.g. a foot push point. The foot push point may, for example, invite the user to use a foot to contact the base 202, based upon the placement (e.g., near the edge of the base), color (e.g., different from main unit color), texture (e.g., ridged or channeled similar to other foot tread features), or appearance of the foot push point.

As shown in FIG. 2B, the base 202 may include a foot push pad 205, which may be made of a rugged or high-friction material to facilitate manipulation of the position of the manipulating system by a foot of a user. The foot push pad 205 in combination with the roller balls 203 or casters 203' may accommodate a user pushing against the base 202 with a foot to translate or reorient the base 202 on the floor.

The base 202 may be compact to fit near a table (e.g., a surgical table). The compact form of the base 202 may avoid taking up standing space near the table to be as minimaly interfering as possible to clinical personnel, or may accommodate side-by-side positioning of other manipulating systems by being shaped to allow close spacing (e.g., see FIG. 2F). In some examples, the base 202 may be symmetric, which may avoid orientation or configuration problems at the bedside (e.g., see FIGS. 2A, 2B, and 2F). In other examples, the base 202 may be asymmetric to provide both stability and compactness (e.g., see FIGS. 9A-9B).

Figure 9A:
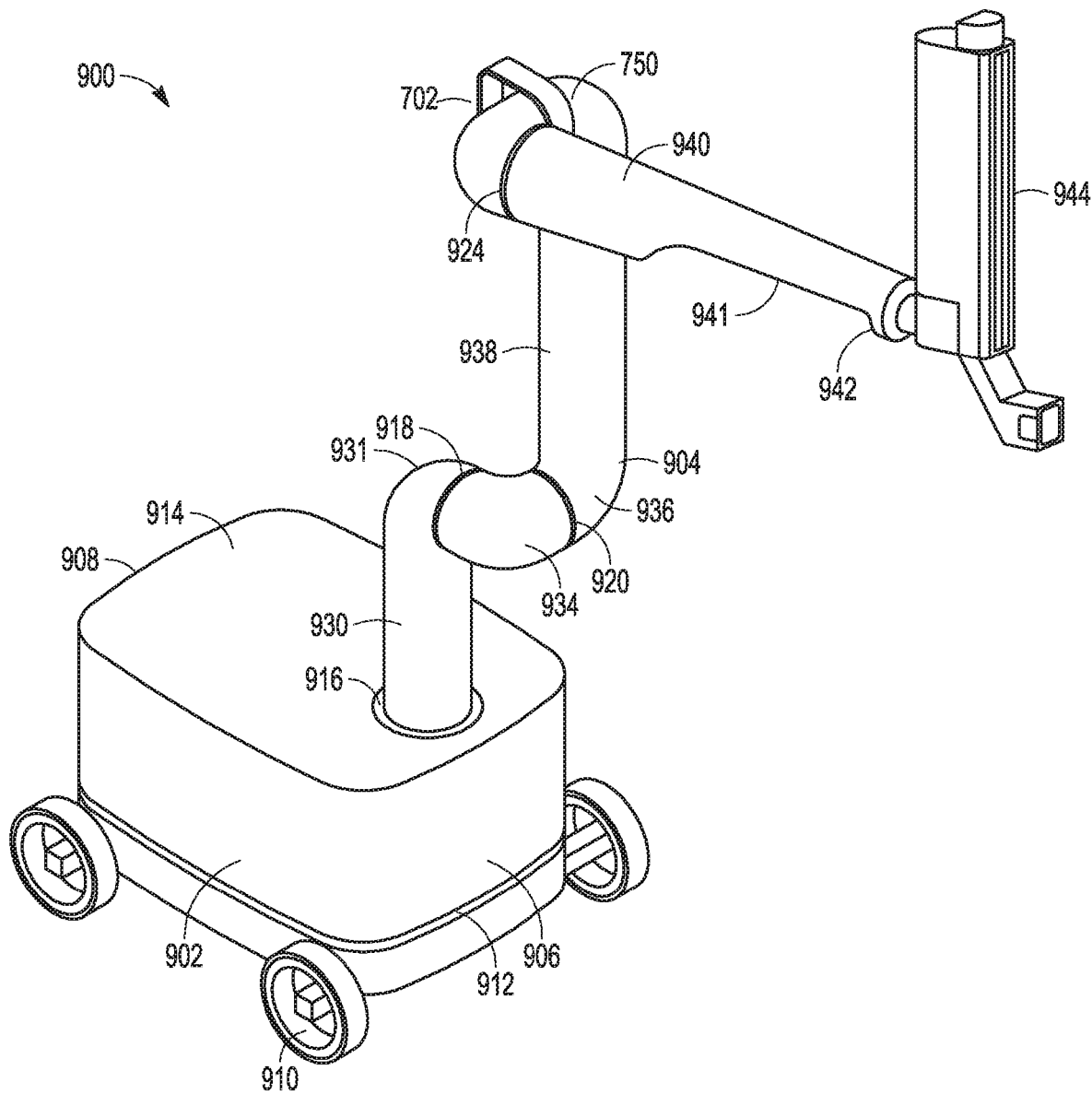
FIG. 9A is an illustration of another example manipulating system.
Figure 9B:
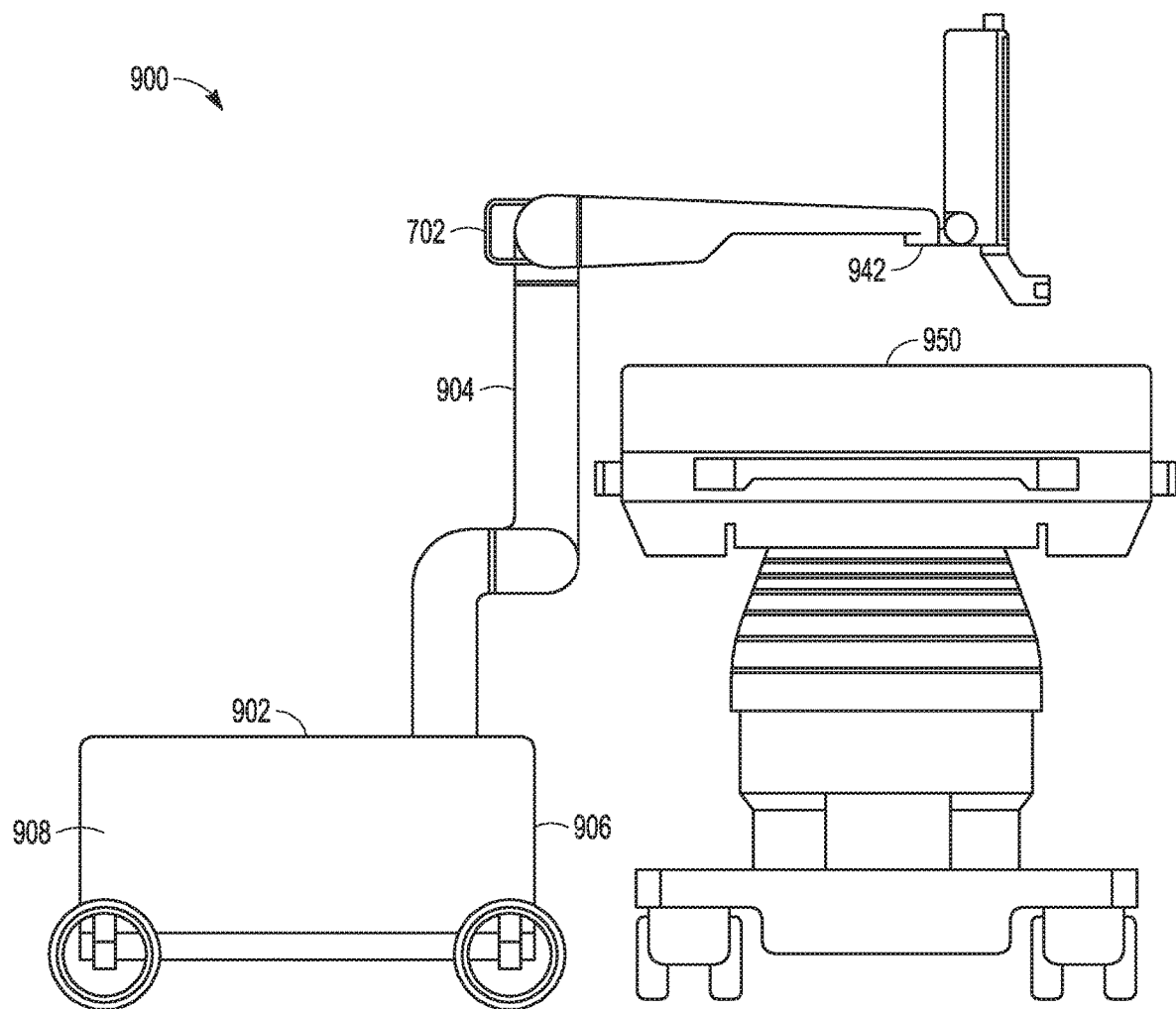
FIG. 9B is an illustration of an example manipulating system and a surgical table.
Figure 9C:
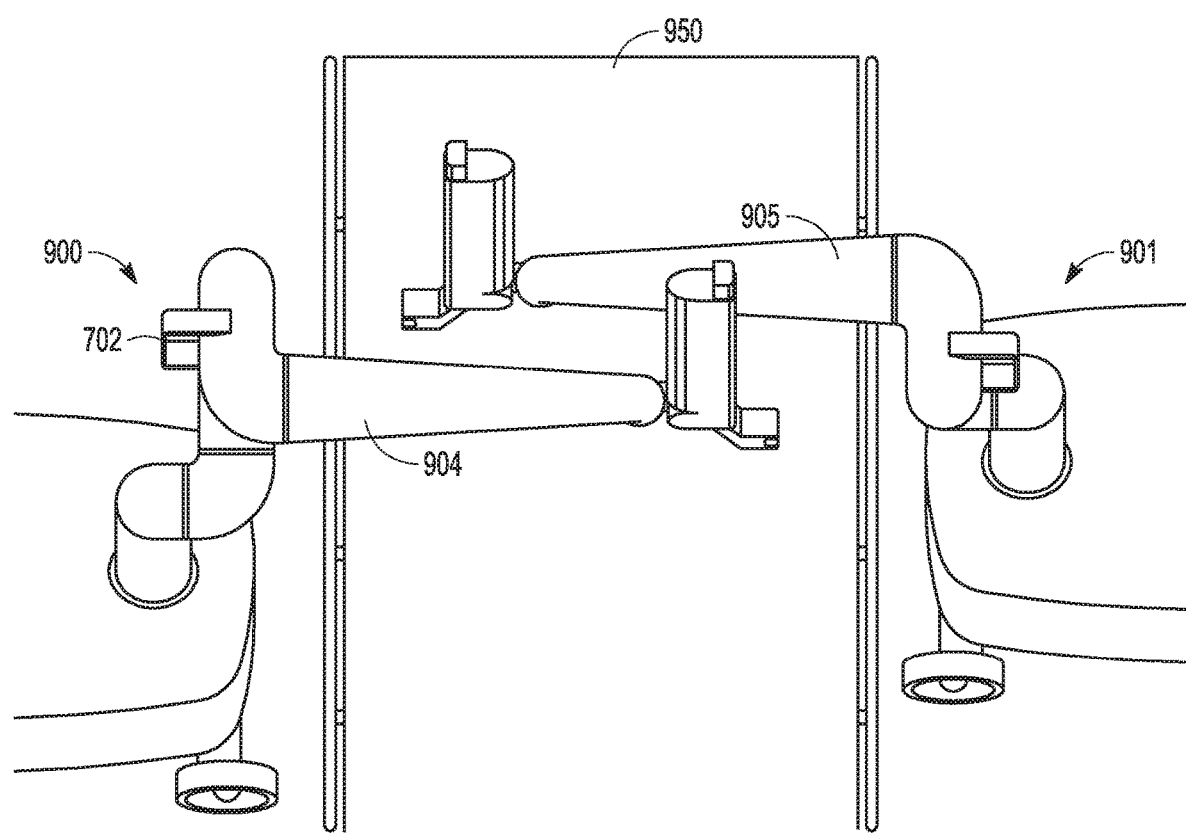
FIG. 9C is an illustration of two manipulating systems and a surgical table.

The manipulating system 200 may include an arm 204, which may include a forearm 211 that may be coupled at a wrist portion 206 to an instrument mount 208 and to the base 202. The wrist portion 206 may be configured to have one or more rotational degrees of freedom, e.g., the wrist may yaw, pitch, or roll to adjust the position of the instrument mount 208, as shown in FIG. 9E and described in reference thereto. In some examples, the forearm 211 may roll, and the wrist portion 206 may yaw and pitch. The instrument mount 208 may include a telescoping spar 209 (see also telescoping spar 1012 in FIG. 10.)

The manipulating system 200 may include a column 210 extending upward from the base 202. The column 210 may move (e.g., rotate or translate) with respect to the base 202, the arm 204, or both. In some examples, the column 210 may rotate relative to the base 202 at a column-base interface. A rotatable column 210 may be particularly useful when the base 202 is non-symmetric, as shown in FIG. 9A-9C. The column 210 may optionally include two or more separate column portions (not shown), which may move with respect to one another.

The manipulating system 200 may also include a helm 213 (also shown in FIG. 8), which may for example be positioned at the top of the column. The helm 213 may be at any horizontal rotational angle or vertical rotational angle relative to the base 202. For example, the helm 213 may be perpendicular to the column 210, or the helm 213 may be inclined downward from the column 210. In some examples, the helm 213 may be 90 degrees or 180 degrees from bedside when the unit is in "neutral" position (that is, generally at mid-range of teleoperated arm DOFs as used during a medical procedure) at the bedside. The helm 213 may also be arranged at other angles with reference to the bed. In some examples, the helm 213 may rotate around the column 210 portion of the arm 204 so that the helm's orientation can be easily adjusted.

The helm 213 may, for example, be arranged and configured to move and extend in an opposite direction from the forearm 211. For example, the helm 213 may rotate with the elbow 218, or column 210 may include a rotatable portion upper link coupled to the arm 204 and that moves (e.g., rotates) relative to a lower link of the column portion on which the helm 213 is mounted.

Figure 8:
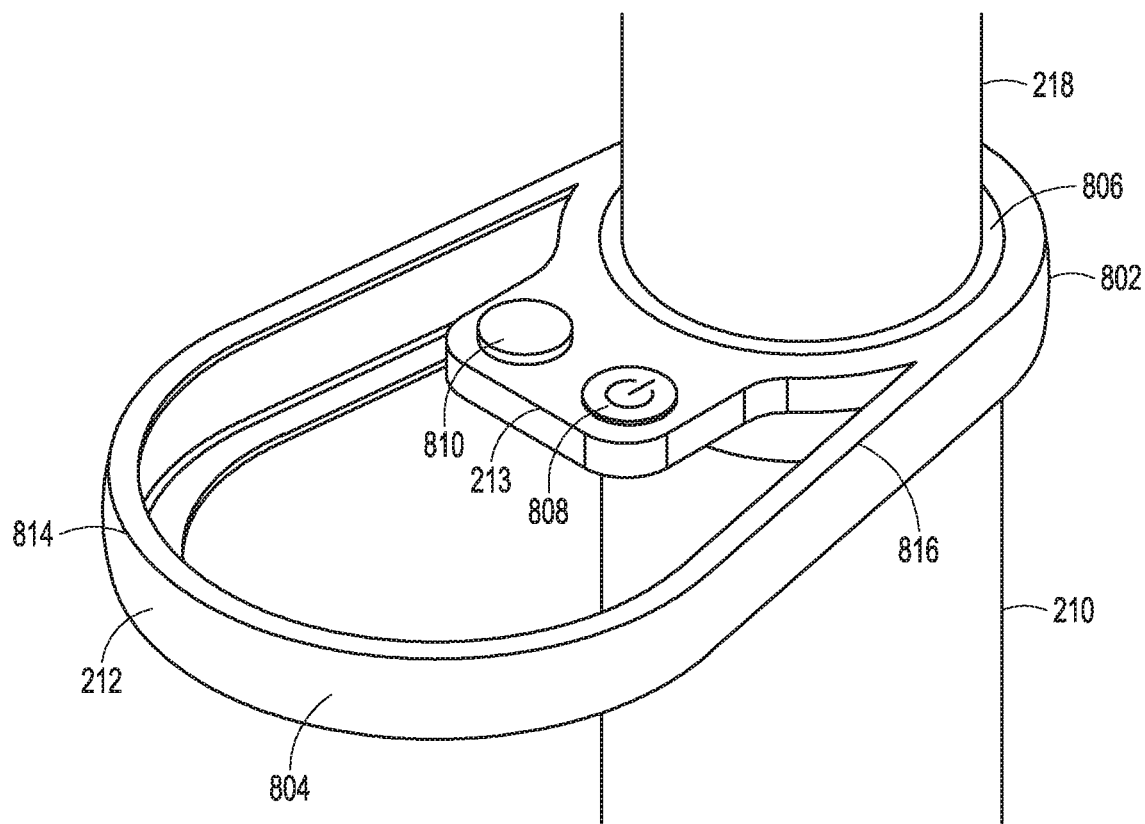
FIG. 8 is an illustration of a helm.

An enlarged perspective view of the helm 213 is shown in FIG. 8. The helm 213 may include one or more buttons 808, 810. Button 808 may, for example be a power on/off button that may turn power to the system 200 on and off. Button 810 may, for example, be a start/stop button that may start or stop movement of the system, or release the system to allow movement (e.g., activate or deactivate a clutch). The button 810 may be an emergency start/stop button. In some examples, the helm may include a handle 804, which may flare out from the helm column mount location 802 to provide a wider grab length for the hand of a user at a helm grab location 814. A light feature 806 may be provided at an interface between the helm 213 and the column 210, or at an interface between the helm 213 and elbow 218, or both. The light feature 806 may, for example, be a ring that extends part way or all of the way around the column 210. In some examples, the helm 213 may be configured to be sterile. Or, the helm 213 may be configured to be non-sterile, in which case the helm 213 may be positioned relatively low on the manipulating system 200 and away from the sterile field, and so the helm 213 may not be required to be draped during a surgical procedure (drape not shown).

Returning to FIGS. 2A-2J, in various examples, the arm 204 may be configurable to allow for positioning of the instrument mount 208 and an attached instrument 207 with respect to a patient and surgical table, as shown for example in FIG. 2C. In various examples, the arm 204 may be continuously flexible, or the arm 204 may include a plurality of links, which may be configured to move with respect to one another. Links may be long or short, and may be straight, or may include a bend, angle, or twist. The manipulating system 200 may also include one or more elbows, which may be configured with a bend (e.g., at 90 degrees, 45 degrees, or 30 degrees) to facilitate relative movement of links with respect to each other or to the base 202. In some implementations an elbow is a separate curved link with a joint at each end, and in some implementations an elbow is integral at one end of an extended straight link and has a joint at the free end of the elbow curve. Short or long straight links may be between discrete or integral elbows. And, a short or long straight link may have an integral elbow bend at one or both ends. The manipulating system 200 may be configured to provide angular movement at the interface between two links or elbows, e.g., an elbow and a link may be coupled together at a planar interface, and the elbow and link may rotate with respect to each other around a rotation axis that is orthogonal to the planar interface, as indicated by arrows. Such movement may, for example, be controlled by one or more electric motors, which may be operatively coupled to a control system, such as the user control system 150 shown in FIG. 1C. The system 200 may include an access panel on an arm, elbow, or other location to provide access to a motor, a display inside the arm (described below), or other internal components. Example access panels 450, 452 at elbows are shown in FIG. 4B. In some examples, the movement of the system 200 may additionally or alternatively be manually controllable, such as by using buttons on the system 200 or by manually moving arms, elbows, or other components.

In some examples, the arm 204 may include a combination of links and elbows, which may have a consistent cross section throughout some or all of the arm 204 (with the optional exception of a tapered forearm). For example, as shown the manipulating system 200 may include a first link 214 and a second link 216 coupled to the first link 214. The first link 214 and second link 216 may be coupled to each other and to the column 210 by one or more other links or elbows. For example, the manipulating system 200 may include a first elbow 218, which may be rotatably coupled to the column 210. The first elbow 218 may also be configured to telescope (e.g., move upward) relative to the column 210. The system 200 may also include a second elbow 220, which may be rotatably coupled to the first elbow 218. One or both of the links 214, 216 may include a bend. For example, the first link 214 may include a first bend 222 at a proximal portion 223 and a second bend 224 at a distal portion 225. For the purpose of describing the system 200 shown in FIGS. 2A and 2B, when considering a path along the arm 204 from the column 210 to the instrument mount 208, "proximal" refers to positions toward the column 210 and "distal" refers to positions toward the instrument mount 208. The manipulating system 200 may include a short link 226 between longer links. The short link 226 may be coupled to the distal portion 225 of the first link 214. In various examples, the short link 226 may include a handle 227 as shown, a display (e.g., see FIGS. 4A and 4B), or a display on a handle (e.g., see FIGS. 7A and 7B). The system 200 may also include a third elbow 228 that may be rotatably coupled to a distal side of the short link 226. The third elbow 228 may be rotatably coupled to a proximal portion 217 of the second link 216. In other examples, the system 200 may include more, or fewer, links or elbows. As shown, the elbows and bends alone (e.g., elbows/bends 224 and 228), or the elbows and bends with a short link in between (e.g., elbows/bends 224 and 228, with link 226) offset longer links that swing in parallel planes (e.g., 214, 216) from each other. As a result, there is a safety clearance between the longer links that the user perceives, and this perceived safety promotes human friendliness and approachability, which enhances use associated with, for example, the custom poses described below.

In some examples, an outer surface 272 (e.g., metallic, ceramic, or plastic skin) of the arm 204 may cover motors, joints, other components such as wires, control boards, or internal structural components. Motors may be in long links, short links, elbows, or any combination thereof. For example, motors associated with joints may be located in the straight or elbow links and covered with the outer surface 272. The outer surface 272 of the arm 204 may, for example, be made of thin machined aluminum, which optionally may be powder coated. In some examples, an arm may accommodate a visual display or screen, such as an LED display or OLED display, which may be discrete (e.g., see FIGS. 4A-4B) or integrated (e.g., see FIGS. 3A-3C).

Figure 14:
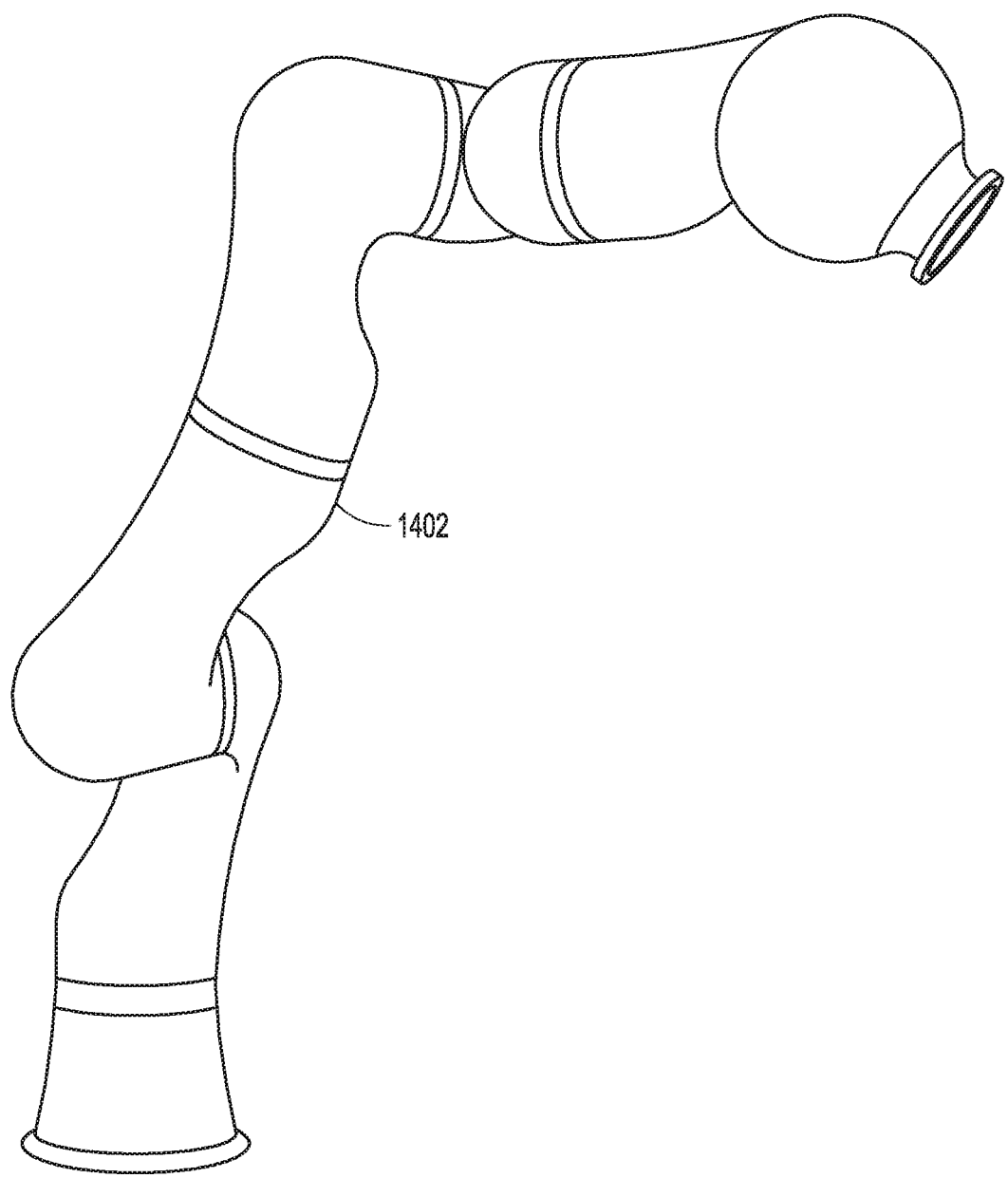
FIG. 14 is an illustration of an example robot arm.
Figure 15:
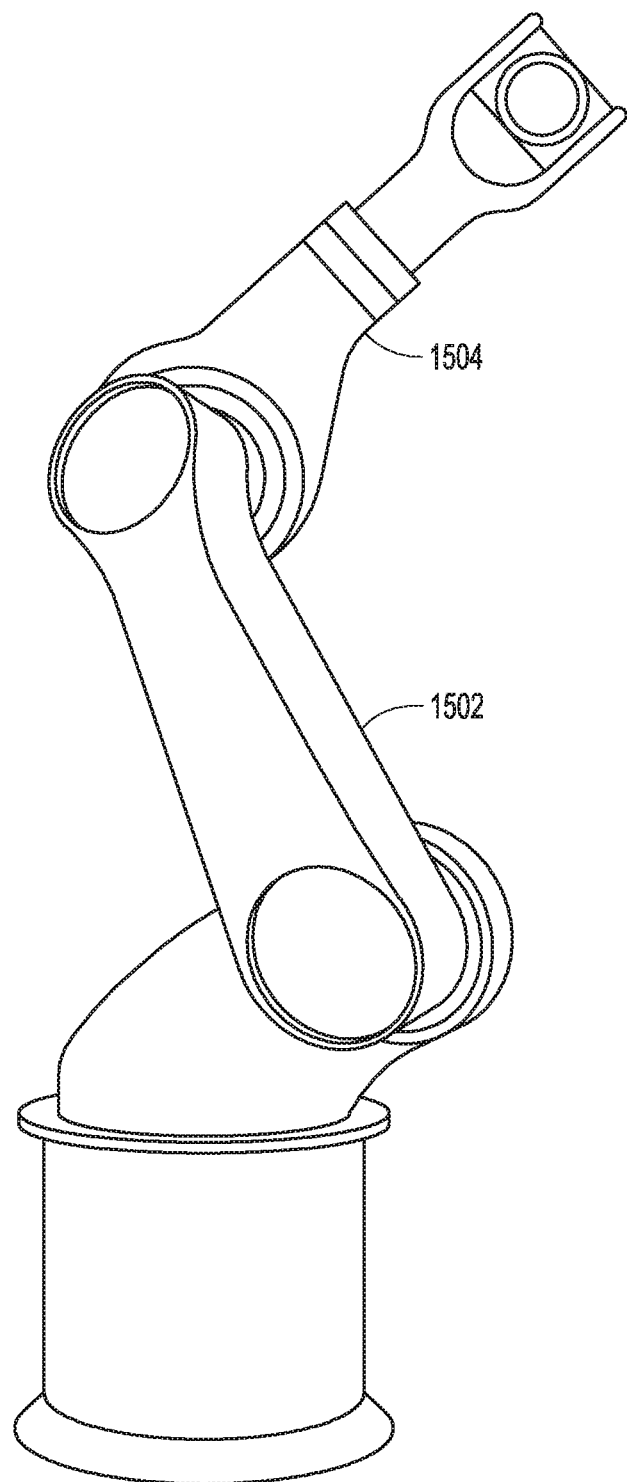
FIG. 15 is an illustration of an example robot arm.

The manipulating system 200 is designed on a human scale, and is designed to incorporate human engineering (human factors; ergonomics) features that promote and guide human interaction, as described above (see section titled Manipulating System Designed on a Human Scale). For example, the system 200 may be primarily white, with polished aluminum (e.g., handle 227 on arm 204 or at helm 213) and grey (e.g., inside of handle 227, foot push pad 205) accents. The eye is then naturally drawn to the accents, and so the user easily identifies operating features or touch points at these locations. The manipulating system 200 may include human-approachable (friendly; non-intimidating; inviting to be touched) design elements such as a human-compatible arm design. For example, the arm 204 or other elements of the system 200 (such as the column 210) may include smooth, even surfaces, and consistent cross-sectional dimensions (e.g., 10-14 cm diameter), which may extend through elbow portions, all of which may indicate safety—even attractiveness to be touched—to a user. In an example, an arm includes consistent cross-sections along a curvilinear axis. The arm 204 may, for example, have no pinch points and no mechanical shearing relationship between links, which may be communicated by the consistent cross section, smooth surfaces, relative configuration of bends, links, or other arm portions. In contrast, FIGS. 14 and 15 are example illustrations of prior art robot arms that are less user-friendly than the example manipulating arms shown in FIGS. 2A-2J and 9A-9C. FIG. 14 shows a system with an arm 1402 that does not have a consistent cross-section and perceived hand/arm/finger pinch and crush points as the links move. FIG. 15 shows a system that has a shear point where a first link 1502 meets a second link 1504, as well as intimidating exposed cables, abrupt edges, potentially injurious exposed nuts and bolts, etc.

The system 200 may include one or more light features, which may be configured or controlled to convey information about the operation or configuration of the system 200 and/or its components. A light feature may be located at a constrained (i.e., a joint) or unconstrained interface between two physical objects. Alternatively, a light feature may be located on a single object, either projecting from, recessed from, or integral with one or more of the object's surfaces, which may be flat, curved, or otherwise shaped or textured. For example, a light feature may extend part way or all of the way around an interface and convey information about the interface. The system 200 shown in FIG. 2A may include a first light feature 236 at the interface (a joint) between the column 210 and the arm 204 (e.g., at the first elbow 218), a second light feature 238 at the interface (a joint) between the first elbow 218 and second elbow 220, a third light feature 240 at the interface (a joint) between the second elbow 220 and the first link 214, and a fourth light feature 242 at the interface (a joint) between the third elbow 228 and the second link 216. A fifth light feature 244 may be provided on the instrument mount (object surface). Additionally or alternatively, light features may also be provided at other locations, such as on the base 202 at an unconstrained interface with the floor (e.g., wheels, roller balls) or with the column 210 (e.g., the curved surface of an integral base and column in FIG. 2A; joint in FIG. 9A).

FIG. 2C is an illustration of a manipulating system 200 positioned over a surgical table 250. The first link 214 and second link 216 have been manipulated to position the instrument mount 208 over a surgical site of a patient 251. The example manipulating system 200 shown in FIG. 2D includes an additional short member 252 between the first elbow 218 and the column 210. FIG. 2C illustrates the minimum impact of an individual system 200's volume at the bedside, which allows clinical personnel to easily access the patient 251 while the system 200 is in use (see the "hybrid" surgery described below), and which allows one or more additional systems 200 to be placed nearby.

Figure 2D:
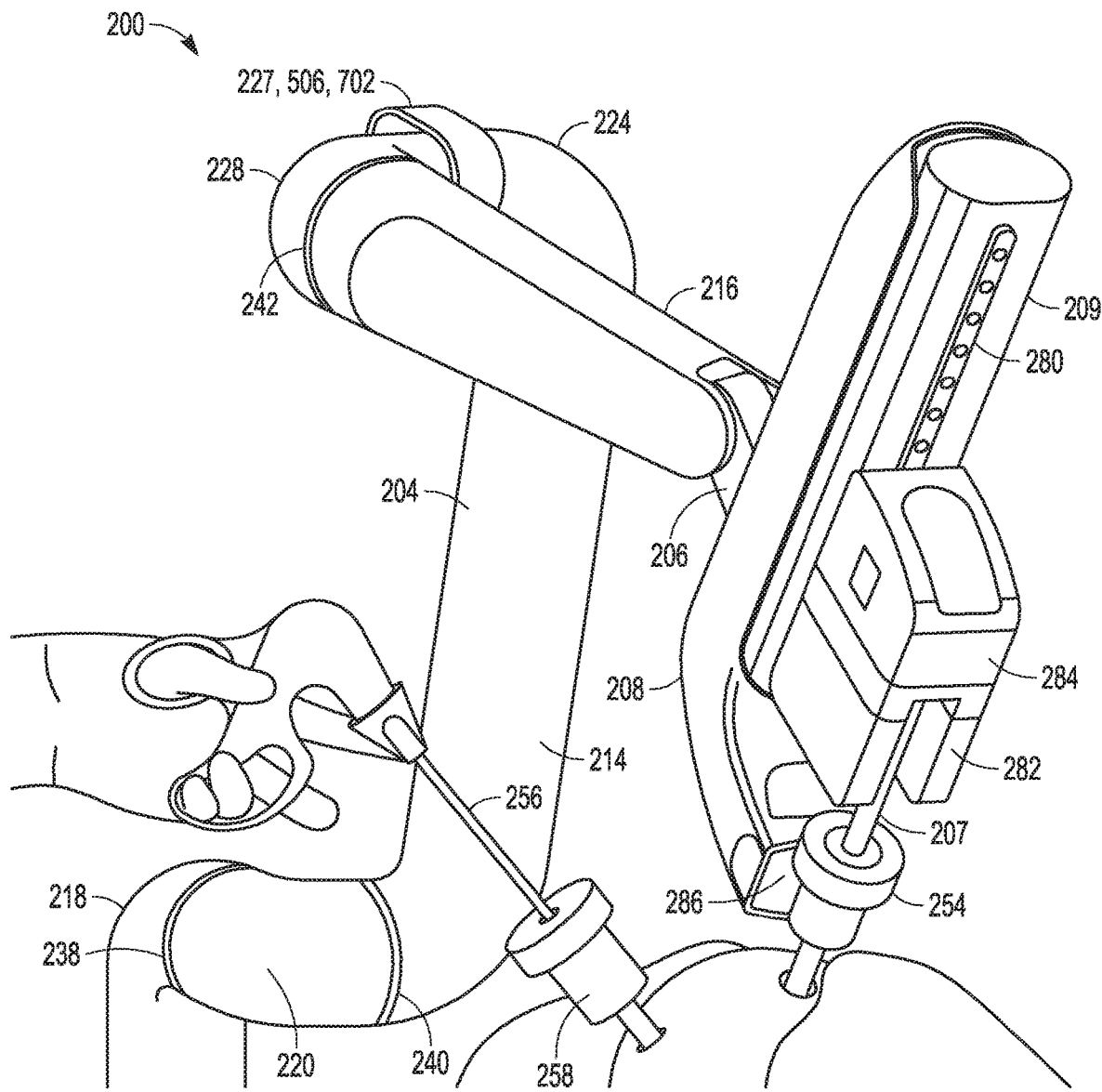
FIG. 2D is an illustration of a manipulating system being used in a surgical procedure.

FIG. 2D is an illustration of a manipulating system 200 being used in a surgical procedure. An instrument carriage 282 may be mounted to a rail 280 on the spar 209. A proximal portion 284 of the instrument 207 may be mounted to the instrument carriage 282. The arm 204 may be oriented and positioned to situate the instrument 207 through a cannula 254 and into a patient. The cannula 254 may be coupled to a cannula mount 286 on the spar 209. The instrument carriage 282 may be translated (e.g., moved up or down) on the rail 280 (e.g., using a lead screw, not shown), which may insert (advance) or retract (withdraw) the instrument 207 with respect to the cannula 254 or patient. The arm links 214, 216 and elbows 218, 220, 228 may be sized, shaped, and configured to position the instrument mount 208 over a subject (e.g., patient) while allowing space for a user to access the subject, as shown in FIG. 2D.

A manipulating system (e.g., system 100 or 200 or 900) may have or use a software-constrained remote center of motion for a surgical instrument. The center of motion may be maintained at least in part by controlling a spar orientation (e.g., orientation of spar 209) with reference to a forearm link (e.g., link 216) as a user (e.g., clinician) operates one or more user inputs on a user control system (e.g., user control system 150).

Figure 2E:
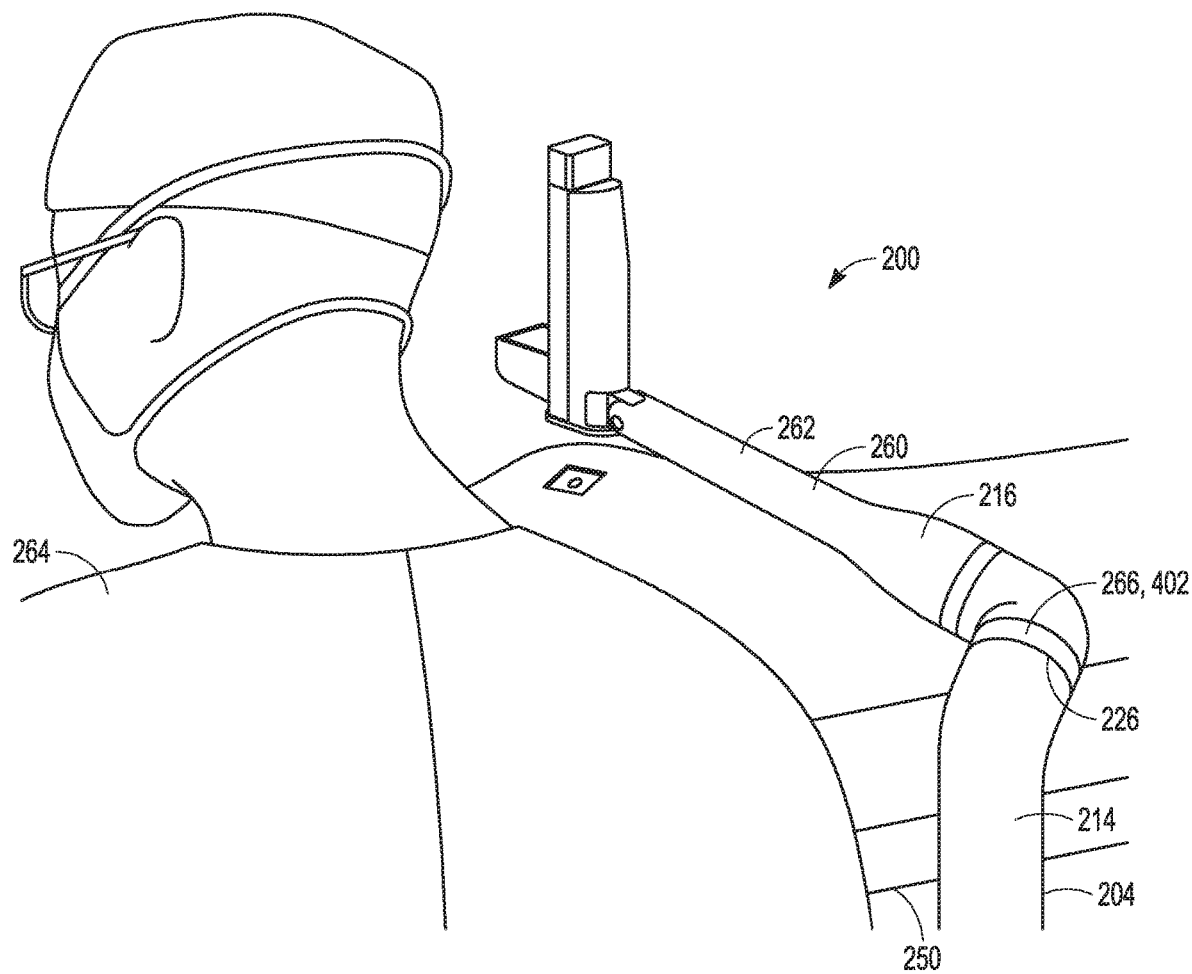
FIG. 2E is an illustration of an arm portion of a manipulating system extending across a surgical table.
Figure 2F:
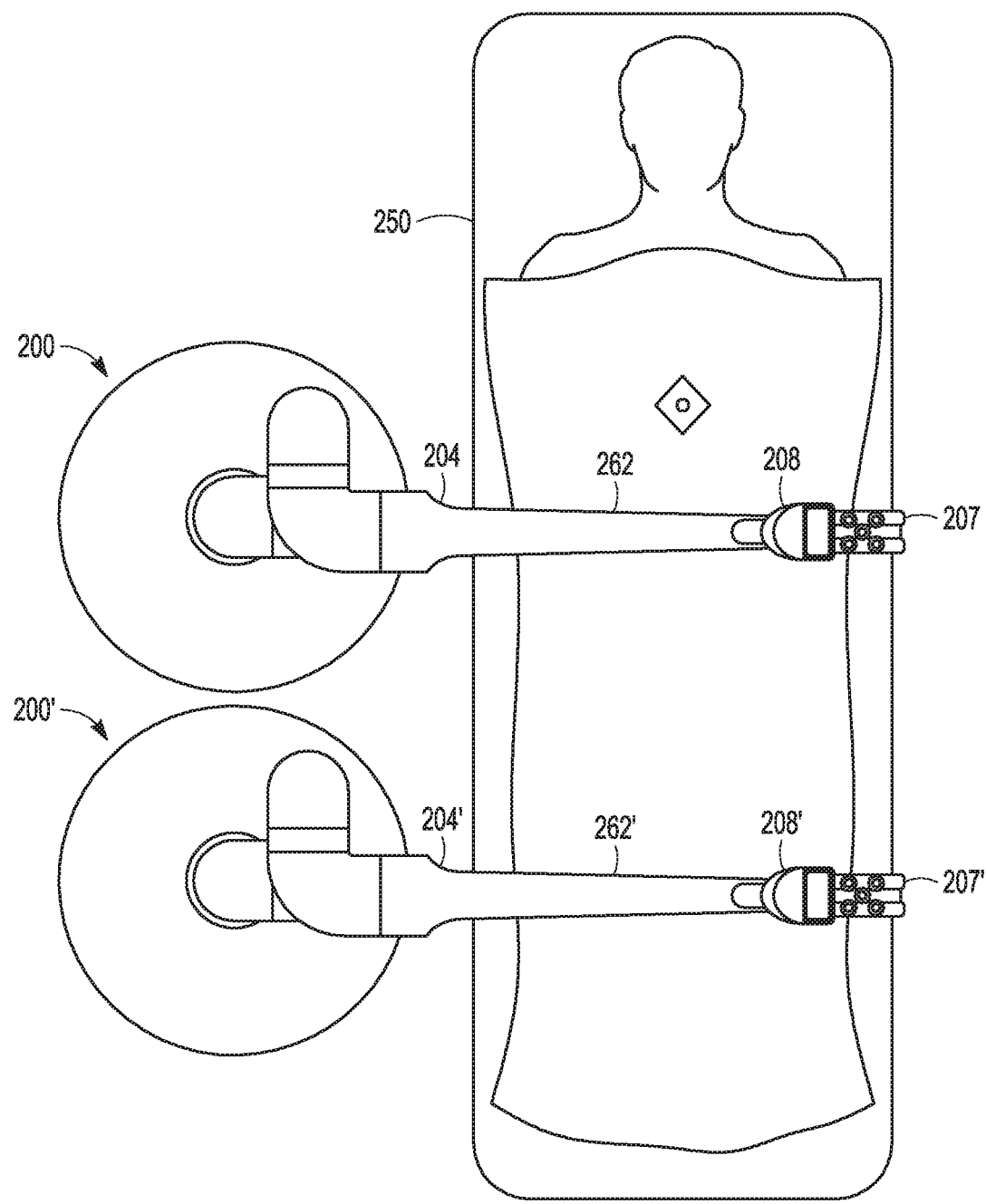
FIG. 2F is an illustration of two manipulating systems positioned side-by-side over a surgical table.

Optionally, a second instrument 256 may be inserted through a second cannula 258 and controlled manually by a clinician (as shown), or it may be controlled by a second manipulating system (e.g., where two systems are positioned at a surgical table as shown in FIGS. 2F and 9C).

As illustrated, therefore, in some examples a manipulating system (e.g., system 100 or 200 or 900) may be used in a "hybrid" minimally-invasive procedure in which a user (e.g., clinician) controls one or more teleoperated instruments 207 (e.g., via a remote control device), and the same user or a different user controls one or more manual instruments 256. In some examples, light features and display features, as described above and below, may contribute to a "user friendly" telesurgical environment, e.g., when the clinician is located next to the teleoperated arm.

FIG. 2E is an illustration of an arm portion of a manipulating system 200 extending across a surgical table. A distal portion 260 of the arm may include a narrowed portion 262 (e.g., may have a tapered or narrowed width or cross-section), which may provide extra operating space for a clinician 264 to work over a patient. The narrowed portion 262 may for example be on a second link 216 of the arm 204. For example, the arm 204 may include a tapered or thinned forearm link that provides improved access (relative to a non-tapered forearm) to a patient (see, e.g., FIGS. 2E, 2F, 9A, 9B, 9C). The narrowed portion or taper on the arm 204 may promote clinical efficacy by allowing better access to the surgical field and to the patient in general. The narrowed portion or taper may provide clinician with more space for hands or tools. The narrowed portion or taper on the arm 204 may also allow a second arm to work more closely without collision. In various examples, a taper on an arm may be abrupt, rapid, gradual, abrupt or rapid and then gradual, or abrupt or rapid, and then straight. The taper may be cross-sectionally symmetric, horizontally symmetric, vertically symmetric, or any combination thereof.

The arm 204 may also include a display 266 (e.g., an OLED display, discussed below), which may be on the short link 226 between the first link 214 and second link 216, or a touch point (also discussed below), which may be on an elbow. The display 266 may be configured to provide information to a user at the table, and the touch point may be configured to receive an input from a user at the table, both of which may promote clinical efficacy by providing information and input options to a user who is working on or near a patient and yet do not interfere with the overall human-engineered form of the arm itself.

In some examples, the base 202 may be powered (e.g., via power supplied to casters 203 or wheels 203' or via power delivered to one or more other objects configured to engage a floor beneath the base 202). The base 202 may be computer-controlled via inputs on the base 202, or it may be controlled using a secondary device (e.g., handheld device), or the base 202 may be teleoperated (e.g., using user control system 150). The base 202 may be controlled (e.g., casters or wheels locked) to be stationary while docked to a cannula (e.g., during a surgical procedure). Alternatively or additionally, the base 202 may move while docked to cannula. For example, the base 202 may move when the system 200 is controlled by inputs from a user control system (e.g., during a following mode). The base 202 may be moved in response to specific inputs from a user to move the base 202, or the base movements may be determined based on a combination of conditions and inputs (e.g., the position of the base 202 may be adjusted to facilitate or enable orientation of a cannula or the arm). Information on movement of the base while docked or during following is found, e.g., in U.S. Patent Application Pub. No. US 2017/0181801 A1 (filed Feb. 15, 2015), which is incorporated herein by reference.

Movement of the base 202 may allow more freedom of movement for system 200 in general, e.g., provide extra range of motion (ROM) for the arm 204. The base 202 may be moved, for example, as an arm 204 approaches end of range of motion.

In some examples, the system 200, or user control system 150, or another device may issue a warning as an arm joint approaches a range of motion limit as the base 202 moves. In some examples, an arm joint may lock as ROM limit occurs as the base 202 moves. For example, the system 200 may lock a joint at or near its ROM limit. In some examples, the system 200 may lock all arm joints as the base 202 moves.

FIG. 2F is an illustration of two manipulating systems 200, 200' positioned side-by-side over a surgical table. The systems 200, 200' may include design features that allow two or more manipulating systems to work and fit closely next to each other. For example, the systems 200, 200' may be sized and shaped to sit side-by-side so that the arms 204, 204' on each system may reach across the surgical table 250 to provide instrument mounts 208, 208' that may be mounted to corresponding surgical instruments 207, 207' for use in a surgical procedure. As shown in FIGS. 2F and 9C, for example, two or more forearms may be positioned close together, which may, for example, allow cannulas to be placed close together.

In some examples, the base 202, 202' of each system 200, 200' may be sized and shaped to allow the systems to be situated close together. Design features to enable side-by-side operation may include for example, a tapered forearm and a small base area, as well as (optionally) a column and an upwardly-extending portion the arm that stay generally within the vertical boundary of the base, with the optional exception of portions that extend over the table. In some examples, the systems 200, 200' may be configured to work side-by-side on the same side of the table (e.g., as shown in FIG. 2F) or on opposite sides of the table (e.g., as shown in FIG. 9C). The systems 200, 200' may include narrowed portions 262, 262' (e.g., forearms), which may allow instruments 207, 207' to be placed close together and give a clinician maximum space to work. In a clinical environment, a sterile drape (not shown) is typically placed over a manipulator arm. In some examples, bases 202, 202' may be sized and shaped to take about the same amount of space as a person standing beside the table.

In some examples, the manipulating systems 200, 200' may be both controlled by the same user control system, such as the user control system 150 shown in FIGS. 1A and 1C. In other examples, each manipulating system 200, 200' may be controlled by a separate user control system, or one or both of the manipulating systems 200, 200' may be controlled by one or more of a user interface, buttons, or tactile response (e.g., applying forces to move the arm) or other control features on one or both of the systems 200, 200'. In some examples, two (or more) units may communicate with each other, e.g., via wireless communication (such as Bluetooth, Zigbee, Z-Wave, Wi-Fi, cameras, acoustic, or light) or wired (e.g., electric, optical) communication.

The portions of bases 202, 202' of the manipulating systems 200, 200' may be sized, shaped, or configured to allow two or more manipulating systems to work and fit closely next to each other (or a close to a person, or other equipment) on the same side of the table, or on opposite sides of a table. In some examples, the base may be asymmetric (e.g., see base 902' in FIGS. 9A-9C). Asymmetry may allow a system to be located closer to the table than if a symmetric base is used. For example, for the same arm geometry, an asymmetrical base may provide a longer reach across the table, e.g., because an asymmetric base may accommodate a larger overhung (cantilever) load, e.g., by providing counterweights in an asymmetric rear portion of the base.

In some examples, a base 202, 202' may be omnidirectional (e.g., see FIGS. 2A, 2B, 2F) so that it is orientation-agnostic for operation. For example, omnidirectionality may permit set-up in any direction. The base may, for example, be symmetric (or nearly so). Portions of a system may be centered around kinematic base (e.g., base of column portion may be centered on the base). In some examples, a base may be circular (see, e.g., FIGS. 2A, 2B, 2F) when viewed from the top, or the base may be a polygon (e.g., a pentagon, hexagon, heptagon, or octagon), or mildly oval, in a way that provides the same benefits as a circular, symmetric base. A base having a combination of circular, polygon, or ovular contour is also possible.

In some examples, the omnidirectionality (e.g., circular, symmetric and/or polygon) of a base avoids forcing clinical personnel to make decisions that trade off benefits and disadvantages of asymmetric bases, such as requiring a cannula be approached from a specific direction, or decisions that bases be placed at certain locations with reference to the patient or the table because of their shape. While the compact circular/symmetric/polygon (or combination thereof) base offers setup advantages, it requires the base to be heavy enough to provide stability, and the increased weight requires more power to drive the cart.

Figure 11:
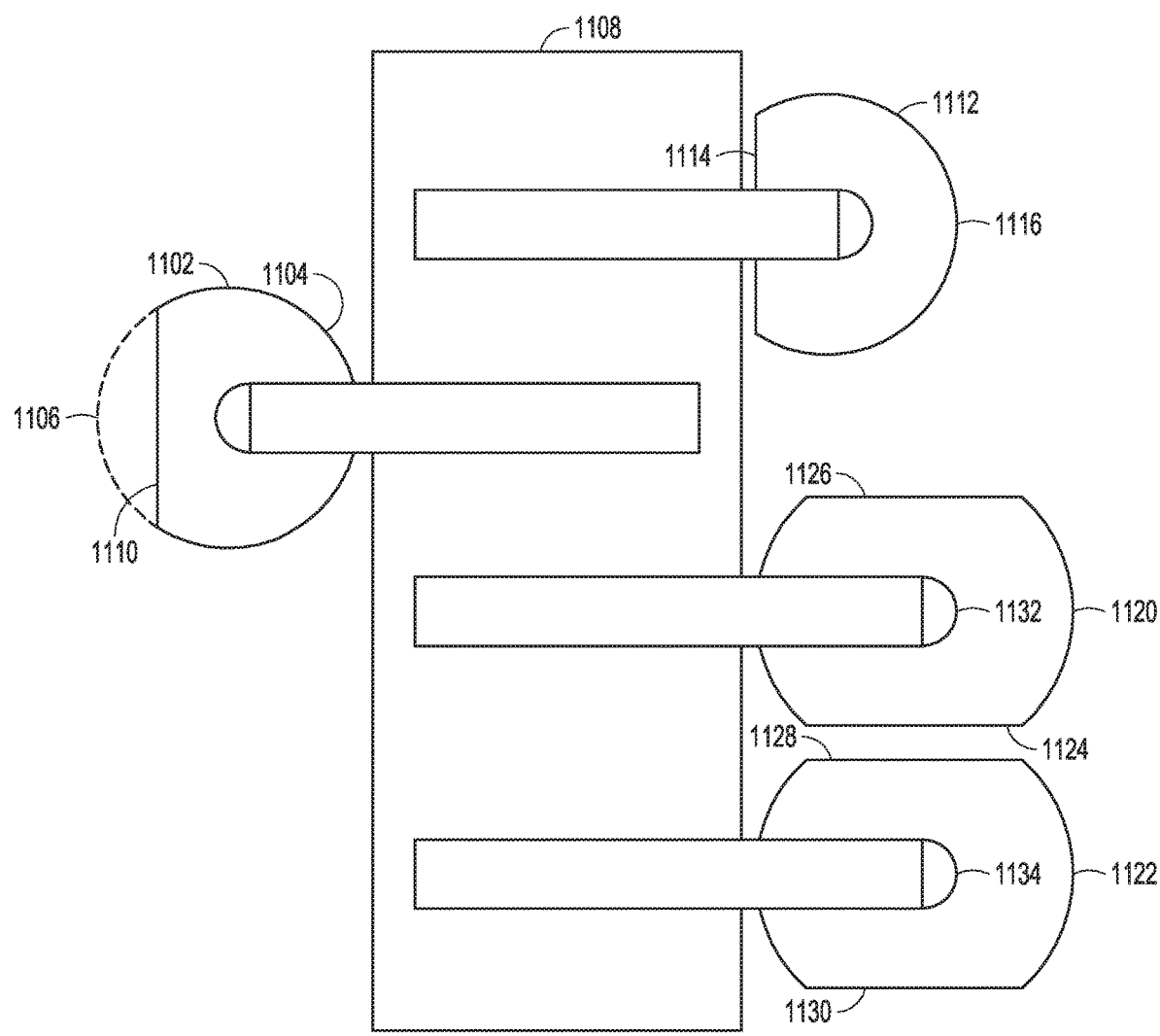
FIG. 11 is a plan view of a surgical theater including a plurality of systems that each has an asymmetric base.

As shown in FIG. 11, in some examples a base may be partially symmetric, but with an asymmetric portion that provides added clearance for personnel or objects. For example, a base 1102 may be circular (as shown) or rounded or polygon-shaped on a side 1104 that faces a table 1108 (e.g., surgical table), with a section 1106 removed on the opposite side 1110 to provide more foot room for a person or clearance for other objects. In another example, a base 1112 may have a side 1114 with a portion removed adjacent to the table 1108 to allow a closer position to the table 1108, and an opposite side 1116 may be circular or rounded or polygon-shaped.

In some examples, a first base 1120 may have a cutout section removed on a first side 1124 (e.g., flat surface) to provide a narrower footprint, and a second base 1122 may have a cutout section removed on a side 1128 (e.g., a flat surface) facing the first side 1124 of the first base 1120, which may enable the two systems to be placed closer together side by side than if the bases 1120, 1122 were symmetrical on adjacent sides of the bases. In some examples a second side 1126 of the first base 1120 and a second side 1130 of the second base 1122 may also include a cutout section, which may allow interchangeability of bases in side-by-side configuration (e.g., in FIG. 11 the bases could be interchanged, i.e. base 1120 may be moved to be closer to the end of the table 1108 and base 1122 may be moved to the other side of base 1120, to be further from the table 1108, and the bases may still be placed so that columns 1132, 1134 are close together as shown). Alternatively, one or both of the non-opposed sides 1126, 1130 of the bases 1120, 1122 may not be cut out, which may provide additional stability due to wider weight distribution or wider support from casters or feet at the bottom of the base.

Predefined Poses

The manipulating system 200 may assume predefined arm poses or motions, which may correspond to different operating modes. For examples, the manipulating system 200 may assume one or more of the predefined kinematic poses shown in FIGS. 2G-2J. The poses may include, for example, factory-defined pose, or a pose that is determined by the system by using one or more inputs and a processor in the system 200 or that is communicatively coupled to the system 200 from outside the system. The poses may also include user-defined poses that may be stored in memory, such as custom poses defined by a clinician or other user. Definition of a pose by a user or automatically by a system may allow for customization of a manipulating system to a particular environment. For example, a pose may be determined based at least in part by a height of a surgical table, a location of one or more objects, or a location of a display on the system to make the display more visible to a user.

In various examples, the predefined poses may be user-modified, or locked, or protected via security feature, such as a password or biometric. For example, movement of a portion of the system (e.g., a link or joint location) may be lockable or unlockable by using a biometric input, such as a fingerprint, retinal scan, voice recognition, or by using a password (typed, written, or spoken), or based upon an interaction with buttons, touch points or other inputs (e.g., a release code may include a combination of inputs).

A pose may indicate to a user when a manipulating system is ready for a function to be performed, and in this way one or more poses establish a visual language communication to the user. For example, when an arm assumes a specific pose, the pose may indicate that the system is ready to perform a function associated with that specific pose, as further described below in reference to the examples shown in FIGS. 2G-2J. The poses act as a visual language interface through kinematic pose to communicate information to a user, such as "I [the system] am ready for you to do task X" or "You [the user] should do task Y now".

Figure 2G:
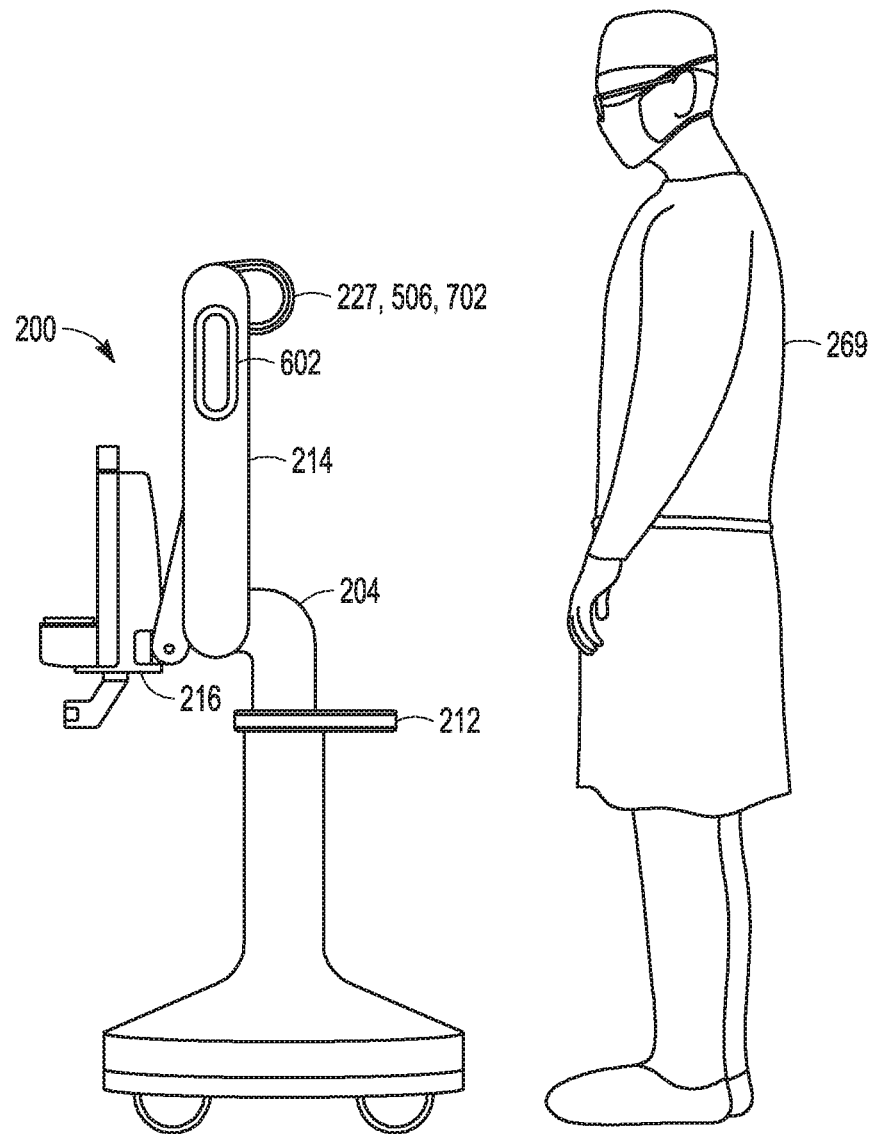
FIG. 2G is an illustration of a manipulating system in an "IV stand" kinematic pose.

FIG. 2G is an illustration of a manipulating system 200 in an "IV stand" kinematic pose. In this position, the manipulating system 200 may be similar to the form factor of an intra-venous (IV) fluid delivery stand, which is typically familiar to clinical staff and may provide a user 269 with a familiar size and shape for physical interaction with the system 200, e.g., for the user 269 to navigate around the system 200, or move the system 200 by grabbing the arm 204. The IV stand pose may provide a compact configuration for transport, or for stowing when the system 200 is not in use. This is another example of human engineering that provides a user-friendly and approachable appearance because it is similar to an object which the user is already familiar and comfortable with. In the IV stand kinematic pose, the first link 214 extends upward, and the second link 216 extends downward, with elbows and interfaces appropriately oriented and positioned to provide the compact form factor shown in FIG. 2G. In some examples, in the IV stand kinematic pose, the arm 204 may be entirely or mostly contained in a vertical space (e.g., vertical cylinder or prism) defined by the shape of the base outer perimeter. A configuration in which the arm 204, or both the arm 204 and the instrument mount 208, is entirely or mostly contained within a vertical space defined by the base 202 may reduce collisions (or the risk of a collision) as the system 200 moves or is moved, because the base 202 will hit a vertical object (e.g., wall) before the arm 204 or instrument mount 208 hits the object. In some examples, two or more arm links may fold back on each other, so that the arm links stow compactly over the base 202. The spar 209 and instrument mount 208 (at the distal end of the arm 204) may be positioned mostly or entirely over the base 202. In some examples, an optional touch sensor on an arm or the base (e.g., foot switch) releases brakes on base wheels to allow the base to move along the floor.

Figure 2H:
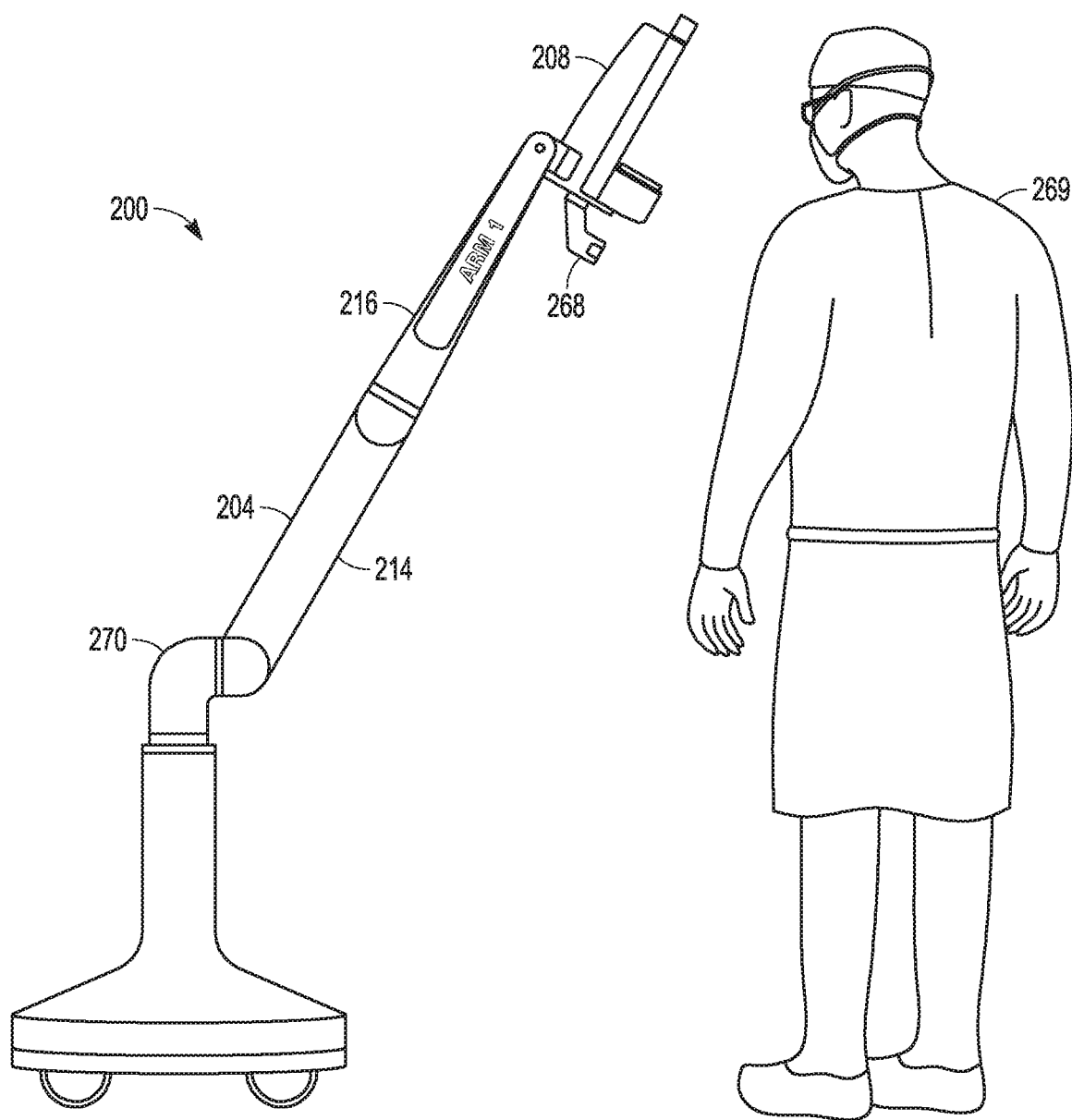
FIG. 2H is an illustration of a manipulating system in a "ready to drape" kinematic pose.

FIG. 2H is an illustration of a manipulating system 200 in a "ready to drape" kinematic pose. The system 200 may show the word "drape" on an indicator (e.g., integrated display or OLED display) when the system 200 is in the drape pose to further communicate the ready-to-drape kinematic state to the user 269.

In response to a drape command or other input or condition, the system 200 may transition to the ready-to-drape pose, i.e., extend an arm for easy draping (covering portions of the system 200 with a sterile drape) by a user. For example, to facilitate draping, the system 200 may move the distal end of the arm or a drape mount 268 to a point high enough to preserve sterility (e.g., so that the drape does not fall below the lower boundary of a defined sterile field, such as the surgical table top if the area below the table is not part of the sterile field) and yet low enough to allow the user to reach and drape the arm. In an example, in the ready-to-drape pose the arm 204 may be oriented and positioned to place the distal end of the arm 204 or a drape mount 268 at an appropriate height so that a user 269 may reach the drape mount 268 to couple a surgical drape to the drape mount 268. In the example shown in FIG. 2H, the arm 204 is positioned and oriented so that the first link 214 and second link 216 are coaxially aligned and extending upward at an angle less than 90 degrees to present the distal end of the arm or the drape mount 268 at an appropriate height for draping with a sterile drape. Likewise, the instrument mount 208 may be generally coaxially aligned with the first link 214 or with both the first and second links 214, 216 in order to facilitate easy draping with a sterile drape.

In some examples, the system 200 may lock all the joints in the ready-to-drape mode, or the system 200 may lock all joints except one, such as shoulder joint 270 at the top of the column 210 to enable arm height adjustment. In some examples, the free (not locked) joint is gravity-compensated to allow user 269 to easily adjust height. In gravity compensation, one or more motors or springs counteract gravity forces while the arm 204 is either stationary or moved by hand so that the arm 204 acts as if weightless. In some examples, the free joint may be braked (automatically or in response to user input) to hold the desired pose after the height adjustment. In some examples, a system may lock all joints except a lower shoulder joint 270 and allow a user to move the arm 204 vertically down for draping, and the system may then optionally return the arm to a previous higher vertical position after a drape is coupled to the drape mount as determined by a sensor or user input.

The system 200 may accommodate different user heights. For example, the arm 204 or drape mount 268 may be positionable higher or lower to enable convenient reach by a user.

In some examples, the system 200 may, automatically or through a guided process, assume a specific (e.g., personalized or predefined) drape kinematic pose or drape height for an individual user, e.g. a pose based on a stored user height, stored user preference, or sensed user information. The system 200 may, for example, recognize the height of the user, e.g., using visual scanning camera, pre-stored or one-time entered height information. In some examples, the system 200 may learn a comfort height for an individual user, store the height, and then move to the user's comfort height the next time the individual user commands the ready to drape pose. As a further example, the system 200 operated by a first user extends the arm to a first ready to drape pose customized for or preferred by the first user, and the system 200 operated by a second user extends the arm to a second ready to drape pose customized for or preferred by the second user.

In some examples, the system 200 may assume different arm positions (e.g., angle with reference to the floor) for the drape pose based on a position of the handle 227 or helm 213 (both shown in FIGS. 2A and 2B). For example, rotating the handle 227 or helm 213 upward with respect to the column 210 or arm 204 may correspond to a higher drape position, and rotation of the handle 227 or helm 213 downward may correspond to a lower drape position.

In some examples, the system 200 may determine a push configuration based on the arm pose that was used during transport (either the IV pose described above or the transport pose described below) or on a handle or helm position used during transport, and then determine a drape pose based on the push configuration. For example, the system 200 may determine a height parameter of a person who moves the system 200 in the transport pose. If a relatively tall person moves the unit in the transport pose, the system 200 may subsequently move the drape mount to a relatively higher height (e.g., configure the arm higher), and if a relatively short person moves the unit in the transport pose, the system 200 may subsequently move the drape mount to a relatively lower height (e.g., configure the arm so the distal end of the arm or the drape mount 268 is lower). In some examples, a feature that determines a ready to drape pose height based on a prior interaction (such as transport) may have a time-out, so that the feature is applied only if the ready to drape pose is commanded within a predefined time (e.g., 10 minutes) or other limit (e.g., system has not been placed in standby) after the prior interaction (e.g., after moving in the transport pose).

Figure 2I:
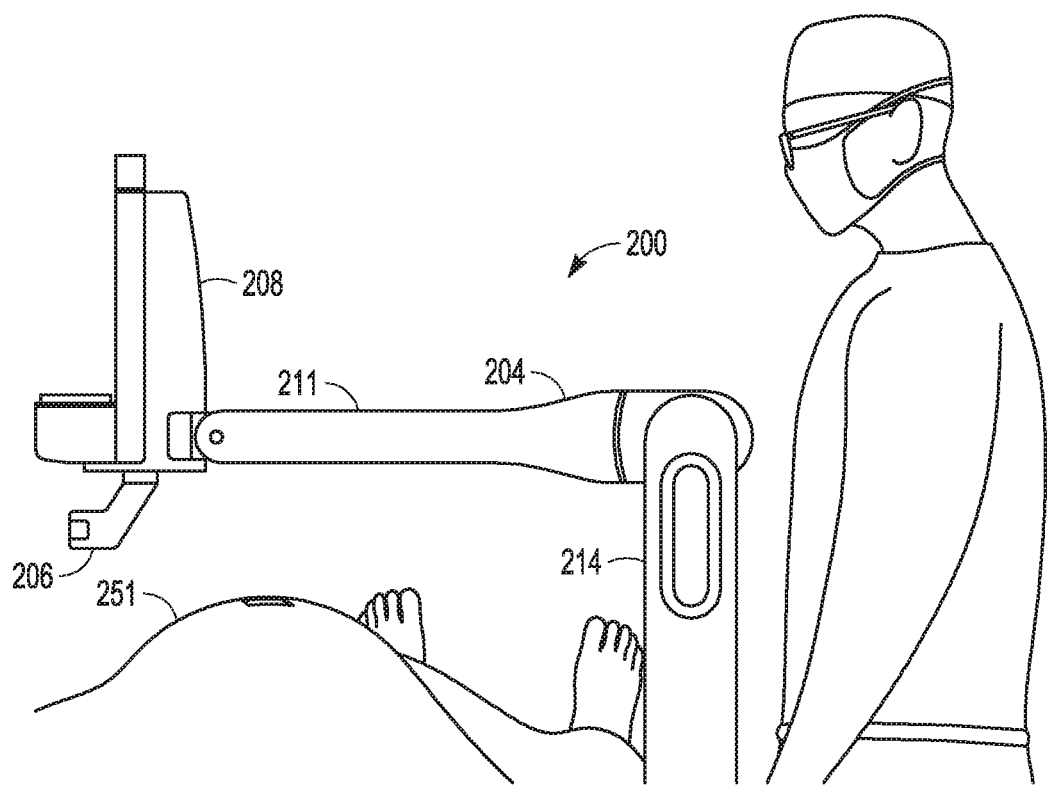
FIG. 2I is an illustration of a manipulating system in a "ready to dock" kinematic pose.

FIG. 2I is an illustration of a manipulating system 200 in a "ready to dock" kinematic pose. An indicator (e.g., integrated display or OLED display) may show the words "ready to dock" or a corresponding symbol or indication when the system 200 is in the ready to dock pose to further communicate the ready to dock kinematic state to the user. Alternatively, an indicator such as "standby" may be similarly communicated when the system 200 is not ready to dock. The "ready to dock" pose may be used when the system 200 is deployed for entry into a sterile surgical field and subsequent docking to a cannula inserted into a patient on a surgical table. For example, in the ready to dock pose, when the system 200 is adjacent a surgical table, the arm 204 may extend over the surgical table to position the instrument mount 208 above a surgical site of a patient 251 as shown. In the ready to dock pose, the forearm may be generally horizontal. As described above with respect to the ready to drape pose, the system 200 may lock some or all but one of the joints and enable a user to manipulate one or more joints to move the forearm or instrument mount 208 to a user-determined height, e.g., to position the forearm above a surgical site on a patient 251 on a table in order to effectively dock to the cannula, or position the instrument 207 for use, to provide the desired instrument range of motion during surgery. The system 200 may compensate for gravity or provide assisted moving as described above, and it may lock joints after expiration of a period of time or in response to a user command.

Figure 2J:
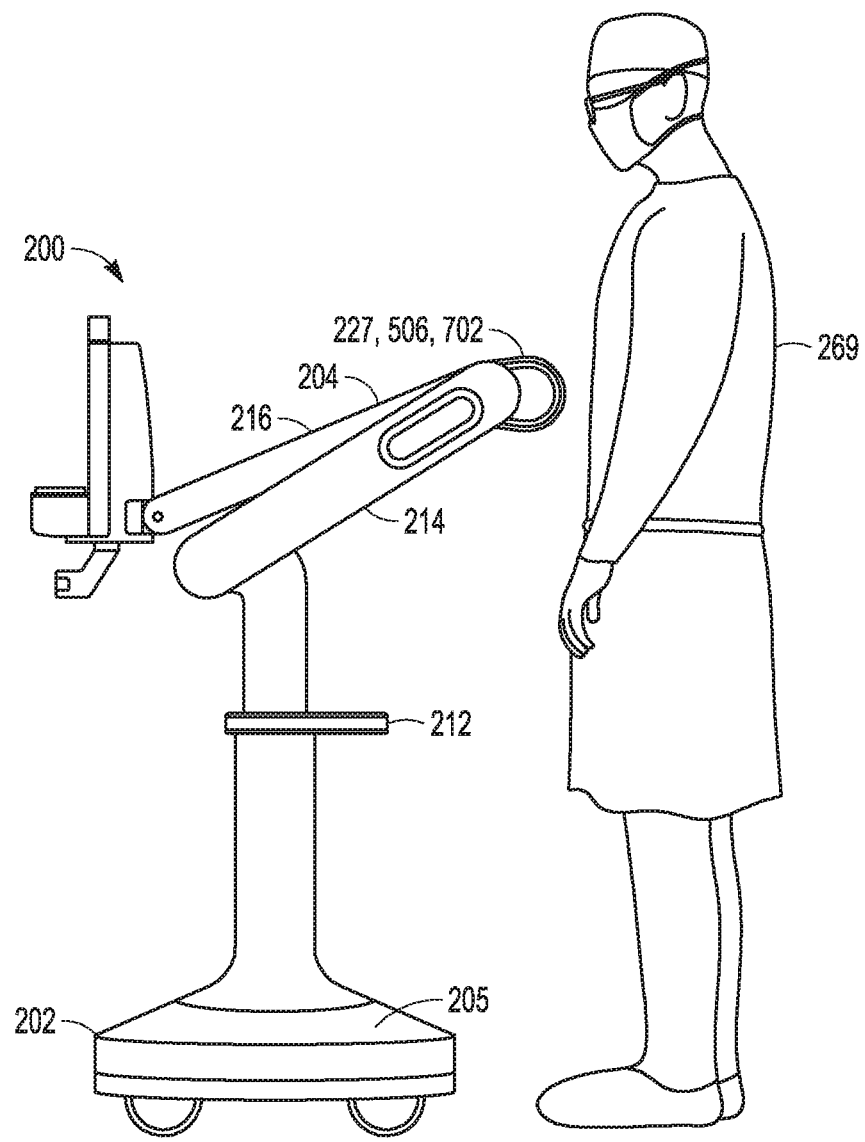
FIG. 2J is an illustration in a "ready to transport" kinematic pose.

FIG. 2J is an illustration of a "ready to transport" or "transport" kinematic pose. An indicator (e.g., integrated display or OLED display) may show the words "ready to transport" or a corresponding symbol or indication when the system is in the ready to dock pose to further communicate the system state to the user. Alternatively, an indicator such as "standby" may be displayed to the user to indicate the system is not in the "ready to transport" or "transport" state. In the description that follows, the "ready to transport" pose as described also applies to the "transport" pose used for moving the system.

In the ready to transport pose, the arm may be placed in an pose that facilitates easy transport of the system 200. For example, the arm 204 may be positioned and oriented to provide the user 269 with a convenient push point or push pad 205 for transporting the manipulating system 200 by pushing it. For example, in the transport pose, the arm 204 may extend at least partially back and present an arm, elbow, or handle to provide a convenient grab point or hand push point. In some examples, the system 200 may be pushed like a shopping cart by using the extended arm or elbow or handle.

In some examples, two or more arm links may fold back on each other, so that the arm links stow compactly over the base 202. The upper arm link may extend past the proximal end of the lower arm link, which may position the spar 209 and instrument mount 208 (at the distal end of the upper arm link) on the other side (relative to the column 210) of the location where the lower arm link proximal end joins to the vertical column link.

In some examples, the grab point or hand push point may be outside the vertical boundary of the perimeter of the base to provide clearance for the user's feet while walking. Even though the push or grab point is outside the vertical boundary of the base, the system 200 may still be in a relatively compact configuration, for example with most of arm within the vertical boundary of the base, and a push portion extending outside of the boundary. In this way many of the advantages of keeping the arm within the base's vertical boundary are preserved, and a small exception is made so that the user is provided a comfortable touch point for moving the system. In one example use, a user places the system in the transport mode to move it relatively longer distances (e.g., down hallways and through doors) and places the system in the IV mode to move it relatively shorter distances when obstacle clearance is most important (e.g., near a patient operating table).

In an example, the first arm link 214 may be positioned and oriented to extend back toward the user 269, and the second arm link 216 may be positioned and oriented to extend forward to provide a compact transport form factor, while also providing a grab or hand push point. As shown, the grab or hand push point is at the interface between first arm link 214 and second arm link 216, at elbows/bends at this location, optionally separated by a short link as described above or a handle as described below. The rest of the arm and instrument mount remain within the vertical boundary of the base, which may be of various shapes as described.

In some examples, the height of the grab or push point may be adjustable, with motion assist or gravity compensation, as describe above in reference to the ready to drape pose. In an example that includes a handle 227, as shown in FIGS. 2A and 2B, the orientation of the handle 227 may be adjustable and lockable by the user, or it may be automatically lockable (e.g., after expiration of a predefined time period with no movement) as described above. In some examples, motorized wheels or roller balls in the base 202 may assist with transport, as described above.

Various command schemes may be used to manipulate a system into a pose. For example, a system may assume a pose using an automatic process (e.g., automatic posing), or a system may assume a pose using a step-by-step guided process, or system may assume a pose using a manually-assisted process. A manipulating system may be configured to automatically assume a pose, for example, based at least in part on a receipt of a command from a user interface or buttons on the system, or based on a receipt of a command from a separate user control system. In a commanded posing process, a manipulating system may move into a pose in response to a user command (e.g., via a user control system, buttons, screen interaction, or voice command). In an example guided process, a user may manually move the arm into a pose through one or more guided steps. In a guided process, a system may present guidance to a user by using audible word commands (e.g., presented on a display or played through a speaker), or by using visible light feature indications (e.g., a light feature at a joint to be lighted, or may be lighted in a manner that indicates a direction of movement), or by using a combination of audible word commands and visible light feature indications (e.g., "Straighten the elbow joint, which is flashing blue"). A system may also assume a pose through an unguided process. For example, a user may manipulate the system into a pose. In some examples, a system may apply fuzzy logic, e.g., when a system is manipulated into a configuration that approximates or resembles a pose (e.g., joints are within a specified amount, e.g., 5 degrees or 10 degrees of a certain pose), the system may automatically, or in response to a user input or to a user query response, move the rest of the way into the pose (i.e., the system predicts the user's intended pose, and then implements the pose). In some examples, a system may guide a user to a pose by limiting one or more of available degrees of freedom (e.g., mobility of joints) to lead the user through steps that progress toward a pose. In some examples, a manipulating system may assume a pose based upon satisfaction of a condition (e.g., no instrument docked and user control system indicates ready for docking). For example, responsive to satisfaction of a condition, a system may automatically assume a pose, or it may output a query to a user regarding a pose (e.g., "Assume dock pose now?").

Commands may be received, for example, via a manual input device, voice command, or electronic command from another device (e.g., from control console, remote control, or other handheld device). Manual input devices may include one or more buttons, force-sensitive areas, touch screens, or tablet controllers, any of which may be coupled to or separate from the unit (e.g., handheld), and which may communicate with motors or a controller via wired or wireless communication technology. Manual input devices may, for example, be on the helm or on one or more arms, elbows, or handles. In some examples, translation to a pose may be initiated by touching the arm at one or more key points (e.g., force sensors or buttons), or translation to a pose may be initiated by pulling or pushing near a joint or at a handle. In some examples, movement of links or joint positions may be limited to specified directions or ranges of motion, e.g., to assure progress toward a specified pose.

In some examples, commands may be received through a gesture sensing device (e.g., Leap® controller by Leap Motion, Inc., San Francisco, Calif.). In some examples, a user's gesture may indicate a direction or nature of movement. For example, a predetermined user gesture may correspond to a specific action, position, orientation, or pose of the system or a system component. In some examples, a user may draw a shape in the air, and the manipulating system may move into the drawn shape, or a shape interpreted from the drawn shape as described above.

In some examples, one or more commands may be received using an augmented reality device or feature. For example, a system may include or receive input from a software widget that may be manipulated by a user.

In some examples, a manipulating system may include one or more force sensors for receiving input. Force sensors may, for examples, include capacitive sensors or pressure sensitive sensors. In some examples, a sensor or sensor system may be both capacitive, to confirm that a person is interacting with the sensor, and pressure sensitive to receive information that constitutes a command.

In some examples, the manipulating system may apply logic or an algorithm to the receipt or execution of a command. For example, a movement command may be available and active at a specified time or in a specified condition, e.g., during a sequence, or when a particular mode is enabled. In some examples, a system may require two or more sequential or simultaneous inputs to verify intent to deliver a command. For example, a system may require two hands on the machine, or two persons interacting, a restriction which may for example avoid interpretation of an inadvertent touch or force event (e.g., leaning on a system or brushing past a system) as a command, i.e., application of logic requiring a combination of two or more commands may avoid a risk of an inadvertent bump that triggers a movement. In some examples, to effectuate a command a system may require a first input to initiate a command receiving mode and a second input that includes the actual command. In some examples, a system may require two types of inputs, e.g., voice and a button.

In some examples, features on or associated with a manipulated system, such as one or more lighted rings or displays, may indicate which links to move or joint positions to change, or where on the links or joints to impart movement, or the direction or type or sequence of movement. For example, a particular light feature (e.g., light ring) may light up to indicate that a joint position should be changed, and an aspect of the light feature, such as a lit portion or an animation, may indicate a direction of movement (e.g., to indicate to change a linear or rotational joint position in a particular direction as indicated by an animation that may extend along or around the joint).

As mentioned above, in some examples, a manipulating system may apply context-aware or predictive functionality. For example, an operation may be enabled based at least in part on context. In some examples, a system may predict a desired operation (e.g., movement into a particular kinematic pose) based on one or more inputs, software, or application of inputs to a model. Inputs for context-aware or predictive functionality may, for example, include the current pose of the unit, a dock state, button or switch activation, actuation or state of a break-away clutch feature (e.g., a state of a button or switch that when activated releases a brake and allows an arm or joint to move). In some examples, a system context-aware or predictive functionality may determine availability of kinematic null state adjustment (option for manual adjustment of one portion of the unit without moving another portion of the unit, e.g., lock instrument and mounting components but allow some movement of arms or joints), or be based at least in part upon an availability of a kinematic null state adjustment (e.g., null state availability may form part of condition).

In some examples, the system in a particular pose may indicate that it is in a corresponding mode of operation. For example, the functionality of a manipulating system, software algorithms, responses to input, mobility of arms or joints or base, handle position, or lighting behavior may vary as a function of the assumed pose.

In some examples, a particular pose or system state may be indicated or identified by lighting on rings, or by a presentation on an integrated display that appears to disappear when not active, or both. For example, a color, or flashing lights, or animation, or other waveform may indicate that a pose or system state has been achieved or assumed, or is active. In some examples, a color or combination of colors may be associated with a particular pose. In some examples, a pose may be indicated or identified by sound (audible) output. For example, a system may generate a sound, such as a chime or ascending tone sound, when a unit has assumed one of the poses. In some examples, a system may generate a different sound for each pose. In some examples, a system may generate a sound (e.g., descending tone sound) when a unit has left a pose. Or, a system may generate a particular sound when a pose cannot be achieved, for example because of an obstruction or a configuration issue such as a joint ROM limit. In some examples, a pose, mode, or other state may be indicated by sound and light outputs together in order to particularly draw a user's attention to the system's communication.

In some examples, a system may perform an automatic docking procedure in which a manipulator arm is docked to a cannula that is inserted into a patient. For example, a system control base first motors to move and approach a destination (e.g., a position adjacent a surgical table). In an example, the system may enter a compact pose (e.g., IV stand pose or other pose with an arm retracted) for this approach step to reduce the potential for a collision during the approach, and then the system extends the arm at the end of the approach to another pose, such as a ready to dock pose. In another example, a system may first move into a ready to dock pose and then move approach the destination, optionally making adjustments during the approach to avoid a collision or to assure proper clearance from operating room obstacles. In some examples, a system may "roll up" to a surgical table after it has been placed, or placed itself, into a ready position or orientation (e.g., ready to dock pose). The system may process sensor input (e.g., motion sensors or force sensors) to avoid collisions, or to preserve or obtain proper space or clearance with other objects. In some examples, a system may return to a defined home location, e.g., in response to a discrete "home" command or in response to completion of a procedure, such as when the arm is undocked from a cannula and is moved to an IV stand pose.

Displays

Figure 3A:
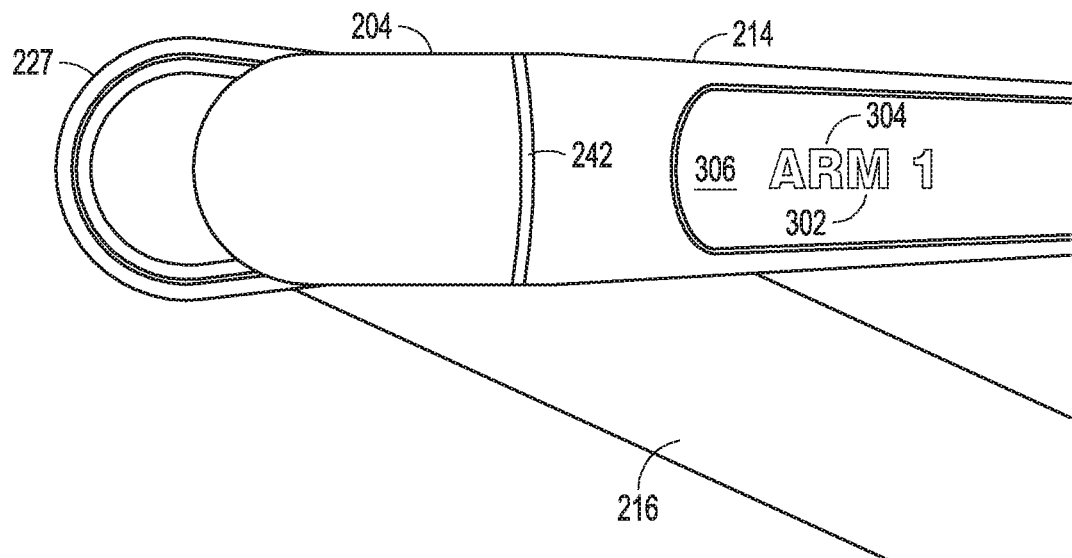
FIG. 3A is an illustration of an integrated display on an arm portion of a manipulating system.

FIG. 3A is an illustration of an integral display 302 on an arm portion of a manipulating system. The integral display 302 may be provided on a portion of the manipulating system 200 shown in FIGS. 2A-2J, as illustrated in FIG. 3A. The integral display 302 may also be provided on an arm of the system 100 shown in FIG. 1B.

In FIGS. 2A, 2B, 2D, and 2H, the integral display is shown located on the arm 204 (e.g., on the second arm link 216), but the integral display 302 may be anywhere on the device (e.g., on the column, the base, on an elbow, on any arm or link, or between major links or arms), and a system may include two, three, or more integral displays, which may each show the same information, or which may work in concert to each show different information, which may for example, be relevant to a particular part of the system (e.g., relevant to a particular arm link or relevant to an instrument associated with an arm) or relevant to a viewer having a particular perspective (e.g., field of view). The position of the integral display 302 is only limited by space to mount a display device, such as an LED display, which may, for example, be mounted in an internal space inside the arm 204.

In some examples, the integral display 302 in the arm 204 may be a continuation of the surface contour of the portion of the arm 204 (e.g., arm link) in which the display 302 is located. And in some examples the integral display 302 may "disappear" or become "invisible" (i.e., not easily perceived as being a display) when the display 302 is not outputting information to the user. The ability of the display 302 to "disappear" into the arm 204 may provide a cleaner user experience (relative to a display that does not disappear), and it further enhances the human-engineered, user-friendly, ergonomic, and approachable character of the arm 204. For example, the display 302 may appear to exist and output information when the display 302 is needed, and the display 302 then appears to not exist when the display 302 is not needed and no information is output. In some examples, the system may provide a relevance-based display, which may be visually present only during the time the displayed information is relevant. In this manner, the display (i.e., the manipulating system) may provide a user with only the information the user needs or wants at a particular time and at a location relevant to the user. The capability of a display to disappear when not needed also avoids taking up visual real estate on the arm or avoid the visual "noise" or clutter of a permanently visible screen, which may provide for a better user experience by only being present when the user needs it and otherwise not visually distracting the user.

An integral display 302 may be formed in the surface of the arm 204, as shown in FIG. 3A. For example, a grid of very small holes 304 may be formed in the aluminum surface 306. A hydrojet process, for example, may be employed to form the grid of holes 304. The hydrojet-formed holes (or other types of holes) may be small and practically not visible to the naked eye, but they may allow light to pass through so that the light is visible to a viewer of the display 302. In some examples, an LED panel (not shown) may be installed behind the grid of holes 304. A display on the outside of the surface 306 may be created when light from the LED panel shines through the holes. Portions of the LED panel may be controlled to be lit or dark to form any desired pattern, such as a word, picture, symbol, animation, or other display of information. The holes may be formed to be subtle or invisible to the eye when LED is off, so that the display effectively "disappears" when it is not outputting information. In this way a light pattern is transmitted through the grid of holes 304 to be visible to the user, and the surface 306 otherwise appears blank when no light pattern is transmitted through the holes. Alternatively, other display surfaces may have identical or nearly identical surface quality as the arm so that the display effectively "disappears" when it is not outputting information. The display material may be visibly blended with the surrounding structural surface so there is no perceivable visual break between the surface and the display. In some examples, the material may blend or hide a material transition in a way that two materials (e.g., finished metal and plastic) have a visually identical surface character. Thus, in various ways the entire arm or other system component or portion itself appears to be the display in order to more effectively communicate information to the user within the overall human-engineered appearance of the system.

Figure 3B:
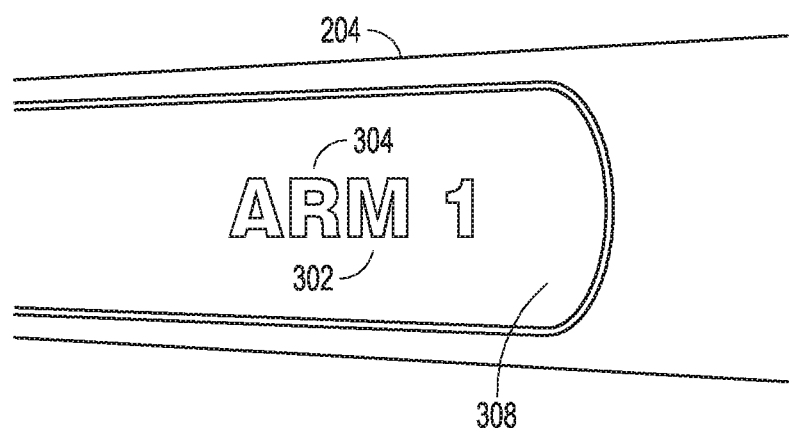
FIG. 3B is an illustration of an integrated display on an arm portion of a manipulating system.

As shown in FIG. 3B, in some examples, an integral display 302 may be formed in or of a different piece of material 308 and integrated into the arm 204 to be continuous with the arm's surface. The piece of material may be integrated in a way such that the panel of the display 302 is visibly distinct from the piece in which it is located (e.g., a different color or texture, or a clear dividing line between structural surface and display), or subtly different from the piece in which it is located (e.g., the same color, but with a barely visible join line). In some examples, the integral display 302 may be visibly defined. For examples, the display 302 may include a black display area on a white arm (see, e.g., FIGS. 4A-AB).

An integrated panel may be plastic, metal, ceramic, or other material. As described above, a grid of holes 304 may be formed in the material 308. Alternatively or additionally, the material 308 may be translucent (light-conducting) or transparent so that it can conduct light from light source (e.g., LED) behind a plastic panel to present information to a viewer of the panel. In some examples, an integrated panel may be formed from light-conducting Conan® material from Dupont™. In some examples, the integrated panel may be transparent, similar to recent television display technology development by Panasonic Corporation (e.g., transparent OLED display).

The integral display 302 (and any other displays) may be configured to be readable through a transparent sterile drape that covers the link in which the display is mounted. And, an integral disappearing or panel display may be placed on an area that protrudes from or is recessed into the surface of a system component so that the protruding or recessed area is visually prominent regardless of information being displayed. The protruding or recessed area may form part of the overall visual human-engineered design and extend beyond the boundary of the integral display feature.

Controllable Displays

In various examples, a display on an arm or other aspect of a system may be controlled (e.g., by a direct input or via another system or device (system 100, system 200, user control system 150, processing system 180, etc.) to present information such as words, symbols, or other indicia to facilitate user interaction or understanding during a procedure. A controllable display may, for example, be an integral display 302 as described above.

Animations may be implemented on a controllable display, which may be the integral display 302 (e.g., disappearing display or integrated panel), by controlling light behavior. For example, an animation may display linear or curvilinear motion, such as an arrow moving in a pointing direction. An animation may display angular motion, such as indicating a direction to change a kinematic pair angle (e.g., to move a joint or adjust the position of a link or elbow with respect to an adjacent link or elbow). An animation may display size change, such as an expanding or contracting circle or disk. An animation may include color changes, such as changing between red and yellow, or red, yellow, and green, and such color changes may be dynamically linked to a system or component state, such as gradually changing color as a particular link pose is approached. An animation may include text, such as scrolling horizontally or vertically, or zooming in or out, or gradually appearing or fading away. An animation may include morphing, such as changing from one shape or icon to another, changing from text to a shape or icon, changing from a shape or icon to text. An animation may include a combination of any two or more of the animation features listed above. And persons skilled in the art of animation user interfaces will be familiar with various other animation forms that may be used.

An animation presented on a controllable display is designed to be relevant to the clinical operation of a manipulator system or a manipulator system component. The controllable displays that display the animations are located where they can be easily seen by a clinician who is carrying out the relevant clinical operation. As an example, a linear or curvilinear motion animation display may indicate a suggested, optional, or required direction of movement for a movable system link or other component. As another example, an animation color change may be dynamically linked to a system or component state, such as a gradually changing color as a particular link pose is approached (e.g., centered in a joint ROM, or approaching a joint ROM limit). As another example, a manipulator system arm has two, three, or more controllable displays located at various combinations of arm links or joints, and animations on the controllable displays indicate to a user how best to position the arm links by displaying a first animated movement indicator in one color (e.g., red) when a component is not in a desired position or orientation, then displaying the animated movement indicator in a second color or color hue (e.g., yellow or green; lighter red hue) as the component approaches the desired position or orientation, and then displaying either a second animated indicator or a static indicator (optionally morphed from the first animated indicator) in the second color or color hue, or in a third color or color hue, when the component is at the desired position or orientation. As another example, such an animation scheme may be used to guide a clinical user to position the manipulator system from a first predefined pose (e.g., the IV stand pose or the transport pose) to a second predefined pose (e.g., the ready to drape pose or the ready to dock pose). As another example, an animated display at a location on the manipulator system indicates that a component should be coupled to or decoupled from the system at that location, and the animated display changes to indicate the component's coupled or decoupled state. As another example, an animated display that indicates the component's coupled or decoupled state further indicates the state of the connection i.e., not simply physically connected but functionally connected as indicated by a sensor or self-test feature associated with the connection.

Figure 3C:
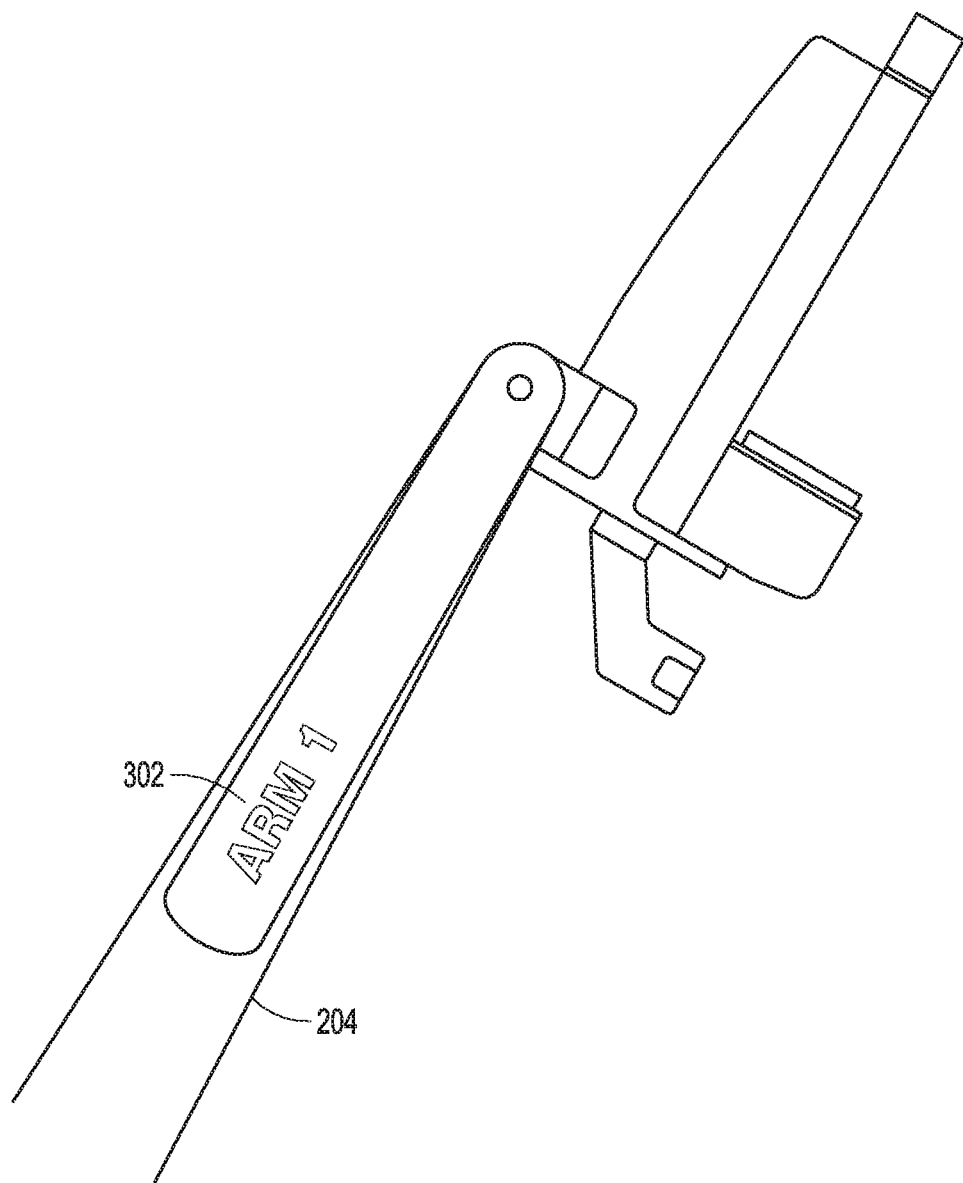
FIG. 3C is an illustration of an integrated display in an arm portion of a manipulation system in a ready to drape kinematic pose.

The information presented on a controllable display may further indicate many possible states, commands, or suggestions, such as an arm pose (e.g., IV stand, transport, ready to dock), or system operating modes that correspond to the arm pose. For example, when the arm is posed for draping in drape mode, the integral display may indicate "DRAPE" as shown in FIG. 3C, and the "DRAPE" indication disappears when the arm pose is moved out of the ready to drape pose. The display may similarly output other indications such as "IV STAND" or "TRANSPORT" or "DOCK" when the arm is placed in the corresponding poses as described above.

In various examples, a controllable display such as the integral display 302 may be controlled to output any of the following to a clinical user, in various ways such as by an indicator, text, or abbreviation, or combination. These display examples are illustrative and are not limiting; persons of skill will understand that various other types of clinically relevant information, especially information relevant to a particular manipulator arm or to an instrument coupled to the particular manipulator arm, may be displayed on the particular manipulator arm as an aid to clinical personnel before, during, and after surgery. And, the information may be displayed in any of the various ways described herein. As examples (i) the system is in setup mode and is ready to be moved toward docking with a cannula; (ii) the system is in standby mode; (iii) the system is ready for transport, such as with the arm stowed in a compact pose to allow system to be easily rolled on floor (e.g., IV stand pose), or the arm is posed to be easy to handle for transport (e.g., transport pose); (iv) the system is ready to be draped; (v) the system is properly draped; (vi) the system is ready for roll-up next to a patient on an operating table; (vii) the system is ready to dock to cannula; (viii) the system is docking with cannula; (ix) the system is docked to cannula (x) the system is operating in a therapeutic or diagnostic mode, such as when master/slave following relationship is established between master control device and instrument; (xi) the system is ready to change instrument mounted on the system (or in a multi-arm system indicate which arm has the instrument to be changed); (xii) an instrument is transitioning from one operating mode to another operating mode, such as stapler or energy instrument firing; or (xiii) the system is approaching or is at a center of gravity limit and is too close to a possible tipping.

In further examples, the system may control the integral display 302 to (i) output an instruction (e.g., "DRAPE THIS WAY→"); (ii) display a system status (e.g., "GETTING READY TO DOCK"); (iii) report a status of arm unit (e.g., "READY FOR TRANSPORT"); (iv) show an elapsed duration of surgery or elapsed time under anesthesia; (v) show duration that a vessel has been clamped (e.g., ischemia duration during partial nephrectomy); (vi) show countdown from pre-established time limit (e.g., countdown stopwatch feature); (vii) time to fire (e.g., energy instruments preparing to release energy); or (viii) show information relevant to an instrument mounted on the corresponding arm (e.g., number of allowable uses remaining for the instrument, number of clips remaining for multi-fire clip applier instrument, etc.).

In still further examples, a controllable display (e.g., integral display) may be controlled to output a communication (e.g., instruction or alert or comment) between clinicians, e.g., from a surgeon to a nurse working in sterile field, or a computer-generated communication to a clinician. For instance, a surgeon at a remote user console may indicate that a particular instrument is to be removed, and a display on a manipulator arm corresponding to the particular instrument indicates that the particular instrument is in fact mounted to the arm so that the bedside clinician does not mistakenly remove the incorrect instrument. As another example, an image processing system detects an endoscopic image degradation and the system correspondingly indicates on the arm to which the endoscope is mounted that the endoscope should be removed and its lens cleaned.

In some examples, the controllable display may output the instrument type that is coupled to the arm (e.g., camera, stapler, cutter, grasper), or a status of an instrument coupled to the arm (e.g., usable lives or time remaining, status of staple cartridge, status of electrosurgical energy application, warning about instrument capability, etc.). Or, the controllable display may output an indication of a current system operating mode (e.g., following mode, commanded clutch mode, break-away clutch mode, standby mode, transport mode, or other modes). For example, the controllable display may output information in green or blue during the following mode, output a flashing clutch indication in yellow or red when a clutch is commanded by pressing a button or by "breaking away" from a commanded pose when moved by hand, and output an operating mode indication in blue or purple during the standby or transport modes.

In various examples, the controllable display (e.g., integral display 302) may be controlled to display textual forms such as words, abbreviations, or letters in either static or animated ways, or it may be controlled to display graphical forms such as symbols (e.g., arrows to indicate direction, a numeral to indicate a particular arm) or icons (e.g., to present a flashing lightning symbol when electrosurgical energy is applied).

In some examples, the controllable display (e.g., integral display 302) may be controlled to indicate a safe or correct hand contact point on an arm (e.g., "GRAB ARM HERE" or "PUSH SILVER HANDLE→"). For example, a safe or correct grab point may be indicated on an integral display when a manual adjustment of the arm is required or recommended, such as lowering a portion of the arm 204 during drape mode, or such as directing a user to a handle or push point during transport mode. In some examples, the integral display may be controlled to indicate a joint that is manually adjustable, e.g., when one or more of the arm joints are locked and one or more of the arm joints are manually adjustable (e.g., rotational arm joints are locked in the ready to dock mode, but prismatic vertical column joint is manually adjustable). In some examples, if an arm link moves as the result of a user touching a force sensor on the link, the integral display may be controlled to indicate which force sensor to actuate and how to interact with arm. For example, the display may present a message with a location or direction indicator (e.g., "PUSH HERE" or "PULL THIS WAY 4").

In some examples, the controllable display (e.g., integral display 302) may present an instruction, alert, or warning about manipulating or interacting with the arm or system, such as "DON'T TOUCH THE ARM!" if a clinician touches the arm while the surgeon is operating the manipulating system in the following mode.

In some examples, the controllable display (e.g., integral display 302) may be controlled to indicate detected touch on arm or instrument, e.g., the integral display may present a message stating "DETECTED TOUCH AT STERILE LOCATION" or "DETECTED TOUCH AT NON-STERILE LOCATION" or a symbolic indication thereof.

In some examples, the controllable display (e.g., integral display 302) may be controlled to present an assignable or computer-determined labeling or description of one or more portions of the system (e.g., an arm). A label may be arbitrary, such as "ARM 1" or "ARM 2". Or, a label may be based upon a function of the arm or the tool mounted on the arm, such as "GRASPER ARM", "NEEDLE DRIVER ARM" "STAPLER ARM" or "RETRACTOR ARM". The controllable (e.g., assignable) arm number/designation may support modularity, because two or more similar manipulator systems (modular units) may be used together as described herein, and confusion amongst the systems may be inhibited or reduced by the labeled number or designation on the integral display (e.g., Arm 1 can be differentiated from Arm 2 by using the displayed labels on the arms). In some examples, integral displays on systems or arms may communicate regarding three or more arms working together (e.g., to support two instruments and a camera, each mounted on a separate manipulator system's arm). To differentiate the arms, the integral displays may each display something different (e.g. "ARM 1", "ARM 2", "ARM 3").

A controllable display (e.g., integral display 302) may provide an operator with an adaptive way to assign and reassign designations. For example, in a modular system, it may not be known which system will be Arm 1, Arm 2, and Arm 3 (Or "grasper arm," "stapler arm," "camera arm") before a procedure starts, and the systems may be assigned labels at the beginning of a procedure, or reassigned labels during a procedure (e.g., a label may be reassigned associated with a tool change, e.g., a "NEEDLE DRIVER ARM" label may become a "STAPLER ARM" label). The controllable displays may enable dynamic switching of arm designation numbers during a surgical procedure (e.g., repositioning or reassigning arms so that originally labelled "ARM 1" becomes "ARM 2" and vice-versa). In some examples, indicia such as color, pattern, or brightness on other light features (e.g., display, rings) may match an aspect of the integral display (e.g., color or arm number or name) to help distinguish portions of the system or arms. For example, displays or light features on one may arm appear in one color, and displays on a second arm may appear in a different color.

In some examples, the content displayed on a controllable display may be tied to a step in the procedure. For example, the controllable display may state "staple reload required", "move me", or "replace my instrument with a stapler." The displayed information may be triggered by an event, a system state (e.g., nearing end of range of motion or stapler empty) or may be triggered by a request (e.g., a clinician request). As another example, a manipulator system detects that an arm has been properly draped with a sterile drape, and one or more light features are lit in a color (typically blue) to indicate the draped portion of the arm is sterile.

In some examples, when an operator is in a certain step in a pre-surgical or surgical procedure, the display may indicate which arm to change, so that it is clear which one of the arms is the one that needs to be serviced. The indication may be literal ("move me") or symbolic (e.g., a picture of an empty stapler) or arbitrary (e.g., flashing lights to indicate an arm to be moved or otherwise serviced. In some examples, light features (e.g., rings) may light up or change (e.g., change color or brightness or animation state). Such a display may be triggered by a system event or user request. In some examples, when surgeon requests an instrument change, one or more displays on the arm may light up to indicate that it is the arm for which the change is requested. For example, a display on an arm may output "CHANGE MY INSTRUMENT" so it is clear which one of the arms is the one that needs to be serviced with an instrument change. In some examples, the surgeon's request may specify the instrument type to be changed, the system memory has stored which instrument is assigned to (mounted on) each arm, and accordingly the system may identify the appropriate arm.

In some examples, a general system or system component fault, or a joint at or near a range of motion limit, may trigger a display, such as an illuminated component or other indicia on a display screen or other light feature.

In some examples, information (e.g., text or graphic) on a controllable display may help guide the user through steps to change a kinematic pose. For example, a display may present a static or animated "PUSH HERE→" or "PRESS CLUTCH BUTTON" or "MOVE THIS ARM", or a similar static or animated graphic, to indicate which structure to move or direction of movement.

Behavior of Light Features

In various examples, the behavior of light features (e.g., integrated displays, lighted rings (see discussion below), or other light features may be controlled to communicate to a user (e.g., clinician or operator).

The light feature outputs may be various individual colors, or the light feature outputs may change colors, or the light feature outputs may be simultaneous multiple colors (e.g., a red-blue-red-blue pattern across an area). The light color may change, for example, from red to blue, or from red to blue and back to red, or red to blue to white to blue to red (e.g., to indicate a state or a value in a continuum or range). In some examples, the lights may pulse or flash (e.g., pulsed LED or flashing LED). A pulse may be a discrete pulse or flash, or a soft transition (e.g., a "breathing" light having a pulse frequency of 1 second, 2 seconds, 3 seconds, or 5 seconds, or longer). In some examples, a system may use a waveform to control lights. For example, a system may use a sawtooth waveform pattern where a light becomes gradually brighter, and then quickly dims. In another example, a system may use a smooth oscillating pattern (e.g., sine wave), which may cause a gradual, repeated increase and decrease of light intensity over time. Other waveforms may be used for brightness and color changes, and different waveforms or waveform frequencies may also be used to communication system information to the user (e.g., a light feature outputs a smooth and slow light change to indicate a normal system state, and the light feature outputs a harsh or rapid light change to indicate an alert or warning system state).

Various types of information may be communicated by using a light feature as described herein. In some examples, the appearance (e.g., color, pattern, brightness, animated motion, or other visual characteristic) of one or more light features may correlate to system operating mode, arm function, or instrument function. In some examples, a light feature may communicate a status or aspect of a patient. For example, a light feature may track with a patient's detected heart beat or respiration or it may indicate a patient health warning state. Various other examples are provided below in a section titled "Communicating Using a Light Feature."

Patient Detection

In some examples, a manipulator system may be configured to communicate based upon patient detection. For example, a system may sense a patient location and position in 3D space (e.g., using depth mapping technology, proximity sensing technology), or it may receive such information from another system, and the system may use the patient information to dynamically configure the arm in a way that is appropriate or safe. The configuration may be context-sensitive (e.g., a manipulator system or arm configuration may be based on both information about the patient and information about a procedure or the availability or status of equipment, tools, or other systems). For example, the system may move to a "ready to dock" pose that will may provide adequate or safe arm-to-patient clearance during surgery (e.g., an arm may be oriented at a height that is higher than a patient to avoid a collision between the arm and a patient or to orient and position an instrument mount at an appropriate height above a patient (or patient surgical site) to facilitate a surgical procedure. In another example, a system may move an arm to a "ready for teleoperation" pose that is calculated to provide adequate or safe arm-to-patient clearance, or adequate or safe arm-to-second arm clearance during surgery. In some examples, the system may indicate that an arm, or a specific location on an arm, is at a "too close to patient" pose or a "near to colliding with patient" pose. In some examples, a system may indicate that an arm or instrument is near or at the end of a range of motion with respect to the patient ("unable to move farther in this direction"), such as a maximum possible instrument pitch or yaw.

Other Display Features

The system may also control the integral display 302 to show a guided setup instruction set or checklist. Information on guided setup is found, e.g., in U.S. Patent Application Publication No. US 2017/0172674 A1 (filed Sep. 9, 2016), which is incorporated herein by reference.

Any of the controllable display features described above, as well as any additional display or visual indication features described below, may be used in a surgical environment in which the display is covered by a transparent sterile drape. A drape may be secured near or over the display to make the display more visible through the drape (e.g., the drape may be positioned flat across the display). In various examples, ties, loop and pile fasteners, magnetic fasteners, etc. may be used to secure the drape in this manner.

Displays and Arm Operations

Figure 4A:
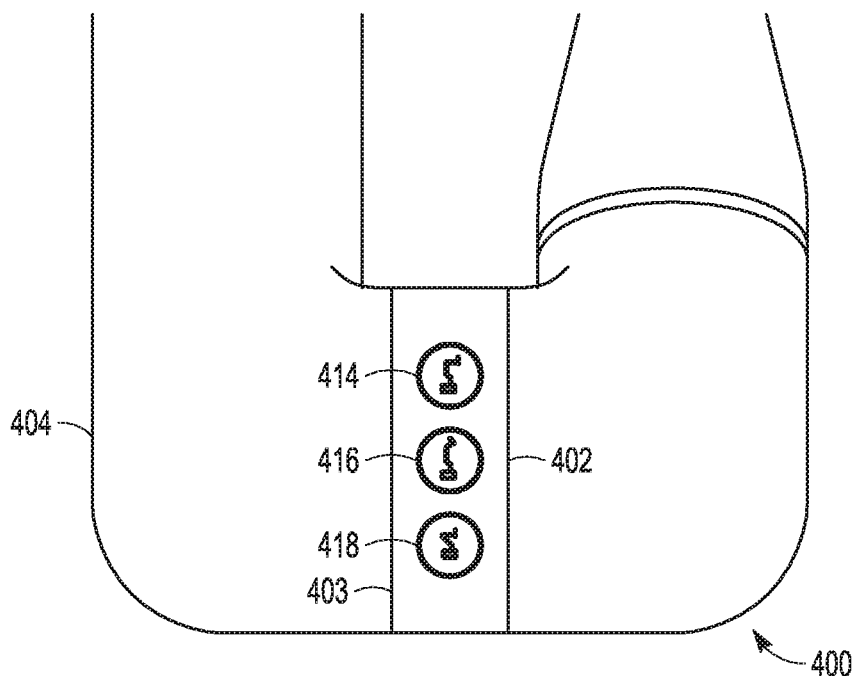
FIG. 4A is an illustration of a display on an arm portion of a manipulating system.
Figure 4B:
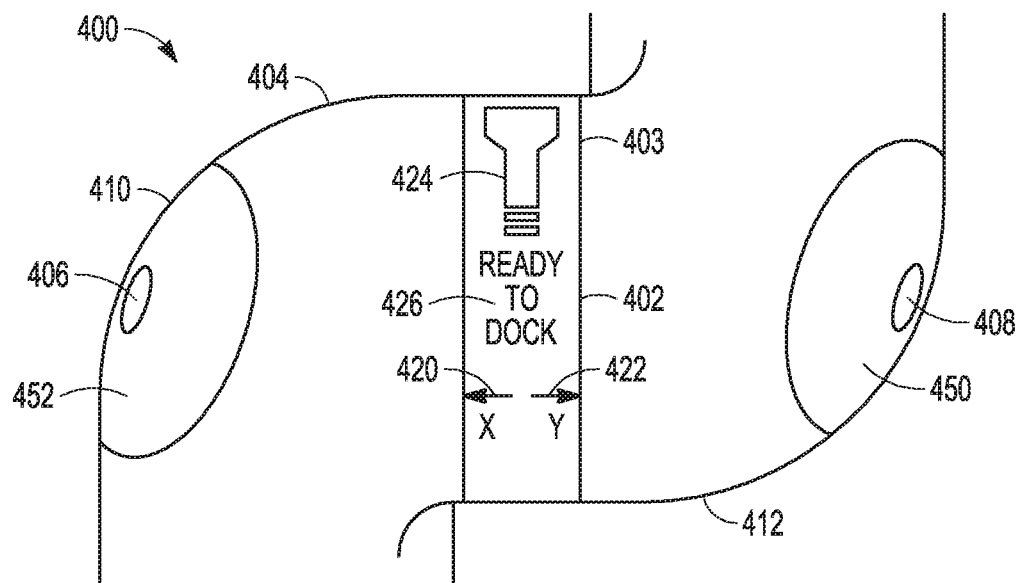
FIG. 4B is an illustration of a display on an arm portion of a manipulating system and buttons on the arm.

FIGS. 4A are 4B are illustrations of a portion of manipulating system 400 that has a display 402 (e.g., organic light-emitting diode (OLED) display) on a portion of the arm 404. In some examples, the display 402 (e.g., OLED display or similar display) may be located between two major structural portions 410, 412 of an arm 404, such as between two "elbow" links or between an elbow and a bend portion of an arm link as described above. For example, the display 402 may be between the first elbow 218 and second elbow 220 of the system 200 shown in FIG. 2A, or between the second elbow 220 and the first bend 222, or between the second bend 224 of the first link 216 and the third elbow 228. In other examples, the display 402 may be on a major structural link, or the display 402 may be on a small separate link between two major structural links.

As shown in FIG. 4A, a user interface 403 on the display 402 may be controlled to show user-selectable elements (e.g., virtual buttons) 414, 416, 418, which may correspond to different poses of the arm 404 (e.g., selecting a button 416 may cause the arm 404 to move into drape pose and selecting icon 418 may cause the arm 404 to move into transport pose).

As shown in FIG. 4B, the display 402 may be on an arm 404 that has buttons 406, 408 on portions of the arm 404 near the display 402. The user interface 403 on the display 402 may have one or more indicators 420, 422 that points to a button 406, 408, which may for example indicate to a user to press the button to activate an operation of an arm 404. The user interface on the display 402 may also include an indicator 424 (e.g., a stripe) that changes (e.g., appears to scroll or move, or changes color, size, or brightness or other appearance) as a joint (e.g., a joint at or near where the display 402 is mounted) moves through a range of motion. For example, the indicator 424 may be animated to indicate movement or impending movement, or all or a portion of the indicator 424 may change appearance (e.g., color) to indicate that an end of a range of motion is near (e.g., change from green to yellow to red as a joint approaches a range of motion limit). The user interface 403 may include a status indicator 426 (e.g., an icon, or text that says "READY TO DOCK").

In some examples, the display 402 may be configured or controlled to change as the arm 404 or an elbow or other joint moves. The display 402 may, for example, be configured to "follow the user," so that as the arm 404 or elbow moves, the information on the display 402 remains visible to the user (e.g., see upward-angled display in FIG. 4A). For example, the display 402 may be configured or controlled so that for a plurality of orientations (e.g., any orientation) of adjacent components (e.g., elbows adjacent the screen) or for a plurality of poses, the display 402 is at a constant orientation with respect to vertical or a specified frame of reference (e.g., user location, world reference frame with gravity vector defining the z-axis, etc.) so that a clinical user viewing the display 402 can see it at the same viewing angle as the pose of arm 404 changes. Likewise, control inputs such as buttons associated with a touch display may change orientation with reference to the arm 404 as the arm pose is changed. The control inputs may remain oriented at a constant angle to a reference frame outside the system as the arm pose changes. Or, as the arm pose changes the control inputs may translate along the display 402 so that they remain oriented towards a point in space (e.g., when the display is relatively low with reference to an average user, the control inputs are oriented upward, and when the display is relatively high with reference to the average user, the control inputs are oriented downward). In this way a clinical user can easily view the display 402 and operate the control inputs at various arm poses.

In some examples, a person viewing the display may select the display orientation by translating it along the display area (e.g., by using a virtualhandle on the display, or by using a touch-sensitive element, such as a touch-sensitive OLED screen), and the system may then maintain the selected orientation with reference to a reference frame defined on or outside the system. The system may assume a viewing distance (e.g. one meter) or it may calculate a viewing distance (e.g., based on sensors that determine the position of a person relative to the display). An accelerometer or an inertial measurement unit (IMU) or like technology may be used to define orientation of the display, the arm, or both.

In various examples, the full circumference of an arm link or elbow may be an OLED display (i.e., the OLED may extend all of the way around the surface of the arm), or the OLED display may extend part way around (e.g., one quarter, or one third, or one half way around the arm).

The OLED display may be configured to present information to a user, to receive an input from a user, or both. For example, one or more optional touch buttons on the display may enable a user to select one or more of various system functions or modes. For example, one or more indicators on the display may communicate any of the information described above or below (e.g., current pose, alerts or warnings, range of motion status, arm label (e.g., ARM 1), or connected tool (e.g., stapler)). Conveniently, the display may be positioned at or near the arm location that in the transport mode extends beyond the vertical boundary of the base as a push point for the user (see e.g., FIG. 2J), or at a similar location when the arm is being set up for or used during surgery (see e.g., FIGS. 2E and 2I).

In some examples, one or more of the touch buttons 406, 408 on the system (e.g., at an elbow) may include or be combined with an indicator (e.g., light feature) on the button. For example, an appearance of one or both of the touch buttons 406, 408 may change based on a user touch or a system event. In some examples, any of the various display output appearances described above may be applied to the touch buttons 406, 408 (e.g., a light feature on or around the button may change to indicate an identity of the arm, a pose, a status, etc.).

Interaction of Screens and Other System Input Devices

In various examples, a display (e.g., integrated display or OLED display) may present options that are selectable with physical or display buttons placed nearby, e.g. buttons 406, 408 on the elbows adjacent to the screen. In some examples, the display 402 may indicate location of relevant button for a particular desired feature (e.g., indicated using an arrow). For example, selectable options may be presented on the display 402 and optionally indicated as associated with a particular button (e.g., using an arrow), and an option may be selected by pressing an appropriate one of the buttons 406, 408. In various examples, receipt of an input (e.g., button press) through a button may move the display through screens, navigate menus, or initiate an action. In some examples one or more of the buttons 406, 408 may operate as a joint lock control (typically called a "clutch" feature). For example, the button may lock or unlock one or more of the joints in the system shown in FIGS. 2A and 2B.

In some examples, a system may cause a joint or multiple joints in an arm to freeze (controllably lock) in position. In some examples, a button push (e.g., an individual button push; a subsequent push of the same button; etc.) may unlock a joint or multiple joints. In some examples, joint locking and unlocking may be controlled with two separate buttons, e.g., one button (e.g., button 406, optionally indicated with an indicia such as a red light feature) may be used to for locking one or more joints, and a second button (e.g., button 408, optionally indicated with a second indicia such as a green color, which optionally only appears when the one or more joints are locked) may be used for unlocking one or more joints (e.g., the joints unlock and return to an assisted move state, a gravity compensated state, or a teleoperated state after being unlocked). In some examples, a button lock command may prevent teleoperated movement or movement in response to a processing system 180 or movement responsive to user control system 150. In some examples, commands from a user control system 150 or processing system 180 may be executed by moving other joints or aspects of the manipulating system while maintaining a locked joint in a lock state (e.g., to avoid a collision with an object of which the system 150 or 180 may not be aware).

In some examples, a single button that may control two bi-stable joint lock/unlock modes (e.g., a first press locks one or more joints, and a second press unlocks the one or more joints). In some examples, a code or pattern may be required to lock or unlock one or more joints to avoid unintended commands, e.g., two buttons presses within a short time (a "double click"), or three presses in sequence within a time, or a long press, or a short press followed by a long press, or variations thereof may be required to initiate a lock operation, and the same or different code or pattern may be required to unlock the one or more joints.

Touch Points

Figure 5A:
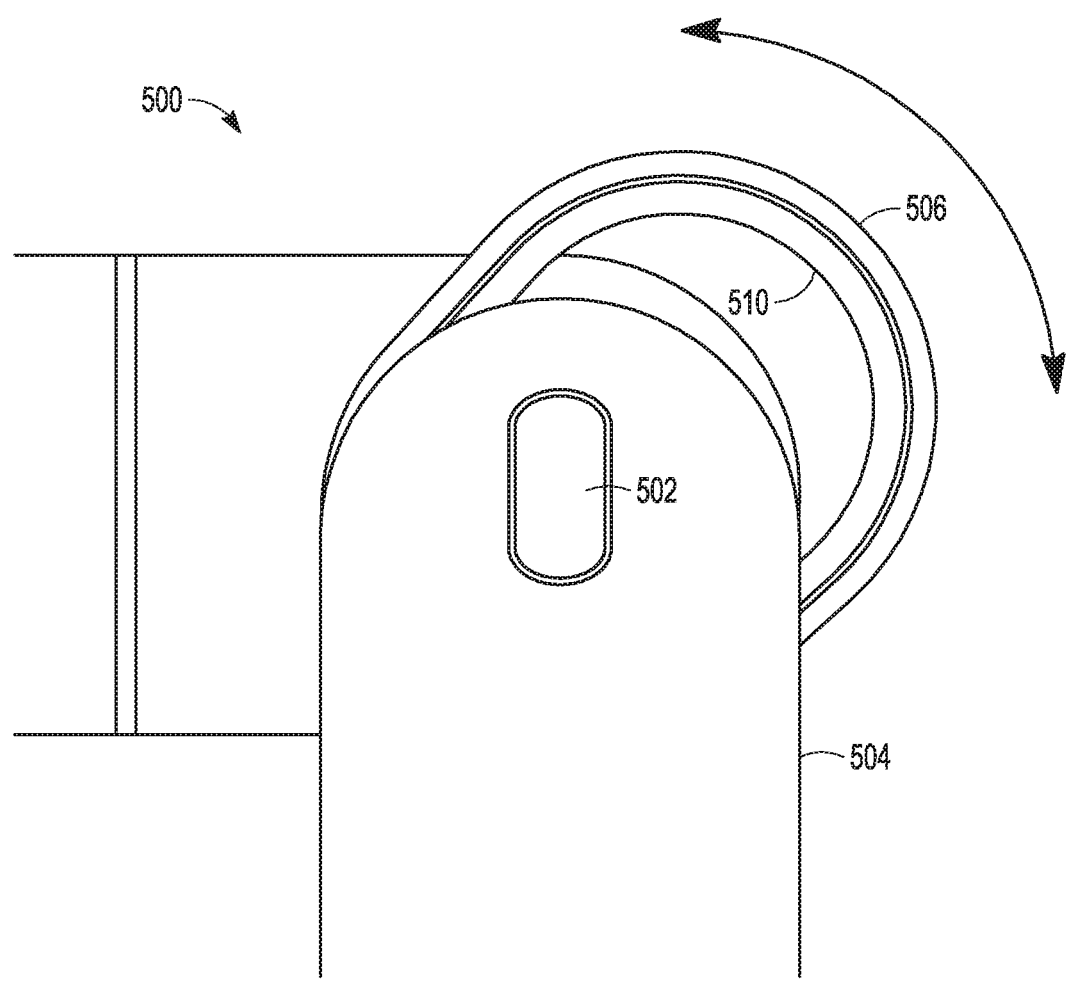
FIG. 5A is an illustration of a handle on an arm of a manipulating system.

In various examples, a system may include one or more designated touch points (e.g., touch sensor) at one or more locations on arm to select various system functions or system operating modes. For example, the buttons 406, 408 shown in FIG. 4B may be touch points rather than mechanical pushbuttons. FIG. 5A is an illustration of a portion of a manipulating system 500 and a touch point 502 on an arm 504 of the manipulating system 500. FIG. 5A also shows an arm handle 506, which may also be a touch point.

The manipulating system 500 may initiate an action in response to touch. In some examples, a system may require a touch at a certain location to carry out a certain action, and for such an action the touch point is located to provide an ergonomic control for the user. That is, the touch point is located at or near a safe and recommended location at which the user would or should touch the manipulating system in order to physically carry out an action, or to observe an automated action carried out as the result of the touch. A touch point may be integrated into an arm link or into a display, such as the black strip OLED display 402 shown in FIGS. 4A and 4B and described above. In some examples, a touch point may be combined with any of the light features (e.g., light rings, other controlled displays) described above. For example, a light ring, a portion of the light ring, or a lighted or unlighted portion of a light ring (which may dynamically change) may be a touch point. Similarly, a touch point may be located near such a light ring or light ring portions (e.g., a touch sensor ring adjacent the light ring). Other light features may function similarly. In various examples, a light feature may indicate where to touch, direction of arm movement, or an arm or system status (e.g., ready to move). A light feature itself may be the touch point that is responsive to touch, or the light feature may be adjacent the touch point.

Handles

Figure 5B:
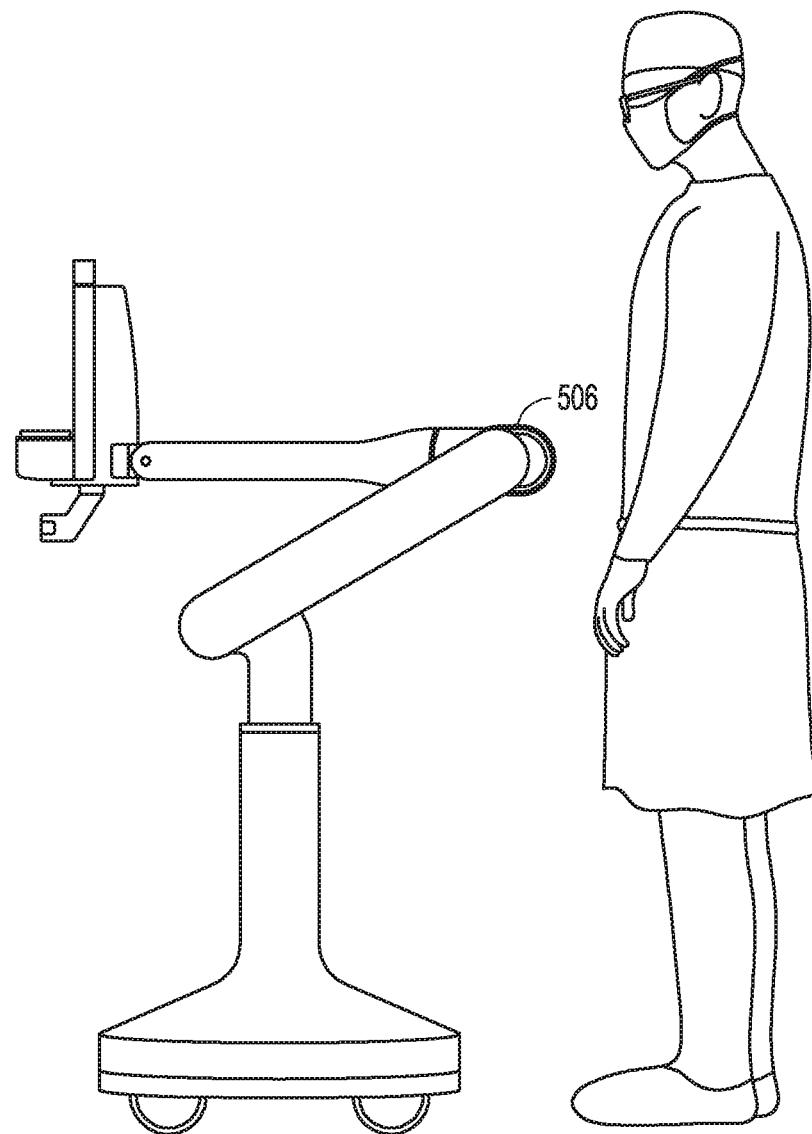
FIG. 5B is an illustration of a manipulating system with a handle presented to a user.

A manipulating system may include one or more handles, such as a vertically-oriented handle (e.g., handle 506 shown in FIG. 5A, shown at an acute angle upward relative to the plane of the floor), a horizontally-oriented handle (e.g., handle 506 shown in FIG. 5B, shown oriented generally parallel relative to the plane of the floor; handle portion 805 of the helm 213 shown in FIGS. 2A and 8; or handle 702 in FIGS. 7A-C), or handles in other orientations or variable orientations. The system may have a mini handle, or a mini helm, an egress handle (e.g., to trigger an egress of an instrument from a patient or a system from a surgical table), an emergency handle (e.g., to trigger an emergency stop of an operation of the system), a sterile handle, or a non-sterile handle, or any combination thereof. The handle 506 shown in FIG. 5A may, for example, be the handle 227 shown in FIGS. 2A and 2B.

In some examples, the handle may have an automatic leveling feature. For example, a system may be configured so that during a change in arm pose a handle remains level (i.e., horizontal with reference to the floor), or the handle remains at a pre-defined (e.g., +20 degrees with reference to the floor) or user-defined (e.g., user has placed handle at a comfortable orientation for the user's height) angle, or the handle moves to a predetermined or context-appropriate orientation so as to be accessible throughout a range of arm positions or orientations, e.g., as the arm moves to various kinematic poses such as moving into a transport, IV stand, or docking pose. A manipulating system may include one or more motors that may be controlled to control an angle of a handle with respect to an arm as determined by one or more sensors that directly or indirectly sense joint angle, or as determined with respect to a gravity vector or some other reference orientation outside the system as determined by an associated sensing system (e.g., accelerometer, indoor positioning system, etc.).

In some examples, a manipulating system may include a level sensor, and level sensor data or information based on level sensor data may be used as an input enable leveling of the handle as the arm moves. A level sensor may be inside a handle, or it may be inside a structure proximate a handle, such as an arm or elbow. A manipulating system may maintain a handle at an angle other than horizontal, e.g., a sensor may determine horizontal, and a handle may be maintained at a specified angle or range above or below horizontal, e.g., 30 or degrees above horizontal (see FIG. 5A which shows a handle 506 at about 45 degrees above horizontal; FIGS. 2B, 2D, and 3A which show a handle 227 level with horizontal; FIG. 5B which shows a handle 506 level with horizontal; FIGS. 7A-7C and 9A-9D show a handle 702 level with horizontal), and the specified angle may be constant, or it may be determined based upon sensor input or a computed state (e.g., the handle may rotate up or down based on height to extend toward a user) or context (e.g., the handle may rotate into a specified orientation that corresponds to a pose).

In some examples, a system may include an auto-angle feature so the handle 506 is configured at a convenient angle for the user. For example, FIG. 5B is an illustration of a manipulating system with a handle 506 presented to a user. The system may move the handle 506 so it is oriented toward a user. For example, a system may control a handle so that the handle angles upward from horizontal (e.g., as shown in FIG. 5A) when the arm is in a pose in which the handle is relatively low with reference to an average user, and the system may move the handle so that the handle angles downward from horizontal when arm is at a pose in which the handle is relatively high with reference to an average user. In addition, any of the handle orientation features described above may also be applied to controlling orientation of a handle.

In another example, a manipulating system may maintain a stored memory of user height or user preference for handle height or orientation angle, and as the arm changes position, orientation, or kinematic pose, the system may move the handle height or orientation based on stored user information.

In some examples, a handle may include buttons on the inside of the handle, for example at inside surface 510 shown in FIG. 5A. In various examples, one or more buttons may (i) control the handle's movement (e.g., actuating a button may control one or more motors that moves the handle); or (ii) may release ("clutch") the handle to enable manual adjustment of the handle, or lock the handle; or (iii) buttons may control other system functions.

Figure 7A:
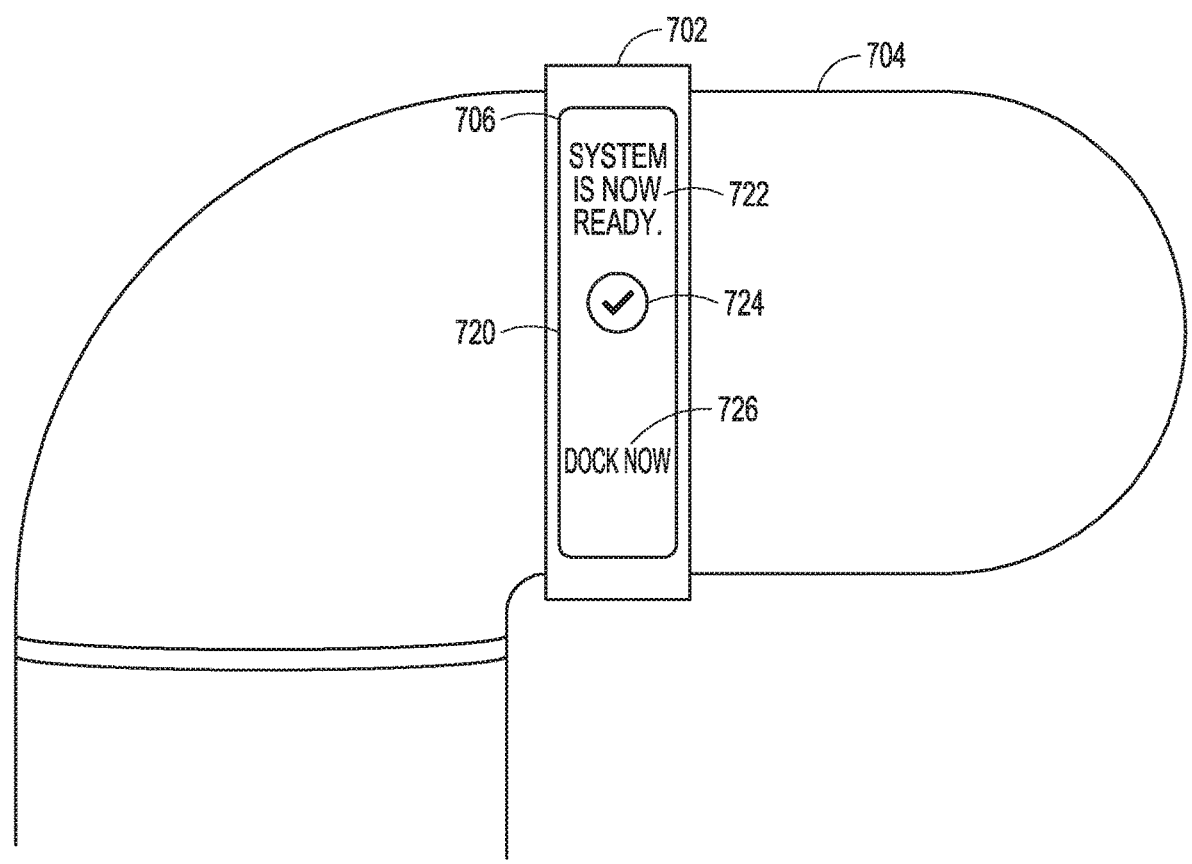
FIG. 7A is an illustration of a handle on a display.
Figure 7B:
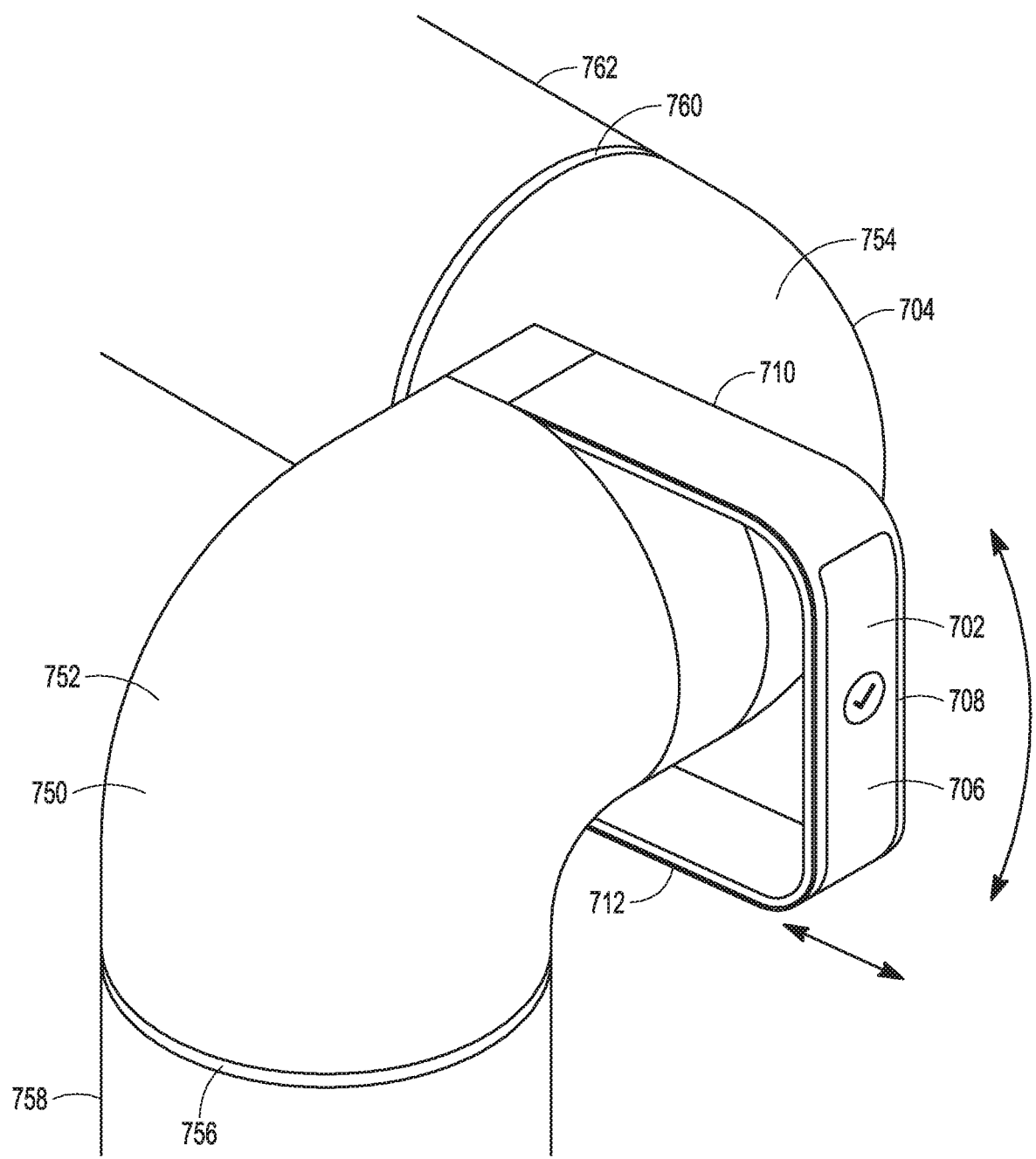
FIG. 7B is a perspective illustration of the handle shown in FIG. 7A.
Figure 7C:
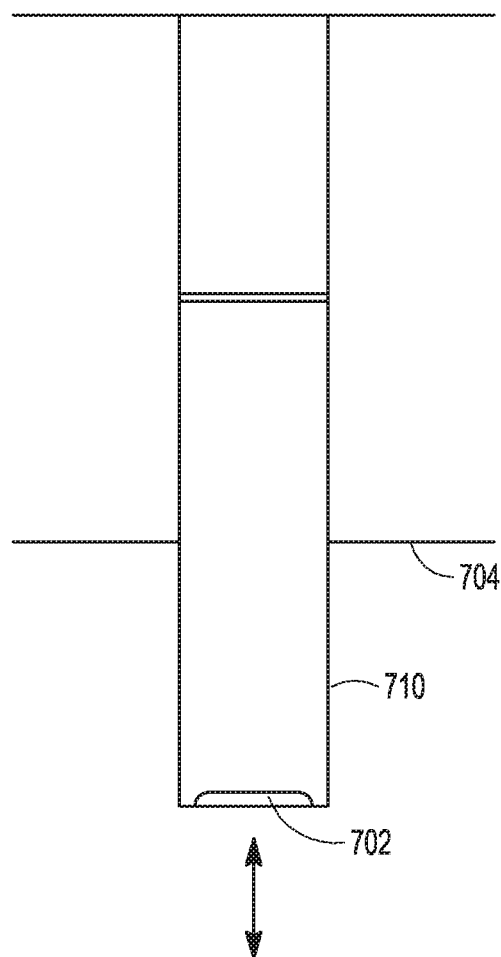
FIG. 7C is a top view of the handle shown in FIG. 7A and FIG. 7B.

In some examples, a handle may include an arm or instrument egress feature. An instrument egress feature may cause an instrument to automatically retract from the patient. An arm egress feature may cause an arm or an entire system to automatically perform actions such as undock from a cannula, move to a pose that allows a clinician to move the system away from a surgical table, or move away from a surgical table. Instrument and arm egress features may optionally be combined. In some examples, a specific handle motion (e.g., rotation through a specified angle or a pull of the handle through a specified displacement, or a combination of movements) may initiate an instrument, arm, or combined instrument and arm egress. An egress may also be initiated by via an input through one or more buttons on the handle or through a display (e.g., OLED display), or through a display on a handle. In some examples, a system may include a dedicated handle 702, as shown in FIG. 7C. Light features as described above may output information associated with an instrument or arm egress function, such as indicating the arm associated with the instrument withdrawal, or indicating which arm or arm joint is about to move and optionally in which direction, or indicating which manipulating system is about to move away from the table.

In some examples, a manipulating system handle as described herein may be configured to be sterile (e.g., in the sterile field). A sterile handle may be draped (by a sterile drape). In some examples, a handle may not be sterile, or a first handle may be sterile, and a second handle may be non-sterile. A sterile or non-sterile handle (or both) may be indicated by an appearance associated with its function, such as a color, pattern, or material.

Any of the handles described herein may be used for general transport when a system is stowed or otherwise placed in a kinematic pose suitable for storage or transport (e.g., IV stand pose, transport pose). For example, the handle 506 shown in FIG. 5B may be used to assist with navigation by providing a convenient grab point to push, pull, or steer the arm or activate controls on the handle (e.g., to initiate a motor-assisted transport mode, which may reduce the amount of push force required to move the unit).

A handle may be sized, shaped, or contoured to facilitate easy and comfortable grabbing or holding by a user. For example, as shown in FIG. 8, a handle 804 may have a generally oval shape, with an optional flare-out 816 (e.g., generally egg-shaped) at the grab location 814.

A handle may be formed from one or a combination of materials, e.g. materials that are both strong (to facilitate pushing and pulling) and easily amenable to sterilization. For example, a handle may be made from a high-grade metal, such as aluminum or an aluminum alloy. A metal (e.g., aluminum alloy) handle may be polished or otherwise finished to give a clean appearance that is consistent with the human engineered design principles discussed above. In some systems, the handle material and appearance may be consistent for two or more unit handles or other touch points, so that touch points have the same appearance for ease of use and clarity of communication to a user (e.g., clinician). For example, when two or more handles have the same general appearance such as rounded and polished aluminum, a user may then learn and understand that rounded and polished aluminum handles, even if they have size and shape variations, provide a safe or appropriate touch point to touch, pull, push, or otherwise physically interact with a manipulating system. Further, if two manipulating systems each have different kinematic architectures, a consistent general appearance of handles on both systems visually reassures the clinician of the proper grab location on either system. For example, one or more rounded and polished aluminum handles may each be used on a first manipulating system that has a single manipulator arm (see e.g., FIG. 2A) and on a second manipulating system that has two or more manipulating arms (see e.g., FIG. 1B). Likewise, one or more rounded and polished aluminum handles may each be used on a first manipulating system that has a manipulating arm having one kinematic architecture (see e.g., FIG. 2A) and on a second manipulating system that has a manipulating arm having a second kinematic architecture different from the first kinematic architecture (see e.g., FIG. 1B).

In some examples, a handle may align with a manipulating system control helm, such as the helm 213 shown in FIGS. 2A, 2B, and 8. Initial helm or handle orientation changes may be automatically controlled by the system or manually by a user, and the corresponding helm or handle orientation change may also be automatically controlled by the system or manually by a user. For example, a handle may align with a control helm in a specified pose. In an implementation in which the handle and control helm are independently movable, the handle may follow the helm orientation, or the helm may follow the handle orientation, or both. For example, if a user changes a helm orientation (e.g., angle with reference to the base) is from one orientation to a second orientation, the handle may automatically adjust to align with the second helm orientation. Similarly, if a user changes a handle orientation, the helm may automatically adjust to align with the second helm orientation.

A handle may be located between links in a manipulating system (an inter-link handle), or a handle may be integrated into a link in a manipulating system (an intra-link handle), either at an end of a link (e.g., adjacent a joint with another link) or mid-link spaced away from the link's opposite ends.

If a handle is moveable with reference to a link, the handle itself is a kinematic link and is coupled to the link at a handle joint. Handle 212 (FIGS. 2A and 2B) is an illustration of an intra-link handle because it is at the top end of the column 210 that extends from the manipulating system base. Handles 227 and 506 are illustrations of inter-link handles because they are located between two arm links.

Figure 6A:
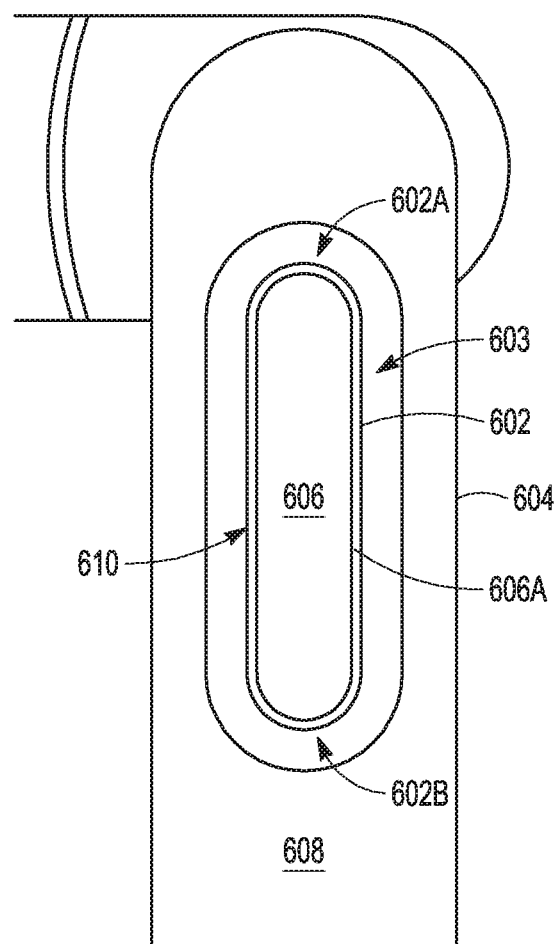
FIG. 6A is an illustration of a retractable handle on an arm of a manipulating system.
Figure 6B:
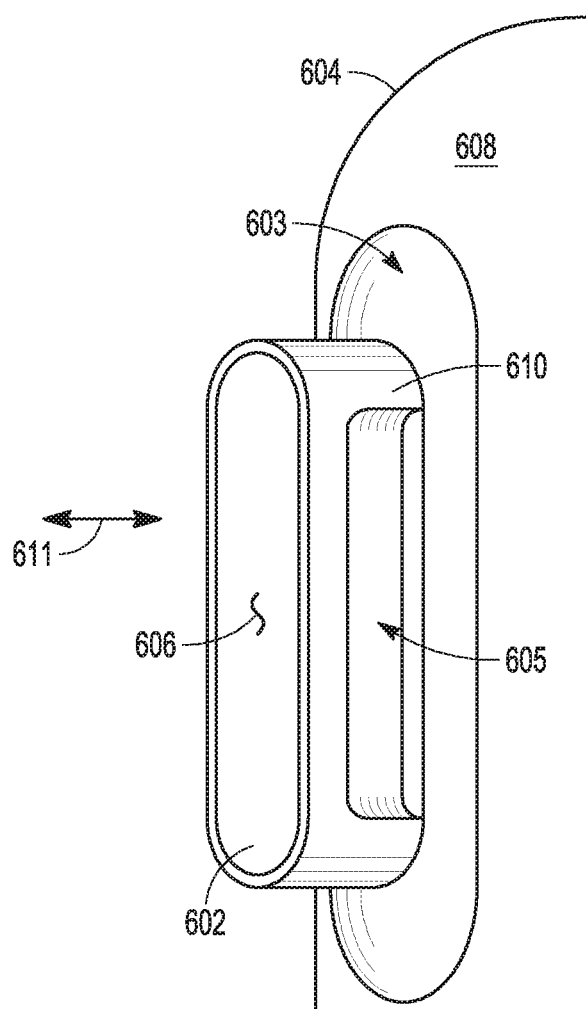
FIG. 6B is a side perspective view of the handle shown in FIG. 6A.

FIG. 6A is an illustration of a mid-link intra-link handle 602 on link 604 of a manipulating system arm (e.g., FIG. 2A, arm 204). FIG. 6B is a side perspective view of the handle 602 shown in FIG. 6A. In some examples, the handle 602 may be used as a grab point for moving a system or arm. And, the handle 602 may include other interaction features as described above, such as controllable displays, light features, mechanical buttons, etc.

As shown, handle 602 is a generally oval shape having a first end 602*a* and an opposite second end 602*b*. Handle 602 includes an outer surface 606 oriented outward from link 604. Handle 602 also includes a sidewall surface 610, which as shown is a continuous surface around the handle 602 but optionally may be two or more discrete surfaces. One or more optional finger recesses 605 may be included in the sidewall surface(s) 610 (e.g., one finger recess 605 on each side of the handle 602; a finger recess 605 may extend partially into or completely through the handle 602) to allow a user to more firmly grasp the handle 602. And handle 602 is optionally located within a recess 603 in link 604.

As shown, the design of a mid-link intra-link handle is consistent with other inter- or intra-link handles and is consistent with the overall human-engineered appearance of a manipulating system, and as a result safety and approachability are conveyed to a clinical user, and also the user's eyes are drawn to the mid-link handle as an interaction location on the system. The mid-link handle may be visually configured to provide a consistent appearance with one or more other inter- or intra-link handles on a manipulating system so as to indicate it is an acceptable touch-point (e.g., safe to grab or designed for touch or grasping). For example, inter-link handles 212 and 506 as described above have a rounded shape and a polished aluminum surface finish, and so a similar appearance is given to mid-link intra-link handle 602 by rounding its ends 602*a*, 602*b* and providing a polished aluminum surface finish to the handle's sidewall surface 610. Optionally, the polished aluminum surface finish is extended part way into outer surface 606 in a perimeter region 606*a* so that when handle 602 is viewed straight on, (i.e., the view shown in FIG. 6A), the rounded and polished aluminum visual appearance indicates to the clinical user that handle 602 is an intended touch point consistent with other touch point appearances on the manipulating system. Outer surface 606, or the inner portion of outer surface 606 bounded by perimeter region 606*a*, may be the same color as link 604 to provide a consistent overall visual appearance to the link 604 and the manipulating system as a whole. Further, all or a portion of outer surface 606 optionally includes a controllable display as described above, and below with reference to handle 702 (FIGS. 7A-7C). And still further, a light ring feature is optionally included in link 604 to fully or partially surround handle 602, or is optionally included in handle 602 to fully or partially surround handle 602's outer surface 606 (e.g., within perimeter region 606*a*; within sidewall surface 610 where it joins outer surface 606).

The rounded shape and the polished aluminum surface finish of the various handles described herein are illustrative examples of an ergonomic design principle for a manipulating system, and skilled users will understand that various geometric shapes (e.g., circular, oval, triangular, rectangular) and various surface finishes (e.g., color, surface texturing, material, light feature, etc.) may be used consistently on a manipulating system (e.g., two, three, four, or more handles as described herein) to designate intended and safe touch points to a clinical user. In addition, a visual border may optionally be placed around a handle to highlight the handle's visual characteristics to a user (i.e., to communicate that a handle is at this location). For example, with reference to FIGS. 6A and 6B, link 604 and handle outer surface 606 may be white, and recess 603 may be dark grey to highlight handle 602's polished aluminum surface finish as consistent with a similar polished aluminum surface finish on handles 212, 227 and/or 506.

As shown in FIG. 6B, handle 602 may be configured to move with reference to link 604 from a stored location outward (as indicated by the arrow 611) to a location in which it is protruding from link 604's surface. Outer surface 606 of the handle 602 may be a continuation of the outer surface contour of link 604 so that in the stowed position, the contour of outer surface 606 is continuous with the outer surface contour of link 604, which preserves the overall contour of the link 604 and the link's human-engineered features as described above (e.g., safe and approachable; constant cross-sectional area along the length of the link, etc.). For example, an outer surface 608 of the link 604 may have a cylindrical shape as described above, and the outer surface 606 of the handle 602 may be a continuation of the cylindrical outer surface 608 of the link 604. As described above, handle 602 may be within a recess 603 when in the stowed position, and so an outer portion of the handle 602 is exposed when the handle 602 is stowed. When the handle 602 is in the protruding position, recess 603 provides space for the user to grab the handle 602 or touch one or more interaction features in the handle 602, and so the handle 602 is required to move a relatively shorter distance into the protruding position for effective user access. In some alternate examples, there is no recess 603, and the outer surface 606 of the handle 602 may be flush with outer surface 608 of the arm. In this situation, the handle 602 is required to move a relatively longer distance into the protruding position for effective user access. In one example, either with or without optional recess 603, optional finger recesses 605 are hidden when handle 602 is in the stowed position and exposed when handle 602 is in the protruding position. The protruding distance shown in FIG. 6B is an example, and longer or shorter protruding distances may be used.

Handle movement from the stored position to the protruding position, and from the protruding position to the stored position, may be controlled by user command, by a manipulating system controller in response to a state or event, or a combination of both user and manipulating system control. In some examples, a user touch point (e.g., force sensor, OLED touch screen area, finger swipe detector, mechanical button, etc.) either on or near the handle receives a user command to extend the handle, and then manipulating system carries out the received command. In some examples, the manipulating system detects a user's hand presence on or near the stored handle (e.g., touch sensor, force sensor, motion sensor, etc.) and in response extends the handle. In some examples the manipulating system extends the stored handle when a particular operating mode is entered because the extended handle is associated with the particular operating mode, such the handle extending when the ready to dock mode or the IV stand mode as described above is entered. In some examples a system event will cause the system to extend, such as when a system fault is detected or if general system power failure is detected. A handle default position may be either protruding or stored.

Methods used to retract the handle from the protruding position to the stored position may be similar to the methods used to extend the handle as described above. In addition, in some examples, the handle 602 may automatically retract from the protruding position to the stowed position after the handle is used. For example, the handle 602 may retract after sensing that has not been used. For example, the handle may include (or be coupled to, or controlled based upon) one or more user presence sensors, such as a force sensor, capacitive sensor (to detect touch), or motion sensor (e.g., to detect motion near the handle). The sensor input may be used to determine (e.g., by a control system or a handle control circuit) whether the handle is still being used, or whether a user or user's hand is still near the handle, and the handle may be retracted after it is determined that the handle is no longer being used or grasped. In some examples, the handle 602 may retract after expiration of a delay period (e.g., after a few seconds). For example, the handle 602 may retract after sensing that a touch or proximate object (e.g., a hand) has been removed or that no touch has occurred for the delay period (e.g., no interaction for a few seconds). In some examples, the handle 602 may retract in response to touch (e.g., a force over a threshold limit toward the stored position) may cause the handle to move toward the stored position). For handle retraction, either by manual command or automatically, an optional safety feature may be included that detects a resistance to the handle retraction (e.g., an excess motor current is detected), and handle retraction either stops or reverses so as to not trap the user's hand in the retracting handle (e.g., in the finger recesses). In some examples, this optional safety feature is not included if handle design is such that there is no possibility of user injury during retraction (e.g., sidewall surfaces are smooth and cannot trap a user's finger when the handle retracts).

Aspects of handle movement and movement control associated with handle 602 have been described in terms of translational motion, and these aspects also apply to handle movement and movement control associated with rotational motion of other handles described herein. In a way similar to the stored and protruding handle 602 positions described above, handles such as handles 212, 227, 506, and 702 may rotate from a stored orientation in which the handle does not protrude from the manipulating system or arm to an extended orientation in which the handle may be grasped or interacted with by the user. For example, handle 227 shown in FIG. 2B in a protruding orientation may optionally rotate to a stored orientation that is not accessible by the user (e.g., parallel to and behind link 214 as illustrated in FIGS. 2G or 2I). Thus a handle may have two or more position or orientation locations depending on various user inputs and conditions.

With reference to handles in general as described herein, in some examples an orientation or position location (or default orientation or position location) of a handle (e.g., handle 602 or any other handle described or shown herein) may vary based on a manipulating system condition or event, such as an operating mode or arm posture. For example, a manipulating system may extend or rotate a handle based on or responsive to satisfaction of a condition, e.g., the system may extend or rotate a handle for or use in an operating mode in which it may be needed (e.g., responsive to a transition of a manipulating system to a transport or an IV stand pose), or a manipulating system may retract or rotate a handle responsive to satisfaction of a condition (e.g., a handle may retract or rotate responsive to docking of a cannula to the system). As shown in FIG. 2G, handle 602 may be useful for moving a modular system when the system is in an IV stand-like pose or another pose.

In some examples, one or more "handle out" states (in which the handle is extended or rotated to a protruding position, or it is maintained in an extended protruding position), may be predefined. A handle out state may be declared or a handle may be extended (or maintained in an extended position) in response to satisfaction of a condition. For example, a handle may be extended or rotated during transport mode or ready to dock mode. In some examples, a "handle out" state may occur (and the handle may be extended) when a system senses that a handle may be needed, such as when a joint or link reaches a range of motion limit that would require the user to manipulate the joint or link. In some examples, a handle may extend or rotate when system switches to transport mode, or when the system determines that the arm is posed in a way that the handle may be useful for transport.

In some examples, a "handle in" stored state may be declared or a system may retract or rotate a handle (or maintain a handle in a retracted position) based on or responsive to a condition, e.g., when the system is in an operating mode in which the handle should not be used. A "handle in" state may be predefined. For example, a handle may be retracted or rotated, or it may stay retracted, while a clinician is operating a system in a "following" mode (e.g., a mode where the system follows movements or inputs from a user control system), or when a system enters cannula docking mode (e.g., after an arm is positioned or oriented to place its associated instrument mount over a cannula inserted into a patient, at which point the handle may no longer be needed), or when a system determines (e.g., senses or receives an input) that an arm is docked to cannula, or when a system determines (e.g., senses or receives an input) that an instrument is mounted on the arm. In some examples, a "handle in" state may be declared when the system senses the arm is in a pose in which the handle should not be available or should be retracted. For example, when a system senses that a handle is at a potentially unstable leverage point that may cause result in unintended movement due to stability (or instability) around a base, a clutch status, or a movability (or immovability) of one or more arms or joints.

The handle 602 (or any other handle described herein) may include one or more force sensors, which may provide input for moving an arm or system such as the system 200 or arm 204 shown in FIGS. 2A and 2B. For example, a manipulating system may provide power-assisted motion (e.g., by controlling motors that move joints or system links or other components) based on force or torque sensed at a handle, and so a small force exerted by the user at a handle location is sufficient to easily move the system, arm, or component that would otherwise require a relatively large force.

FIG. 7A is an elevation view illustration of a handle 702. FIG. 7B is a perspective illustration of the handle 702 shown in FIG. 7A. FIG. 7C is a plan view of the handle 702 shown in FIGS. 7A and 7B. The handle 702 may include an integrated display 706, which may for example be a user interface screen (e.g., touch screen) or other controlled display as described above. The handle 702 may include a first portion 708 that may include the integrated display 706, and one or more side portions 710, 712 that may connect the first portion 708 to an arm 704. The handle 702 may be both a handle and a display. Any of the features described above with respect to handles or displays (e.g., control of orientation or information on the display, release or locking of movement) may also be applied to handle 702 and display 706.

As shown in FIG. 7A, the display 706 may include a user interface 720, which may include one or more indicators or user interface elements (e.g., virtual buttons). An indicator or user interface element may, for example, include text or a symbol, and may be controlled to present a color, brightness, pattern, or other appearances to communicate information to the user. For example, the user interface 720 may include a status indicator 722, which may for example include text that says "READY" or "SYSTEM IS NOW READY." The user interface 720 may include a graphical status indicator 724, such as a check mark. For example, an interface may present a white circle with a green checkmark in the circle, which may indicate a status (ready) or condition (e.g., to indicate that start-up checks were completed successfully.) The user interface 720 may include an indicator of a next step 726, such as an textual or graphical indicator to dock (e.g., "DOCK NOW").

As shown in FIG. 7C, a handle 702 may include an emergency feature, e.g., pulling the handle as indicated by the arrow may trigger an emergency action such as (i) stopping movement of the arm or another component of the system, or (ii) stopping an actuation of a surgical instrument, or (iii) triggering a manipulating system egress procedure from the patient (e.g., withdrawing an instrument, or moving a system away from a surgical table or other object). The handle 702 may include a symbol that may inform a user of a direction or technique for actuating the emergency feature of the handle (e.g., the symbol may indicate to pull the handle). In accordance with human engineering considerations as described herein, handle 702 and its associated pull motion feature may be located on a manipulating system where the pull motion is in the direction of desired system or arm movement associated with the manipulating system control feature controlled by the handle pull feature. For example, in a situation in which a manipulating system is required to egress from a patient bedside, the direction of the handle's pull-motion feature is the same direction as required for system egress, and the handle location is where a user would normally pull to move the system away. And, the handle pull motion feature may initiate one or more automatic actions required for egress, such as a sequence in which an automatic instrument withdrawal is accomplished, and then an automatic undocking from the associated instrument cannula is accomplished, and then system wheel brakes are automatically released to allow the system to be pulled or motored away. In this way a single, intuitive clinical user movement of pulling the system away from the bedside automatically completes all system actions necessary to allow the system to safely disengage and move away from the patient. Optionally, handle movement or force sensors detect a clinical user's pull direction, and system egress direction corresponds to the handle pull direction. And, display features optionally output information that informs the user of the progress of the actions required for egress (e.g., a flashing red light feature at the distal end of the arm associated with instrument withdrawal until complete, then all light features on the arm change color change from red to green when cannula release is complete, and then a flashing green light on the base indicates that brake release is complete). Many other actions and sequences of actions may be controlled by a handle motion, and many other light feature outputs associated with such automatic actions and sequences of actions may be employed. In addition, corresponding audio outputs may reinforce the light feature outputs (e.g., "wait for instrument withdrawal", "wait for cannula undocking", "OK to move system", oscillating warning tone, etc.).

In some examples, the arm may include one or more joints at the handle, e.g., a first elbow portion 752 or second elbow portion 754 may rotate with respect to the handle 702 (e.g., the handle 702 may be on a small link between two elbow links).

Alternatively, in some examples, the arm 704 may include a double-elbow 750 that may include a first elbow portion 752 and a second elbow portion 754 that may be at a different orientation or angle from the first elbow portion 752 (e.g., second elbow portion 754 may be orthogonal to first elbow portion 752). The double elbow 750 may be incorporated into the system 900 shown in FIGS. 9A-C. The system 200 shown in FIGS. 2B-2C may also be adapted to include a double-elbow. The arm 704 may include a first light feature 756 (e.g., a light ring) at an interface between the double elbow 750 and an arm component 758 (e.g., an arm link) and a second light feature 760 (e.g., a light ring) at an interface between the double elbow 750 and another arm component 762 (e.g., a forearm).

Further Manipulating System Examples

FIG. 9A is an illustration of another example teleoperated surgical manipulating system 900 having a manipulator arm 904 mounted on a base 902, which may be mounted on wheels 910 that are coupled to the base 902. While wheels 910 are shown in FIGS. 9A-9C, the example base 902 of FIGS. 9A-9C may alternatively be adapted with one to five or more roller balls or casters (as described in reference to FIGS. 2B and 2C) or omniwheels instead of or in combination with wheels 910, e.g., to enable system movement in one or more various directions (or omnidirectional movement).

The arm 904 may include a vertical column 930, which may include a bend portion 931. The column 930 may be rotatable relative to the base 902.

The arm 904 may include a first elbow 934 coupled to the bend portion 931 of the column 930. The arm 904 may include a first link 938, which may include a first bend portion 936 coupled to the first elbow 934. The first link 938 may be coupled to the double-elbow 750 shown in FIG. 7B. Alternatively, the first link 938 may be coupled to single elbows. A second link or forearm 940 (e.g., forearm) may be coupled to the double-elbow 750 (which is optionally two elbow links coupled directly together or via a short handle link). The forearm 940 may extend to a wrist 942 that may be coupled to a spar 944, which may be a telescoping spar. As described above, the forearm 940 may be thinned on an underside 941 to provide additional access space near the patient.

The arm 904 may include a first light feature 912 that may extend part way or all of the way around the base 902. The light feature 912 may be at or near an interface between the base 902 and the floor so as to effectively communicate visual information about that interface. A second light feature 916 may be at an interface between the base 902 (e.g., a top surface 914 of the base 902 as shown) and the column 930. A third light feature 918 may be at an interface between the bend portion 931 of the column 930 (or a moveable optional elbow coupled to the top of the column 930) and the first elbow 934. A fourth light feature 920 may be at an interface between the first elbow 934 and the first link 938. A fifth light 922 feature may be at an interface between the first link 938 and the double elbow 750. A sixth light feature 924 may be at an interface between the double-elbow 750 and the forearm 940.

The arm 904 may include the handle 702 shown in FIGS. 7A-7C. And, any of the handles, displays, light features, control methods or systems or other systems described herein may be applied to the system 900.

The base 902 may be larger on one side 908, e.g., for weighted stability or extra leveraged support during reach (e.g., extension of arm 904 into cantilever from base 902), and the base 902 may be smaller on the other side 906 for close access to table, as shown in FIG. 9B. Stated another way, column 930 optionally extends from a location on base 902 that is not the center of the base 902.

FIG. 9C is an illustration of two manipulating systems 900, 901 and a surgical table 950. The manipulating systems 900, 901 each may be located across from each other on opposite sides of surgical table 950, and arms 904, 905 may extend toward each other across the table 950. As shown, each manipulating system arm 904, 905 may extend past the other so that each arm has access to a cannula located past a patient's sagittal midline. Alternatively, two or more manipulating systems may be located on the same side of the operating table, as illustrated in FIGS. 2F and 11, each with arms that extend beyond the patient's sagittal midline. Such arm reach allows effective access to minimally invasive surgical sites at various locations inside patients.

Figure 9D:
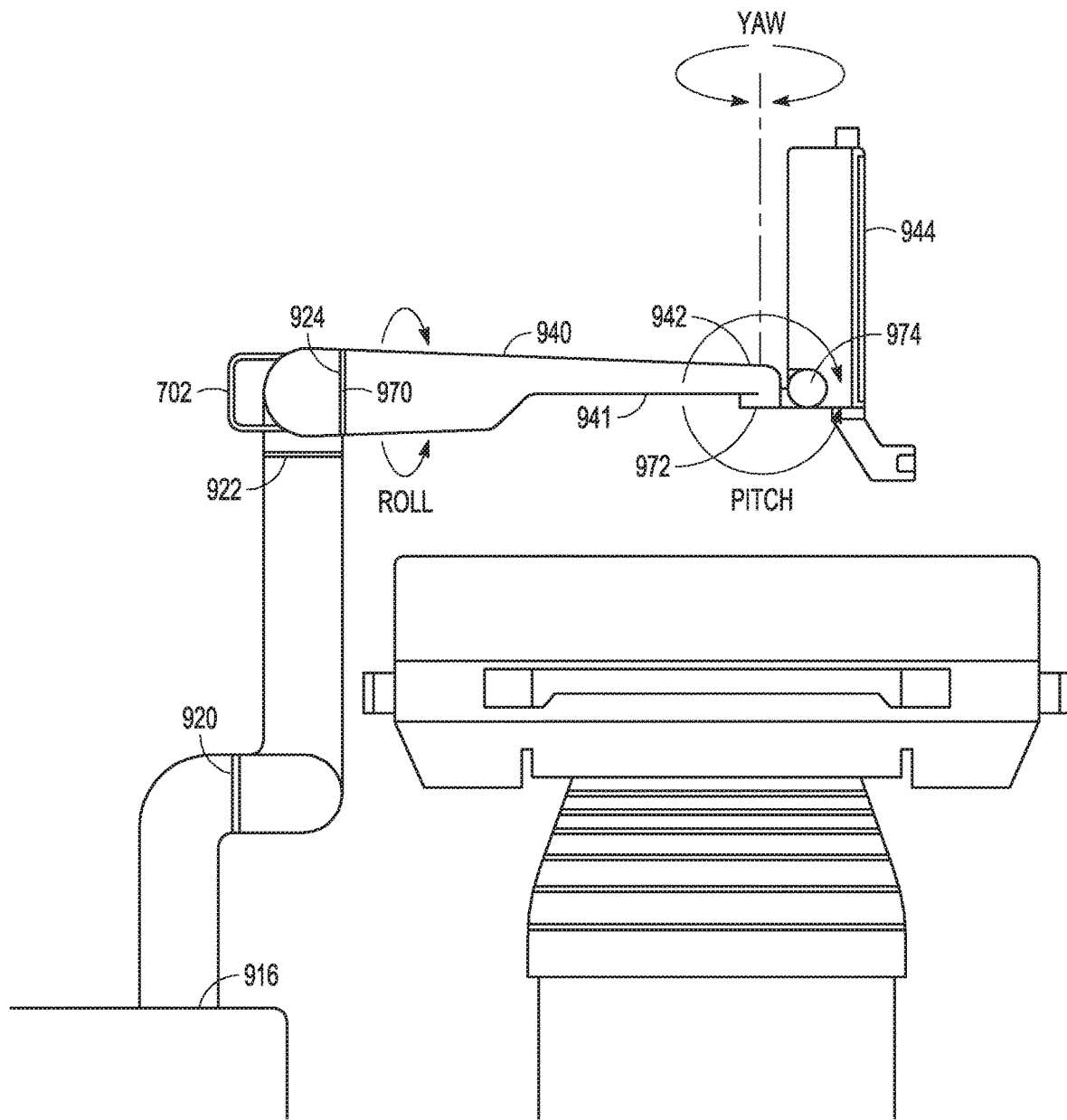
FIG. 9D is an illustration of an arm portion of a manipulating system showing example rotational movement degrees of freedom for a forearm portion.
Figure 9E:
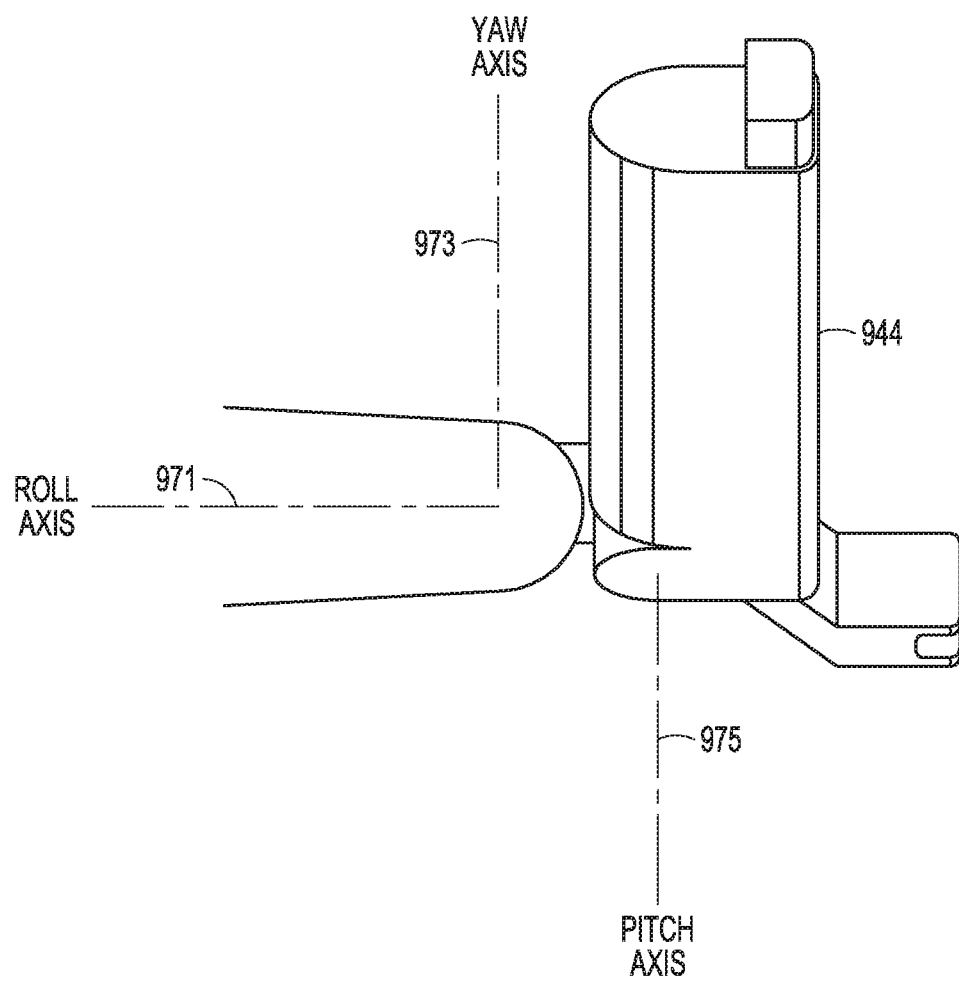
FIG. 9E is a perspective illustration of a portion of the arm shown in FIG. 9D showing a yaw axis, roll axis, and pitch axis.

FIG. 9D is an illustration of a manipulating arm portion of a manipulating system showing example rotational movement degrees of freedom for a distal arm portion. FIG. 9E is a perspective illustration of a portion of the arm shown in FIG. 9D, showing a roll axis, yaw axis, and pitch axis. As shown, the arm may be operated with software control to rotate a defined axis, such as an axis along which a surgical instrument shaft is inserted and withdrawn, at a point that is fixed in space with reference to the base 902 or to another reference frame apart from the manipulating system 900. This point is typically known as a center of motion. And, if the center of motion is located in space away from the arm, then the point is typically known as a remote center of motion. Therefore, the arm (and likewise the manipulating arm shown in FIGS. 2A and 2B, as well as similar manipulating arms) may be operated as a software-constrained remote center of motion manipulator arm. Alternatively, the arm may be operated without software constraining motion around a remote center of motion. Because of the large potential sweep volume of such software-constrained remote center of motion arms, either when operating with a constrained remote center of motion or otherwise, the human-engineered ergonomic features as described herein are especially advantageous for operating such arms in a surgical environment.

The forearm 940 may be configured to rotate at joint 970 around roll axis 971, which may align with a longitudinal axis of the forearm 940. The wrist 942 may include a discrete spar yaw joint 972 and a discrete spar pitch joint 974. The wrist 942 may be configured to rotate at a spar yaw joint 972 around a yaw axis 973. The spar 944 may be configured to rotate at a spar pitch joint 974 around a pitch axis 975, which as shown does not intersect yaw axis 973. The system 900 may manipulate the spar 944 (and a connected item such as a cannula or surgical instrument, not shown in FIGS. 9D-9E) using three degrees of freedom (roll, yaw, and pitch) to achieve a desired cannula orientation. For example, the roll of the forearm 940 around the forearm 940's longitudinal axis, along with spar yaw around spar yaw axis 973 and spar pitch around spar pitch axis 975 at wrist 942, may permit surgical instrument movement in three dimensions and rotation around three axes. It can be seen that the architecture of the arm 904 includes redundant degrees of freedom so that, for example, a cannula mounted to the arm 904 can be rolled along the cannula's longitudinal axis by rotating joints 972 and 974, while at the same time rotating joint 970 and extending column 930 upward to keep the cannula in position. In addition, the base 902 may be movable on the floor along with the various arm joints to enable the spar 944 and its attached instrument or cannula to be positioned at a desired pose to conduct surgery. The arm 904 may include an instrument carriage assembly that translates along the spar 944 to insert and withdraw a surgical instrument mounted on the carriage assembly, as illustrated in FIG. 2D.

The various arm joints (including for example the wrist and translating instrument carriage joints, as well as joints between elbows and large or small links) enable the instrument to be placed in a desired Cartesian six degree of freedom pose during teleoperation. The arm joints may, for example, enable an instrument to pitch, yaw, and roll around remote center of motion at the patient's body wall, and allow the instrument to sway, heave, and surge in 3D space for set up or for other surgical operation, e.g., to manipulate the instrument to a desired position and orientation. The position of the base 902, pose of the arm 904, rotational orientation of the forearm 940, and pitch and yaw orientation of the spar 944 may all be manipulated to achieve a desired position and orientation of a cannula or instrument over a surgical entry site or a desired orientation and position of an instrument at a surgical site within a patient. While the manipulation of system components has been described in reference to the system 900 shown in FIGS. 9A-E, the features and characteristics described may also be applied to the system 200 shown in FIGS. 2A-2J or other systems with similar configuration options.

In the examples shown in FIGS. 9D and 9E, a spar pitch joint may be inside the spar body (or within the space generally outlined by the spar body), and the spar yaw joint may at the distal end of the forearm link. Other configurations of the axes or joints are also possible. For example, a spar pitch axis and spar pitch joint may be at the end of the forearm 940, and a spar yaw axis and spar yaw joint may be inside the spar body (e.g., see FIG. 10, elements 1005 and 1006). Optionally, a roll joint may also be incorporated at an end portion of the forearm 940 or inside the spar body.

Figure 10:
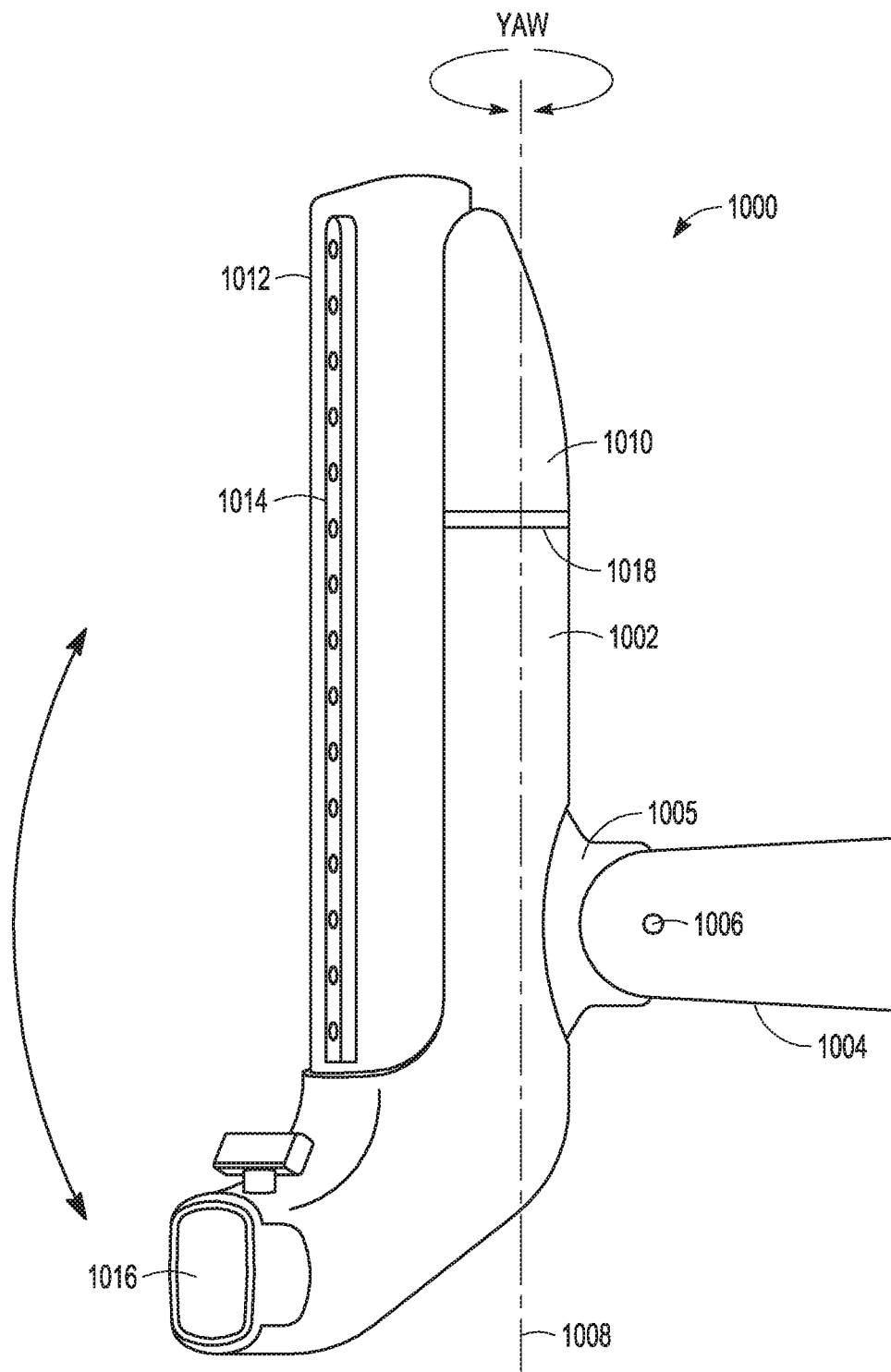
FIG. 10 is an illustration of an instrument mount and telescoping spar.

FIG. 10 is an illustration of distal portion 1000 of a manipulating system. An instrument carriage on which an instrument is mounted is not shown. An instrument mount assembly 1002 may be coupled to a distal portion of an arm 1002 at a wrist 1005, which may have two (or more) degrees freedom, as described in reference to the example wrist shown in FIGS. 9D and 9E. For example, the instrument may rotate around a pitch axis 1006 and around a yaw axis 1008. The yaw axis and yaw joint may be inside the spar body 1010 (e.g., inside a housing portion) of the instrument mount assembly 1002. The instrument mount assembly 1002 may include a spar 1012 on which an instrument carriage is mounted. In various examples, the distal portion 1000 shown in FIG. 10 may be combined to be a part of the system 200 shown in FIGS. 2A-2B (i.e., spar 1012 may be spar 209), or part of the system 900 shown in FIGS. 9A-9C (i.e., spar 1012 may be spar 944), or part of the manipulating system 100 shown in FIG. 1B (i.e., spar 1012 may be spar 124). The spar 1012 may be configured to mount with a surgical instrument carriage and instrument as illustrated in FIG. 2D (e.g., an instrument designed for the da Vinci Xi® surgical system commercialized by Intuitive Surgical, Inc., Sunnyvale, Calif.).

Referring again to FIG. 10, to control instrument insertion and withdrawal, a surgical instrument may be mounted on an instrument carriage that is mounted to the spar 1012. The spar 1012 may telescope to move the instrument carriage, or the carriage may move along the spar 1012 (e.g., along rail 1014), or a combination of both. An instrument such as a cautery tool, cutter, camera, stapler, or grasper may be mounted to the instrument carriage. The instrument carriage may be translated along the rail 1014 to insert or withdraw an instrument with respect to a cannula or patient, as shown and described with respect to FIG. 2D. A cannula (not shown in FIG. 10) may be mounted to the cannula mount 1016. The instrument carriage may be driven by lead-screw (not shown). The instrument carriage may be the distal-most link in a kinematic arm of the manipulating system, and it may be teleoperated, e.g., the movement of the instrument carriage may be controlled via input from user control system 150. The position of the spar 1012 may also be manipulated, as described above, which provides additional range of motion for an instrument during a surgical procedure. The spar body 1010 may include a light feature 1018, which may, for example, indicate an instrument status or type, or a range of motion status, or other information clinically relevant to the distal end of the arm, such as instrument withdrawal from the patient.

Figure 12:
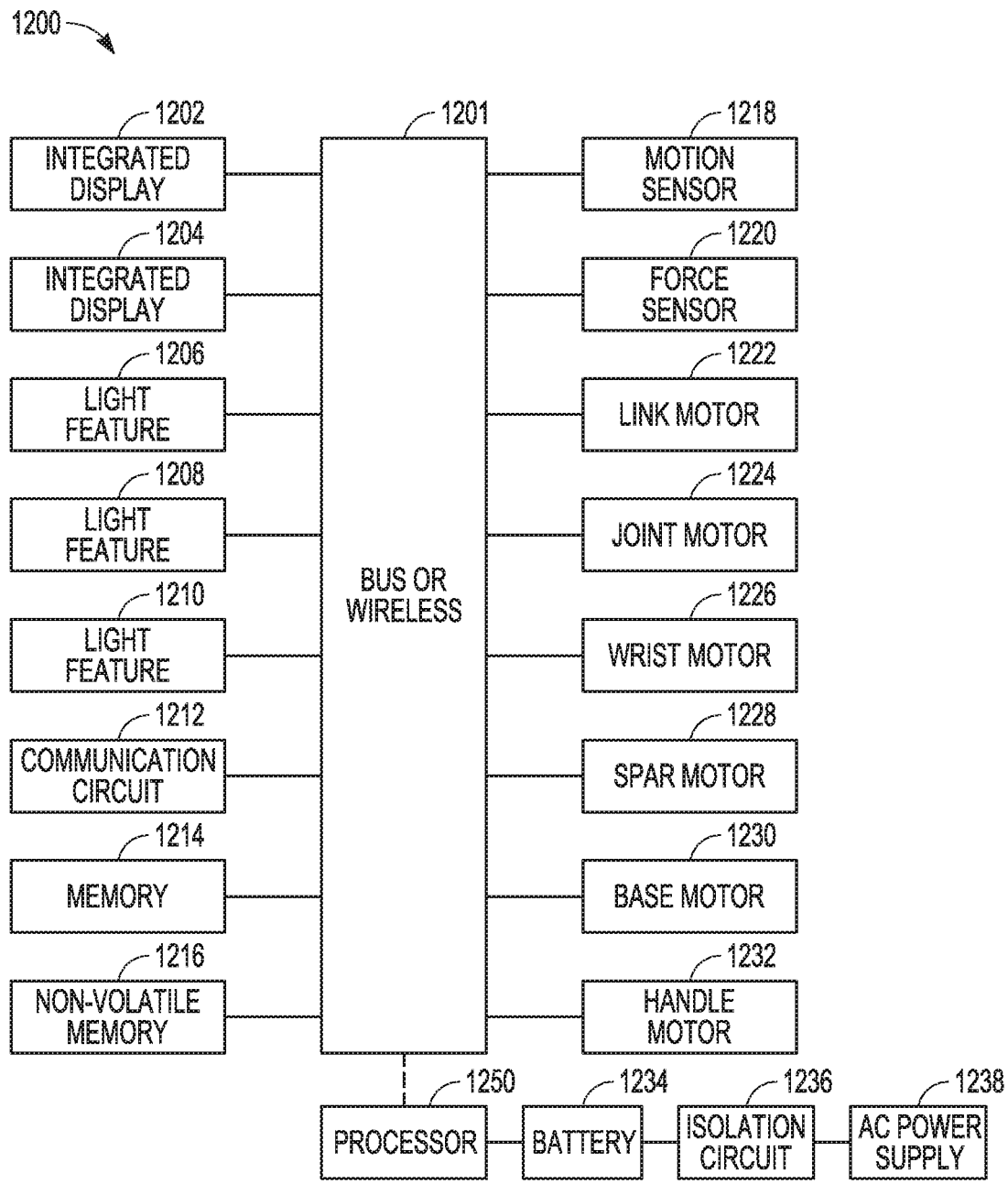
FIG. 12 is a schematic illustration of example components of a manipulating system.

FIG. 12 is a schematic illustration of example electrical component system 1200 of an example manipulating system. These components may be coupled via one or more system wired or wireless connections 1201 that may one or more provide command information, data, or power to the manipulating system. Either centralized or distributed processing may be used to control various system 1200 functions.

The system 1200 may include one or more integrated displays, such as a first integrated display 1202 and second integral display 1204, each of which may be integral with an arm (not shown, see, e.g., FIGS. 2A and 9A) or other component, such as integral display 302 shown in FIGS. 3A-3C or display 402 (e.g., OLED display) shown in FIGS. 4A-4B. The displays may be coupled to the bus or a wireless connection (or both), which may provide (one-way or two-way) command information or data or power.

The system 1200 may also include one or more light features, such as first light feature 1206, which may be at an interface between a column (see, e.g., structural components of FIGS. 2A and 9A, described above) and an arm, a second light feature 1208, which may be at an interface between a column and a link or elbow, and a third light feature 1210, which may be at an interface between a first link or elbow and a second link or elbow. Any of the light features 1206, 1208, 1210 may extend around an interface, and may be controlled by a processor, such as processor 1250.

While one processor 1250 is shown, the system 1200 may include multiple processors, which may communicate, and may be dedicated to specific functions or devices, e.g., a processor may be dedicated to controlling a group of light features, or motors and light features on a particular part of the arm. Processor 1250 may be part of a manipulating system, or may be part of a user control system (e.g., control system 150 shown in FIGS. 1A and 1C) or part of an auxiliary system (e.g., auxiliary system 175 shown in FIGS. 1A and 1D). The processor(s) 1250 may controls (e.g., send control signals) integrated displays, light features, motors, sensor activation, modes, communication signals, or other operations. The processors(s) 1250 may receive and process sensor data (e.g., force sensors, collision detection, clutch functions mode). In some examples, the processor(s) 1250 may also perform other functions (e.g., instrument control or vision).

The system 1200 may include one or more communication circuits 1212, which may for example be or include an antenna or protocol circuit or both. The communication circuit may, for example, be configured to communicate using a Wi-Fi protocol (e.g., 802.11(n)) or another protocol such as Zigbee, Z-Wave, MICS, or Bluetooth. In various examples, the system 1200 may use the communication circuit 1212 to communicate with one or more system components (e.g., integrated displays, light features, motors, etc.) or with a second manipulating system or with a user control unit via wired or wireless communication connection.

The system 1200 may include a memory circuit 1214 and a non-volatile memory 1216, both of which may also be centralized or distributed. Various information such as application or operating program, user preferences, user profiles, heights (e.g., user height), calibration information (e.g., sensor calibration data), system tuning or operation information, poses (e.g., pose configuration information such as IV, transport, ready to drape, and ready to dock poses), historical use information, session information (e.g., duration of a surgical session, or movement or orientation or position history), login or authentication (e.g., username and password) information, or other information may be stored in the memory circuit 1214, non-volatile memory 1216, or both.

The system 1200 may include one or more motion sensors 1218 or force sensors 1220, or both, or similar user presence or input sensors, any of which may, for example, provide input for control of light features, motors (described below), or other system components or features.

The system 1200 may include a link motor 1222, which may control a movement of a link or other component, such as a translational movement of a link with respect to a component (e.g., column), or a translation (e.g., telescope) of a column with respect to a base.

The system 1200 may include one or more joint motors 1224 (e.g., one joint motor for each degree of freedom of each joint of an arm), which may, for example, be configured to adjust an orientation of a joint responsive to a command received from a processor (e.g., processor 1250). For example, a joint motor 1224 may change a relative orientation of two links, e.g., rotate an arm link with respect to an adjacent component. As an example, a joint motor 1224 may rotate a forearm as described above.

The system 1200 may also include one or more wrist motors 1226. For example, a system 1200 may include a first wrist motor configured to adjust a pitch of a spar relative to a forearm link and a second wrist motor configured to adjust a yaw angle of an instrument mount relative to the forearm link.

The system 1200 may include one or more base motors 1230 that may be configured to move a base. For example, a base motor may be configured to roll, turn, or otherwise move a wheel, roller ball, or other component to drive the base across the floor or otherwise move the base as described herein. In some examples, a system may include one base motor coupled to each wheel or roller ball, or a motor may be coupled through a drive system (not shown) to two or more wheels or roller balls.

The system may include a handle motor 1232, which may be configured to change an angle or orientation of a handle or extend or retract a handle as described herein.

The names of the motors are arbitrary and are provided for purpose of explanation. For example, a system may include a motor configured to adjust a pitch angle or yaw angle of an instrument mount that is not in or at a wrist.

Any or all of the motors or light features or displays may be communicatively coupled to a processor (e.g., processor 1250) and may be configured to execute instructions or respond to signals from the processor (e.g., move or lock or change speed or light up or dim or change color or pattern).

The system 1200 may also include one or more power sources such as a battery or capacitor or AC power supply (e.g., configured to connect to a wall outlet). A battery 1234 may provide power to the light features, motors, sensors, processors, or other components. The battery 1234 may be rechargeable. For example, an AC power supply 1238 may provide power to a rechargeable battery 1234 that may provide DC power to any of the components described above. Alternatively, the system 1200 may run on AC power. In an example, the AC power supply may step down wall outlet power to provide low voltage AC power to lights, motors, or other components. In some examples, the system 1200 may include one or more isolation circuits 1236 that may isolate the system 1200 from a line power source or wired data connection, which may protect the patient from a power surge through a power line or data line (e.g., network cable).

Light Features

One or more light features such as a lighted ring may be incorporated into an arm. For example, a light feature may be incorporated as a thin ring at a joint between two links (e.g., joints as shown in FIGS. 2A-2I, 3C, 5A-5B, 6A, 7A-7B, 8, and 9A-9D). A light feature may also be a wider ring. A light feature may include a light pattern, light color variation, or animation. In some examples, a light feature may be a short link, or it may be part of a short link, which may be between two main structural links of an arm or other manipulating system assembly. A light feature may be, or be part of, a handle, helm, or other manipulating system component. A lighted ring may be a dedicated display link as described above. Alternatively, a lighted ring may be output on a controlled display, such as a controlled display on a dedicated display link (see e.g., FIGS. 4A and 4B, display 402).

A light feature may be controlled locally by a processor in a manipulating system, or it may be controlled by a separate computer processing system that also controls other devices or features in a teleoperated surgical system (e.g., user control system 150 or auxiliary system 175 shown in FIG. 1), or by a combination of a computer in the manipulating system and a second computer. A light feature in a modular manipulating system may be controlled in coordination with a larger system (e.g., with da Vinci xi® surgical system).

In various examples, a light feature may be controlled responsive to a user input (e.g., from a clinician), or by a processor responsive to a manipulating system event, state, or operating mode. A light feature may provide a communication to a clinician or amongst clinicians (e.g., a communication from a surgeon to a nurse, or vice versa, during a teleoperated surgical procedure). A light feature (e.g., rings) may include various visual aspects, which may communicate a status, identity, alert, instruction, or other information to the user or another person associated with operating a manipulating system. In some examples, a system may include a light sensor, and the brightness, color or other appearance of a light feature may be adjusted based at least in part on input from the light sensor (e.g., adjusted based on a level or quality of ambient lighting).

Example Light Feature Patterns

Light features and patterns displayed by light features are generally arranged in accordance with the shape of the object on or about which they are located. As examples, various light features and patterns described herein are in accordance with circular objects in support of the various described human-engineered manipulating system features. Other light feature shapes and patterns may be used, however, to closely visually integrate a light feature with the overall human-engineered considerations of a manipulating system component or location. For example, light features may be generally rounded (e.g., circular, oval, etc.) or generally polygonal (e.g., square, hexagonal, octagonal, etc.) rings. Light features may be closed or open geometries, and they may extend more than 360 degrees around an object. In some examples a light feature may extend around two or more objects, such as around two columns extending from a base. And, light features may be linear or curvilinear, such as in association with translational motion of an object. Further, two or more light features may be combined to form a single light features (i.e., a light feature may include two or more discrete subfeature components). Visual patterns displayed by light features are in accordance with the shape of the light features (e.g., a curving pattern on a rounded light feature in association with a rotational motion, a linear pattern on a straight light feature in association with translational motion, etc.). The following description of light feature visual patterns applies to both a single light feature and to a light feature with discrete subfeature components, both of which may display a visual pattern that may be continuous (e.g., a continuous line) or that may include discrete visual elements (e.g., a dashed or dotted line). Therefore, various visual patterns are described, and skilled persons will understand that the visual patterns describe light features of both types, so that the term light feature pattern applies to both the visual display perceived by a viewer and the physical arrangement of a particular light feature.

Figure 13:
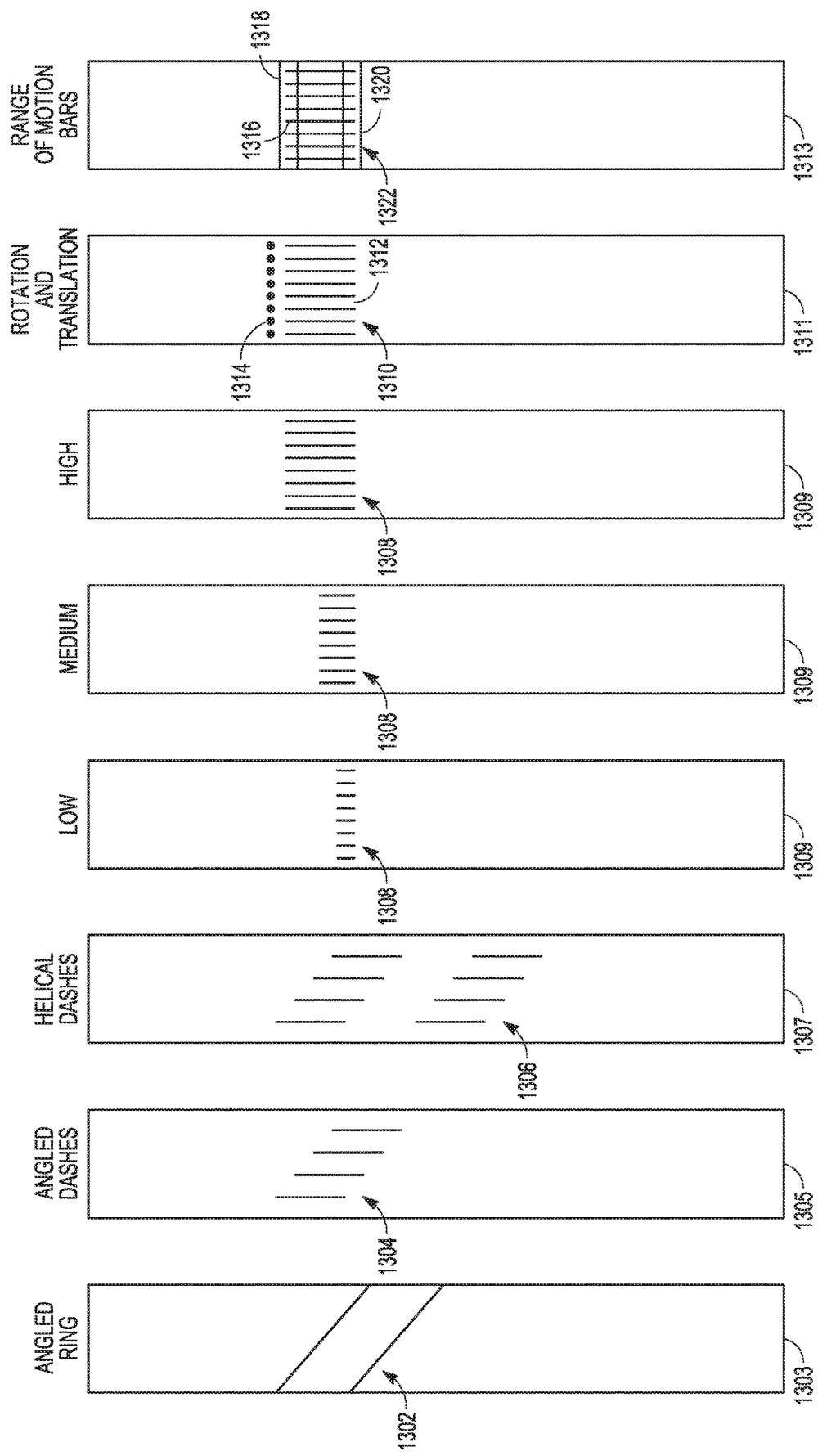
FIGS. 13A-H are an illustration of aspects of example light feature patterns.

FIG. 13 is an illustration of aspects of example light feature patterns, which may be applied to light features such as rings. As shown in FIGS. 2A-2J, 9A-9C, and other FIGS. a light feature may include a light ring pattern, which may extend circumferentially part way or all the way around an interface portion of a teleoperated surgical system.

Various light feature shapes and visual patterns are possible, and the aspects of the light feature pattern may communicate information to a user. Light features and visual patterns may extend directly across a component, or they may extend at an oblique angle (such as an oblique angle relative to a long axis of an arm link). FIG. 13A shows an example light feature pattern 1302 that extends at an oblique angle around a system component (e.g., arm) 1303. FIG. 13B shows a light feature pattern 1304 that includes discrete subfeature patterns that extend around a system component 1305 in an oblique angle pattern similar to light feature pattern 1302. As shown, the light feature pattern 1304 includes subfeature patterns that are short, straight lines ("dashes") aligned with component 1305's long axis. A light feature may extend helically around a system component. FIG. 13C shows an example light feature pattern 1306 that includes dashes similar to those described for light feature pattern 1304 and that extend around a system component 1307 in a helical pattern larger than 360 degrees.

In some examples, a light feature pattern may transition from a solid feature pattern (e.g., continuous ring) as shown in FIG. 13A to an interrupted feature (e.g., dashed ring) as shown in FIG. 13B to indicate a state change, such as a clutch mode (described below) or movement state (e.g., locked or unlocked joint). In some examples, a light feature pattern may transition from a single line or set of dashed lines to a double set or continuous helix as shown in FIG. 13C to communicate a state change (e.g. change in range of motion or motion speed or degrees of freedom).

In some examples, a size of a light feature pattern (or size of illuminated portion of a light feature pattern) may change to communicate information to a user. For example, FIG. 13D shows a component 1309 with a light feature pattern 1308 in a first state in which the light feature pattern has a first (small) dimension, FIG. 13E shows the light feature pattern 1308 in a second state in which the light feature has a second (intermediate) dimension that is larger than the first dimension, and FIG. 13F shows the light feature pattern 1308 in a third state in which the light feature has a third (large) dimension that is larger than the first and second dimension. The first, second, and third states may communicate, for example, an amount of displacement (e.g., translational displacement or angular displacement) of a joint. The light feature pattern 1308 may also be animated or change color, e.g., the length of the segments in the light feature pattern 1308 may grow longer (e.g. progress smoothly from the state shown in FIG. 13D to 13E to 13F, or vice-versa) as a joint moves. In some examples, the length of the segments may indicate translation of a component (e.g. telescopic movement of one part relative to another), and a rotational movement or color or other visual state change may indicate rotation.

In some examples, different aspects or elements of a light feature may indicate different quantities or types of information about movement of a joint near the light feature, such as rotational and translation motion at the joint, or range of motion. In light feature pattern 1308, for example, successive dashed subfeature patterns may illuminate to indicate a rotational joint displacement, and the subfeature patterns may also increase in length to indicate a translational joint displacement. And, light feature pattern 1308 as a whole, or particular subfeature patterns, may change color, blink, and the like to indicate information such as joint ROM limit, target joint displacement for manual movement, manipulator system or component status, etc. Persons of skill in the art will understand that various light feature patterns may be similarly modified, such as a light feature ring pattern illuminating along its arc to indicate rotational joint displacement and becoming wider to indicate translational displacement, optionally changing color or color pattern in association with rotational or translational displacement to convey information to the user. And as shown in FIGS. 13D-13F, a linear light feature pattern change may be associated with a rotational joint displacement (e.g., longer corresponds to position in rotational ROM).

FIG. 13G shows component 1311 with an example light feature pattern 1310 that has a first subfeature pattern element 1312 (e.g., bars) and a second subfeature pattern element 1314 (e.g., dots). In an example, the first element 1312 (e.g., bars that increase and decrease in length) may correspond to a first type of motion (e.g., translation in the direction of the bars) and the second element 1314 may correspond to a second type of motion (e.g., rotation around the direction of the dots). An aspect of the first element 1312 (e.g., length of bars or thickness of bar or color or brightness or position) may change to indicate an amount of movement or a rate of change of position (e.g., speed of movement). An aspect of the second element 1314 (e.g., size of dots or color or intensity or position) may change to indicate an amount of movement or rate of change of movement.

FIG. 13H shows a component 1313 with an example light feature pattern 1322 having a displacement light feature pattern 1316 (e.g., one or more displacement bars) that may indicate an amount or rate of movement (e.g., length of displacement bar(s) may indicate an amount of movement). A first range of motion light feature pattern 1318 may indicate a first range of motion limit for a joint. A second range of motion light feature pattern 1320 may indicate a second range of motion limit for the joint. The first and second range of motion limits may be opposite ends of the same range of motion for the joint (e.g., top and bottom of a translational displacement), or they may two different types of motion (e.g., rotational and translational) for a multi-DOF joint. In an example, the length of the displacement feature 1316 may increase (e.g., displacement bars get longer) as a component or portion of a system (e.g., arm link or arm joint) moves, and first and second ranges of motion (e.g., rotational limits or translation limits) may be indicated by relative position of the ends of the feature (e.g., top or bottom of the bar) relative to the range of motion features 1318, 1320. In some examples, an aspect of one or more of the light features 1316, 1318, 1320 may change color, brightness, or intensity, or start to flash to indicate that a movement is near an end of a range of motion (e.g., yellow) or at an end of a range of motion (e.g., red).

Any of the examples shown in FIGS. 13A-H may be combined together (e.g., angled examples may have variable width or length), or they may be combined with a controllable color state (such as the examples described below) or animative state (e.g., light feature pattern motion may indicate joint motion or flashing may indicate a state or state change).

The aspects of light feature patterns shown in FIGS. 13A-13H and described below may be combined with any of the systems, methods, and features described above or below. The example descriptions below are described as "rings" merely as illustrative examples. The aspects of ring examples apply to other light feature pattern shapes. One aspect is the way the light features are integrated with the design of the arm, e.g., mechanically seamless, and visually positioned at a location on the arm relevant to the information the light feature is communicating. For example, a light feature (e.g., ring) may be positioned at an interface between components (e.g., at a joint between a link and an elbow or another link.

Light Features on an Orienting Platform

Figure 16:
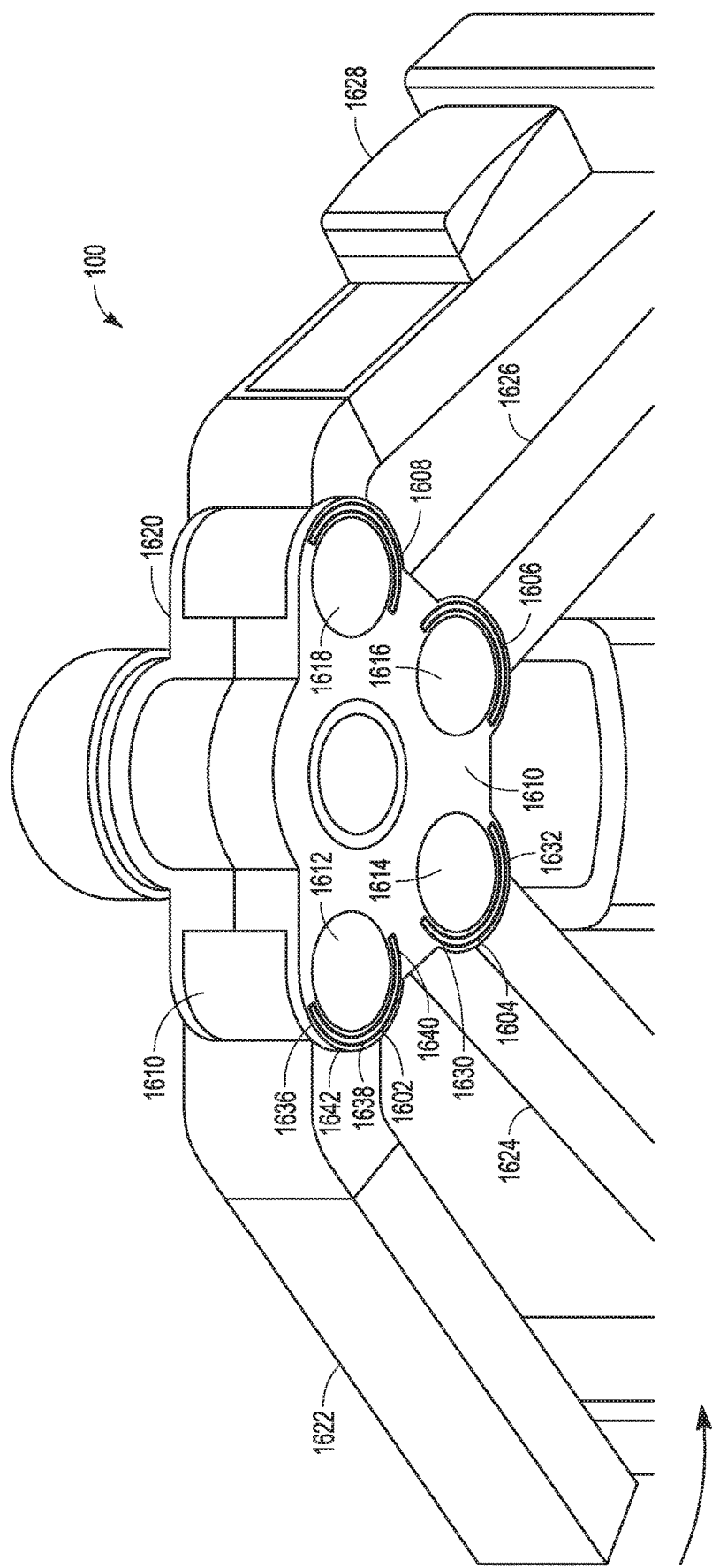
FIG. 16 is an illustration of an example manipulating system with light features.

FIG. 16 is an illustration of an example manipulating system 100 modified with one or more light features. As shown, four manipulator arms are coupled to a single orienting platform, which is in turn supported by another arm that extends from a mechanically grounded base (not shown). The manipulating system 100 may be the system 100 shown in FIGS. 1A and 1B, modified as described herein. The manipulating system 100 may include a light feature 1602 at a flex joint 1612 where a first arm 1622 meets an orienting platform 1620. The flex joint 1612 may be a joint where an arm couples to the orienting platform 1620, and it may be a pivoting joint that allows the arm to rotate around the orienting platform 1620. Other types of flex joints are also possible (translation, spherical, etc.).

The light feature 1602 may align with (e.g., extend around) the flex joint 1612 on an underside 1610 of the orienting platform 1620 so that it is visible to a clinical user looking up at the orienting platform while moving the arm 1622. The light feature 1602 may, for example, extend partially or fully around a pivot part that couples the arm 1622 to the orienting platform 1620.

In some examples, an aspect of the light feature 1602 may indicate a characteristic of the arm position, such as a desired joint displacement location, an undesired joint displacement location, or a moderately desired or acceptable joint displacement location. An a light feature pattern appearance scheme may include a number of appearance states that correspond to the desirability of arm placement. For example, the system 100 may use a color-coded scheme (e.g., with color-changing LED panel), where red indicates an undesired placement, yellow indicates a moderately desired placement, and green indicates a desired placement.

In some examples, the light feature pattern 1602 may have a consistent visual appearance throughout the light feature 1602. For example, the light feature 1602 may be green, or may be yellow, or may be red. The visual appearance may be based upon the position of the corresponding arm. For example, if the arm 1622 is in a desirable position, the light feature 1602 may have a first appearance, and if the arm 1622 is in an undesirable position, the light feature 1602 may appear red. The light feature pattern may change based upon movement of the arm. For example, responsive movement of the arm 1622 from an undesired position to a moderately desired position, the light feature pattern 1602 may change from the first appearance (e.g., red) in the undesired position to a second appearance (e.g., yellow) in the moderately desired position. And responsive to further movement of the arm 1622 to a desired position, the light feature pattern 1602 may change from the second appearance (e.g., yellow) to a third appearance (e.g., green) in the desired position. The correspondence of visual appearance to arm position may guide a user in choosing an arm position based at least in part on desirability of the position indicated by the light feature.

In some examples, the light feature pattern 1602 may have an appearance that is not the same throughout the light feature. For example, a variation appearance (e.g., color difference or brightness) across a light feature may communicate a desirability of a range of positions. For example, a first portion 1636 of the light feature 1602 may have a first appearance (e.g., red), which may indicate that the location of the first portion 1636 corresponds to an undesirable position (e.g., potential collision with another arm coupled to the orienting platform, or another arm from a second manipulating system), a second portion 1638 of the light feature 1602 may have a second appearance (e.g., yellow), which may indicate a moderately desired (e.g., acceptable but not ideal) position, and a third portion 1640 of the light feature 1602 may have a third appearance (e.g., green) which may indicate a desired position. In some examples, the light feature pattern may include additional discrete light portions (e.g., six, twelve, eighteen, or more), which may each have a different appearance (e.g., e.g., shades of green, yellow, or red, or blends thereof).

The first arm 1622 may include an indicator 1642, which may be near the light feature 1602 to allow for observation of the relative position of the indicator relative to the light feature 1602. The indicator 1642 may correspond to a portion on the light feature pattern, which may indicate the desirability of the position of the arm 1622. For example, the indicator 1642 may align with a portion of the light feature 1602 having a second appearance (indicating a moderately desired position), and movement of the arm 1622 counterclockwise (as indicated by the arrow) may move the indicator 1642 toward the third portion 1640 of the light feature 1602. The alignment of the indicator 1642 with the third portion 1640 may indicate that the arm 1622 is in a desired position (e.g., a position with a low risk of collision).

In various examples, the indicator 1642 itself may be light feature, or it may be unlighted. In some examples, the indicator 1642 may have a variable light feature pattern appearance that may be controlled match the appearance of the indicator 1642 to the appearance of a corresponding portion on the light feature pattern 1602 in order to reinforce the information conveyed to the user. For example, when the indicator 1642 is in a "green zone" (adjacent a green portion of the light feature 1602), the indicator 1642 may be green, and when the indicator 1642 is in a "red zone" (adjacent a red portion of the light feature 1602), the indicator 1642 may turn red.

The system 100 may include a second light feature 1604 at a second flex joint 1614 for a second arm 1624. In some examples, the desirability of an arm position and the corresponding appearance a light feature (e.g., green, yellow, red) may depend on a position relative to an adjacent arm (e.g., the appearance of the second light feature may depend upon the position of the second arm 1624 relative to the first arm 1622).

In some examples, the indication of desirability of an arm position may be based at least in part upon the potential for a collision with an adjacent arm. In this context, a collision may not be a physical collision (which may be prevented by the system or a related control system), but rather may be additionally or alternatively include a state in which one or both arms are prevented from movement in a direction to avoid a possibility of a physical collision. A desirable position of an arm may correspond to a position in which the arm is unlikely or least likely to experience a collision with an adjacent arm (e.g., based upon satisfaction of one or more collision avoidance criteria, when a calculated collision potential is below a threshold), and an undesirable position may correspond to a position in which a collision is somewhat more likely than in the desirable position (e.g., one or more collision avoidance criteria not satisfied, or a calculated collision potential is above a threshold). The potential for a collision may be based on one or more collision avoidance criterion, such as a spacing of adjacent arms (and optionally including spacing of attached instruments) or an anticipated range of motion needed to perform a procedure.

Thus the information conveyed by various light feature patterns on a manipulating system may be dynamic, so that a first light feature conveys information not solely about an associated system component (e.g., a first joint or other corresponding system component), but also depending on the state of one or more second components in the manipulating system or in a second manipulating system. And, a light feature corresponding to the one or more second components may also indicate that those second one or more other components are associated with the information conveyed by the first light feature. For example, if a first arm is in position to collide with a second arm, a first light feature associated with the first arm indicates the potential arm collision problem by flashing, then a second light feature associated with the second arm also flashes to alert the user that the second arm is the potential collision problem. Collision potential is merely an example of the many dependent states between two or more system components that may be indicated by light features associated with each of the two or more system components. This visual information assists the user to determine which system components are involved with a particular situation so that the user can modify a system configuration accordingly.

The system may 100 also include a third light feature 1606 at a third flex joint 1616 for a third arm 1626, and a fourth light feature 1608 at a fourth flex joint 1618 for a fourth arm 1628. The third light feature 1606 and fourth light feature 1608 may indicate a status or state (e.g., desirability of position) as described above.

In some examples, a light feature may indicate desirable of position relative to two adjacent arms. For example, a first portion 1630 of the second light feature 1604 may indicate the desirability of the position of the second arm 1624 relative to the first arm 1622, and a second portion 1632 of the second light feature 1604 may indicate the desirability of the second arm 1624 relative to the third arm 1626. In an example situation, the first portion 1630 may be red, indicating that the first arm is too close to the second arm, and the second portion 1632 may be green, indicating that the third arm 1626 and second arm 1624 are in a desirable placement (e.g., unlikely to experience a collision). In such a scheme, a user may be guided by the light features to position arms so that each light feature indicates a desirable position (green) or acceptable position (e.g., yellow) throughout the light feature.

While various examples above have been described in terms of a color scheme (e.g., red, yellow, green) for purpose of explanation, other light feature pattern schemes are also possible, such as a brightness scheme (e.g., bright indicates desired placement and dim indicates an undesired placement) or a flashing or pulsing scheme (e.g., fast flashing indicates desired placement and slow flashing indicates undesired placement) or a motion scheme (e.g., light feature pattern animation movement in a clockwise direction indicates the desired position is in a clockwise direction, in a counter-clockwise direction indicates the desired position is in a counter-clockwise direction, no movement indicates the desired position, and the speed of animated movement may optionally indicate a proximity to the desired position). In some examples, two or more light feature pattern schemes may be combined (e.g., a color scheme may be combined with a motion scheme or a flashing or pulsing scheme). In some examples, the scheme may be user-configurable. While the light features have sometimes been described as having discrete portions for the purpose of explanation of the examples illustrated by FIG. 16, any of the light features described herein may also be continuous, or may appear to be continuous (e.g., using a multiplicity of discrete LEDs or other light elements), and the light feature may have discrete regions with different appearances (as described above), or the light feature may appear to have a continuously changing appearance across its length (e.g., gradually blending from green to yellow to red).

Physical Construction and Appearance of a Light Feature

A light feature may include a plurality of lights that together form a light feature, such as a light ring. For example, a light ring may include a number (e.g., forty (40)) of light emitting diodes (LEDs), which may be under a cover (e.g., transparent, translucent, or micro-drilled cover), and may form a light feature having either a continuous or a segmented appearance. In some examples, a light feature may include LEDs of different colors to enable changing of the color of the light feature, or to enable a variation in the color across a light feature (e.g., one portion of the light feature may be red, a second portion of the light feature may be green, and a third portion between the first and second portions may be yellow).

A light feature may be designed to "disappear," as described above with the integral display. For example, a ring may be formed from a translucent material (e.g., plastic or CORIAN®) and has an appearance that matches the adjacent structure when not lit. In another example, a ring may be formed from a plurality of small holes that transmit light. The holes may be in front of a light display (e.g., LED array). A process such as vacuum metalizing may be used to give ring a metallic appearance when not lighted, which may also be used to integrate the visual appearance of the unlit ring into the human-engineered overall visual appearance of the manipulating system.

A light feature may be formed in the shape of a ring that extends at least part way around a portion of a medical device. A light ring is not necessarily circumferential. For example, a light ring may be circumferential, helical, a double-helix, or asymmetric. In some examples, a light ring may be or include one or more arc segments. In various examples, a ring may be thicker (e.g., 2 cm or 5 cm or 10 cm) or thinner (e.g., 1-3 mm) than shown in FIGS. 2A-J or 9A-9C.

A light ring (or other light feature) may extend fully around an interface or arm, or a ring may extend only partially around an arm or interface. In various examples, a light ring may be continuous or broken. For example, a ring may appear to be a single continuous strip, or a ring may be or appear to be a series of discrete lights. For example, a ring may be formed of a plurality of dots, dashes, lines, icons, or other patterns. In some examples, discrete light elements that form a ring may sequentially light up so that one or more lighted portions appear to move along the ring (e.g., run around an interface or transverse to an interface).

In some examples a light ring may extend around a portion of a manipulating system base, or all the way around (as shown, for example, in FIG. 9A), so that the light ring is at the interface between the base and the floor or other mechanical ground. Such a base-ground interface may be used to indicate information such as "system is ready to move" or "system is braked to remain in place". And, lighted portions of a base-ground interface may indicate directional movement such as flashing green in a particular direction and solid red in other directions. Similarly, a light ring may be at the bottom of column extending from a base (as shown in FIG. 9A), or at the top of a column where a manipulating arm is coupled (as shown in FIG. 2A).

In some examples, a light feature may be a touch point or control input device (e.g., touch sensitive button), or it may be adjacent to or integrated with a touch point or control input device.

In some examples, an input device such as a control button may be integrated into a light ring or other light feature. For example, a light ring may include a real (e.g., button) or virtual (e.g., touch screen) input that is configured to receive an input from a user, such as a button press, finger slide, or other touch input. In various examples, a manipulating system operating mode, arm clutch state, or direction of movement may be input by using the input device.

Figure 20A:
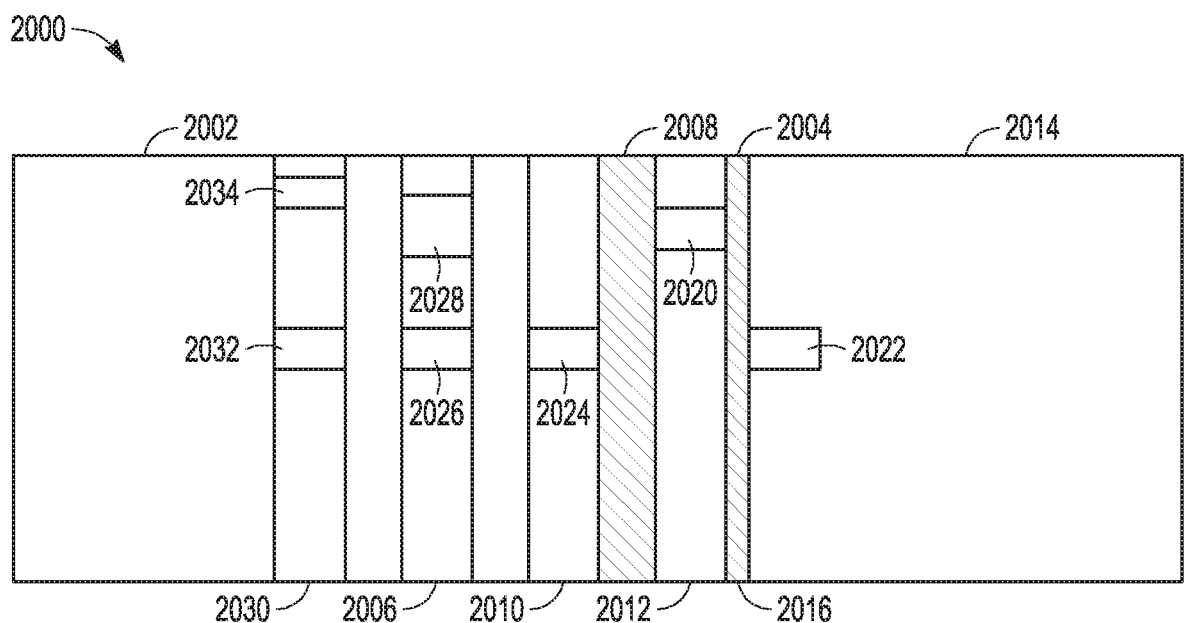
FIGS. 20A-20B are illustrations of a medical device that has light features.
Figure 20B:
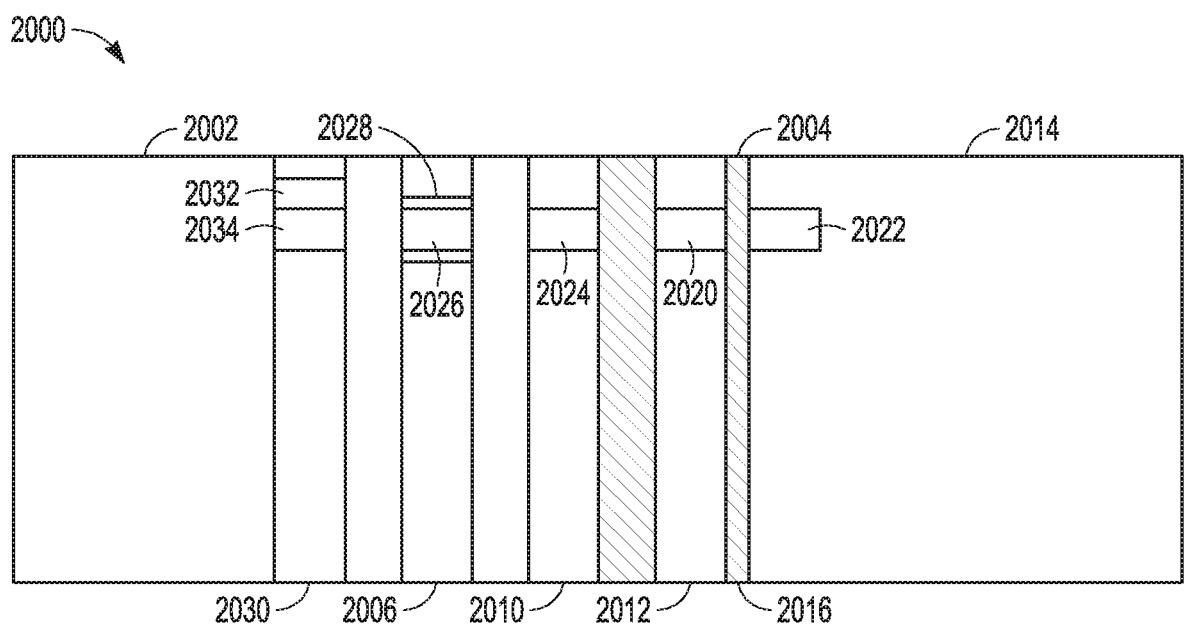

Light features may be set off from other structures by a visual boundary member, such as a metal ring (e.g., a visual appearance consistent with a the visual appearance of other significant locations (e.g., handle) on the manipulator system so that the human-engineered visual appearance of "this is an important location" is consistently communicated to a user). For example, FIGS. 20A-20B show an illustration of a medical device 2000, such as a manipulator arm, in which a second arm portion 2014 may be visually set off from a light feature 2012 by a first border 2004. The first border 2004 may, for example, be a metal ring between the light feature 2012 and the second arm portion 2014. The device 2000 may include a second light feature (e.g., ring) 2010, which may be visually set off from the first light feature 2012 by a second border 2008. The first border 2004 and second border 2008 may be, for example, be formed of machined polished aluminum and may optionally have an appearance consistent with the polished handles described above.

In some examples, a controllable display may output a light feature pattern similar to the physical characteristic of another light feature. As shown in FIG. 4B, for example, a light strip may be illuminated on the display to simulate the appearance of a light feature ring, which optionally is at another location on the system. In this way two or more different light feature types may be configured to output a consistent light feature pattern in a system, and so ensure consistent human-engineered user interaction features in the system.

Visual Aspects of Light Features

Various visual light pattern features may be applied to a light feature. For example, a light feature pattern may change color. brightness, or shape. In some examples, a light feature (e.g., ring) may include a time-varying feature. For example, a light feature may change color or brightness, or a light feature may flash, pulse, "breathe" (e.g., slowly shift brightness on and off), or display according to a time pattern. In some examples, a light feature pattern may pulse with discrete on/off pulses, which may follow a continuous or intermittent square wave pattern, and which may create a strobe or flashing effect. In some examples, a light feature pattern may be controlled to provide a continuous transition from bright to dim or off (e.g., follow a sine wave or saw tooth pattern), which may create a "breathing" visual effect.

In some examples, a light feature pattern may flash, pulse, or otherwise change to indicate direction (e.g., to indicate a rotation or translation). For example, a light feature pattern may indicate a direction by sequentially lighting one or more segments (e.g., LEDs or groups of LEDs) to create the appearance that a lit portion moves along the light feature, or that one or more lit portions follow ("chase") a lead lit portion that moves along the light feature.

When a system is powered on, a startup effect may be presented on all or some of the light features of the system. For example, two or more light features may be lit in sequence (with overlapping or non-overlapping lit times) along the system for a defined duration, which may create an appearance of energy or light traveling or "washing" over the system, and may appear to "bring the system to life" as the system starts up. In various examples a color change or pattern, brightness change or pattern, pulse pattern (e.g., one or more flashes), or any combination thereof may be used to indicate system startup. The completion of such an effect may indicate that a startup process is completed (or has started).

Figure 17:
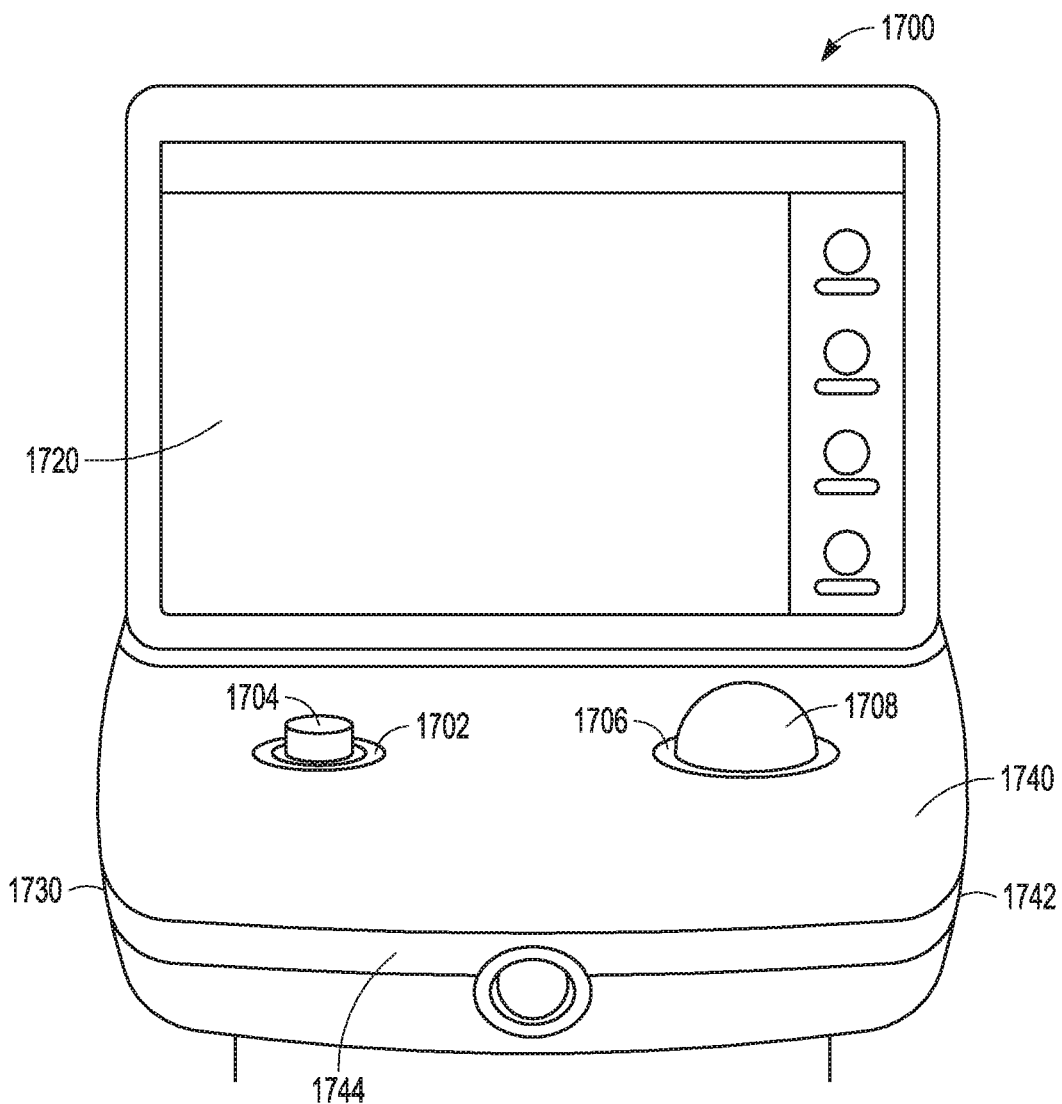
FIG. 17 is an illustration of a user control unit.

In some examples, a device may include one or more sensors configured to sense a user's presence (e.g., a contact, proximity, camera, motion sensor, or other presence sensor), and responsive to detection of a user (e.g., the user's hand on or near the light feature), the appearance of a light feature may change (e.g., brighten or change color). In various examples, the sensor may be next to, on, or under a light feature (e.g., so the system can detect a user's presence near the light feature). In some examples, a light feature may turn on, brighten, or change color when a user is detected. In some examples, a light feature near a user control input may light up to alert the user of proximity or contact with the control input. For example, as shown in FIG. 17 a light feature 1702 may turn on as a user's hand comes close to control input 1704, and likewise light feature 1706 may turn on as the user's other hand comes close to control input 1708. In this way the user is alerted that the system is operating and is ready. Optionally, a light feature may turn on in one color (e.g., red) if the system is not ready to receive an input at the associated control input device and in another color (e.g., green) if the system is ready to receive an input a the associated control input device. In some examples, a light feature may change appearance to alert a user that he or she is near a pinch point or other potentially injurious location. For example, a system may use joint sensors, awareness of the position or orientation of system components (e.g., arm links) to determine the location of a pinch point (e.g., a pinch within an arm, or a pinch between an arm and another object such as a surgical table), and the existence or location of the potential pinch point may be identified with a light feature (e.g., identified by color or other appearance change continuously, or responsive to detection of a user near the potential pinch point).

In some examples, a single light feature may include one or more sections that are visually different (e.g., brighter or a different color) from other portions of the light feature, as shown for example in FIGS. 20A and 20B. In some examples, the visually different section may change color, or move in the direction of a detected touch point, or both.

In some examples, a system may detect when a user is near the system or a specific part of the system. Responsive to detection of a nearby user, a system may increase the brightness of a light feature. For example, when a user is close to a system, the system may increase the brightness of one or more lights that are closest to the user to illuminate a work area on the system or nearby.

A system may control light features in response to detected sound. For example, a system may change the appearance (e.g., brighten or change color) of a light feature in the proximity or direction from which it senses a sound, such as a voice command. Indicating a direction of a received voice command may inform a user which of a plurality of sounds or voices the system is treating as a command or input. For example, if a first user is at a first side of a system and a second user is at the opposite second side of the system, and both users are giving voice commands to the system, one or more light features light or otherwise indicate which user's voice is being received as a command input.

Light feature patterns may be customized or personalized. For example, a user's color preference, brightness preference, or motion preference may be applied and saved for one or more light features. In some examples, a specified light feature may be defined for an identification purpose. The identification light ring optionally may not be used for other usability features (e.g., a particular ring may optionally not be used to communicate system status). An identification light feature may facilitate identification of an individual system in a facility such as a hospital (e.g., a system that has a green identification light feature may be distinguishable from a system that has a blue identification light feature). In some examples, an identification light feature may associate a system with related systems or sub-systems. For example, a control unit, manipulator unit, or auxiliary unit may be configured to work together as a system and are therefore visually identified as related based on an identification light feature (e.g., two or more related units may present a specific color, such as green, using the identification light feature). In some examples, two units may be modular or usable with various systems, and may be paired or otherwise configured to work together, and the two units may present an identical or similar appearance (e.g., blue) on a light feature to indicate their related status. In some examples, a manipulating system identification light feature may change color or otherwise visually indicate a change of control from a first control unit to a second control unit. For example, an identification light feature may indicate which of two surgeons is controlling a particular manipulator arm.

Communication Using a Light Feature

In some examples, a visual aspect of a light feature such as an animation, pattern, brightness, or color may indicate information about a system, such as a status (e.g., joint or arm range of motion, system is ready for operation), or movement (e.g., to indicate that a portion of a system is moving or about to move or a direction of movement), or alert a user to a problem (e.g., a potential collision, a range of motion problem, or a fault condition).

In some examples, one or more light features on a column or other system link may simultaneously indicate both rotational orientation and vertical translation. For example, a display characteristic along the length of the light feature may display rotational information, and a display characteristic along the width of the ring displaying translational information. (See e.g., FIGS. 13B-13H, described above.)

In some examples, a ring (or other light feature) may be more than one color, and information may be indicated by color. For example, one or more rings (or other light features) may be different colors on different sides of an object (e.g., on a base, on an interface portion of an arm) or facing different directions. For example, the system shown in FIG. 9A may have a first color (e.g., green) at a portion of a light ring portion at a front of base, and blue light ring portion at side of base, and a red light portion at a rear portion of a base.

The colors may indicate a front portion (e.g., indicated by green) and a rear portion (e.g., indicated by red) of the base. In other examples, a color may indicate a direction of permitted movement, e.g., a first color (e.g., green) may indicate a permitted direction and a second color (e.g., red) may indicate a direction that is not permitted. In some examples, a first color may indicate a first direction is good (e.g., indicated by green) and a second direction is not good (e.g., indicated by red) or not desired or not pending or not needed.

A light feature may provide an instruction on direction of movement. For example, a color or pattern or animation may indicate to a user that a base or arm link or joint or other portion of a system should be moved in a direction indicated by the light pattern (e.g., move in direction of green light or not in direction of red light).

A light feature may indicate (e.g., provide an alert) pending or upcoming movement or a nature of a movement. For example, a color or flashing light may indicate that a movement of a joint is pending or may indicate a direction of pending movement. A light feature or combination of light features may indicate a combination of capability, nature, and pendency of movement of a joint, link, or arm component. In various examples, a light feature may indicate a joint is able to move, or a joint is actively moving, or that movement of a joint is pending, or translational motion or rotational motion of a link is pending, or combined rotational and translational motion is pending.

In some examples, a light feature may indicate a joint position or proximity to one or more joint range of motion limits. In some examples, a moving strip or other indication within a lighted ring may show joint position within a range of motion. For example, a light feature may change color near joint a range of motion limit (e.g., green or white may indicates not near a limit; yellow may indicate that a system is close to a range of motion limit; and red may indicate that a system is at a range of motion limit).

In some examples, a light feature may indicate a joint position relative to a target displacement or target position. For example, a light feature may display an indication of a target and a current displacement location (e.g., angular displacement location), and a user may be prompted to move the joint to align the current displacement location indicator with the target displacement location indicator (e.g., the user's goal may be to move the current displacement indicator to match the target indicator). In some examples, a light feature may provide an indication of how to move a joint to reach a target joint displacement. For example, a light feature may display an arrow indicating a direction of movement. As another example, a light feature may display a bar between a current position and a target position or displacement, and a user may be prompted to make the bar smaller by moving the joint toward the target orientation. In some examples, animated light patterns may move to indicate a direction of movement. A light feature may indicate proximity to a target. For example, the light feature may use a color scheme such as orange to mean farther from a target displacement, yellow to mean closer to the target, yellow-green to mean "almost at the target," and green to mean that a joint is at the target displacement. Other color schemes and light feature patterns are also possible, such as brightness (e.g., brighter means closer, dimmer means less close to target) or a flashing behavior (e.g., faster flash means closer, slower flash means further, steady light means the joint is at the target).

In some examples, a light feature may indicate a safe grab point on a device or system (e.g., green may indicate a safe grab point), or may indicate not to touch an arm (e.g., red indicates not to touch an arm or a portion of an arm).

In some examples, a system may use color coding to assist with identification or differentiation of units or links. For example, one modular system may have lights of a first color (e.g., blue lights), and a second system may have lights of a second color (e.g., yellow lights). Or, for a single modular system, an arm or other portion may have lights of a first color (e.g., blue), and a second arm or other portion may have lights of a second color (e.g., yellow).

In some examples, a light feature (e.g., steady red or flashing red) may indicate a location of an emergency handle or an instruction to pull an emergency handle or to initiate another emergency operation, or it may indicate the system performing an emergency action.

In various examples, a light feature may indicate a non-recoverable fault or a system power up or power down (e.g., an animation such as an apparently slowly moving light to indicate power up, or a slowly dimming light to indicate power down).

In some examples, a light feature may indicate a system operating mode, e.g., a following mode ("following" means an instrument motion follows a user control system input device movement), a control mode, a clutch mode (e.g., in which a joint brake is released to allow manual movement of a joint), a break-away clutch mode (e.g., in which a joint will resist movement from a force/torque on an associated link until a threshold force/torque is reached, at which point joint brake will release, further described below), a standby mode, a transport mode, or another system operating mode.

In various examples, a light feature may also be used to communicate a collision or near collision (e.g., a joint motion lock to avoid a collision) of a portion of a system (e.g., an arm) with another object (e.g., a surgical table or another arm). In some examples, a collision or near collision may be determined based at least on sensor information, such as information from a force sensor, an object or motion sensor (e.g., infrared sensor), or a proximity sensor (e.g., capacitive sensor). In some examples, a visual aspect (e.g., color) of a light feature may communicate that a portion of a system (e.g., an arm) is nearing (e.g., yellow) or at (e.g., red) end of joint or arm link range of motion.

In some examples, an aspect of one or more light features may indicate a state or status of the system, such as a ready state ("I am ready"), which may for example be indicated by a dim light feature, such as a dim blue appearance, or may be indicated by a "chasing" effect in which a light feature appears to move in an orbital motion (e.g., around a light ring) or oscillating motion. A light feature may also indicate a control state (e.g., a state in which the system is being controlled), such as manual control (which may for example be indicated by a steady bright appearance), or ready to be manually displaced (e.g., "clutched" brake release, which may be indicated for example by a pulsing or "breathing pattern"). A light feature may also indicate computerized control, such as a teleoperated control in accordance with a user's input (e.g., following movements of hand by a clinician), which may for example be indicated by a brightening of the light feature. A light feature may also indicate an automated joint displacement (e.g., carrying out automated commands), which may for example be indicated by a pulsing or "breathing" pattern. A light feature may also indicate a system self-test, during which a plurality (or all) of the light features in a system may communicate (e.g., pulse) the self-test, or a light feature at a specific part of the system may communicate (e.g., pulse) when that part of the system is under self-test. A light feature may indicate engagement by a user. For example, a light feature may activate or change (e.g., change color or brightness) when a user's hands are determined to be engaged with controls (e.g., based on detected contact, proximity, or presence). In some examples, a light feature may indicate that a system is unlocked (e.g., a setup mode has been completed) and the system is ready to operate. In some examples, a system may control a light feature to have a first response (e.g., no change, or change to a first color) when a user input is engaged while a system is locked, and the system may control the light feature to have a second response (e.g., change color or brightness) when user engagement is detected while the system is unlocked.

A light feature may change appearance (e.g., change color, such as blue to yellow) to indicate the location (e.g., at a joint or part) of a problem that needs to be addressed or corrected. In some examples, if an incorrect or unsafe action or state is detected, a light feature may change appearance, such as changing appearance in a manner calculated to get a user's attention. For example, the light feature may flash quickly or strobe or turn red.

A light feature may indicate a state of a particular part, joint, or connection. For example, a light feature may indicate that an accessory has been correctly attached to a system. A correct connection may be indicated by a light feature near the connection or on the accessory, or it may be indicated by other light features on the system. A correct connection may be indicated, for example, by a single pulse (short series of pulses), or a by a pulsing or "breathing" appearance, which may match a pulsing or breathing appearance of other aspects of the system, or may be present a different pulse appearance (e.g., faster or slower pulse rate).

In some examples, a light feature may indicate a joint state, such as whether a joint is locked or free to move (e.g., a clutch state of the joint). For example, a clutch state may be indicated by light feature color (e.g., green indicates free, red indicates locked) or pattern (e.g., pulsing or flashing indicates a free state in which manual movement is permitted, and steady indicates manual movement is not permitted).

In some examples, a light feature at a connection interface (e.g., a light ring around the interface) may indicate a connection state. For example, a light feature may be in one state (e.g., dim or off) when no connection is present and the light feature may be in a different state (e.g., bright) when a connection is present. In some examples, a light feature may briefly change appearance (e.g., pulse or flash) when a connection is made. The connection interface may be a mechanical connection (e.g., an interface that couples two things together, such as a manipulator and a controller), or the connection interface may be an electrical connection (e.g., a power connection or a communication connection). In some examples, a connection state, or change in connection state may be accompanied by an audio signal to reinforce the indication regarding the connection state.

A light feature may indicate the state of a flux through a connection, such as ready to deliver the flux through the connection, proper flux is passing through the connection, or insufficient flux is passing through the connection. For example, if a light feature is associated with an irrigation liquid or insufflation gas connection (e.g., a light ring around the connection), the light feature may indicate green when the connection is secure and the fluid is ready for delivery, may indicate a pulsing green when a proper fluid flux is passing through the connection, and may indicate a pulsing red when insufficient fluid flux is passing through the connection. Other flux examples include electrosurgical energy (mono- or bipolar energy), vacuum suction, respiration gasses, and the like used during surgery.

Any of the light feature appearances or behaviors described herein may be controlled by a medical device processor, which may receive one or more inputs from a user or another device, and may send one or more control signals to a light feature, or to a controller that may be configured to control a light feature, e.g., to control a voltage, current, or pattern delivered to a light feature. References to behavior of a light feature may be interpreted as a system behavior based on processing in the medical device processor or controller. A light feature may change color, for example, based upon delivery of current to a colored light emitting diode. For example, a light feature may change from red to blue by reducing power to a red LED and increasing power to a blue diode, or a light feature may be changed to purple by activating both diodes (to combine the colors). A light feature may be made to appear to move by sequentially activating and deactivating adjacent LEDs, which may create a "chasing," "running," or oscillating appearance.

Any of the light feature indications described herein may be accompanied by an audio indication, which may reinforce the light feature indication to the user, optionally by being synchronized to the corresponding light feature indication. The audio indication may include an aspect of a sound, such as pitch (e.g., frequency), volume or dynamic (e.g., amplitude), tone (e.g., fundamental or overtones), or a change or pattern in an aspect of sound. In various examples, an audio indication may include a rising, falling or pulsing volume (e.g., louder and softer), or a rising, falling, or pulsing tone change, or a rising, falling, or pulsing pitch (e.g., changing frequency). In some examples, an audio indication may match a light feature indication. For example, the timing of a change in a light feature may match the timing of an audio indication. Additionally or alternatively, a change in a quality of an audio indication may correspond to a change in a light feature. For example, an audio indication may become louder or rise in pitch or change tone as a light feature becomes brighter or changes color. In some examples, the volume, pitch, or tone may pulse in synch with a pulsing of a light feature. In some examples, a pitch of an audio indication may decrease as a joint (or object or part) moves toward a target displacement.

In addition, the features described with respect to controllable displays (e.g., OLED displays) may also be applied to light features or combined with light features (e.g., a light may indicate a status or status change and the status or status change may be indicated or explained on an OLED display, or a light feature may indicate that an option or feature is selectable on an OLED display.

Example Color/Pattern Schemes

A system may apply a scheme of colors and patterns to one or more light features to communicate the state of the system or to communicate a need for action. A color scheme may, for example, be applied to one or more light features in the system shown in FIG. 17-19, or 1B and 16, or 2A-2J, or other systems.

Colors and patterns may indicate system states. For example, when the system is in an off state, light features may be off and no pattern may be present (because the light features are off), which may indicate that the system is not powered or is disabled. When the system is in a "ready" state, a light feature may be a first color (e.g., blue) and the light feature may be dim, indicating that the system is ready for use. When the system is in a non-automatic movement state (e.g., clutched, as described herein), the light feature may be the first color and bright, which may indicate that a user controlled, non-automatic action is in progress (or available). For example, in a non-automatic movement state, a user may manually move a part of the system (e.g., an arm joint) with their hands, and the light feature may indicate the action in progress. When the system is in an automatic movement state, the light feature may be the first color, and the light feature may follow a pattern (e.g., the light feature may pulse), which may indicate that an automatic action is in progress (e.g., an arm joint is moving in response to a teleoperated control signal, or a computer-determined action is in process). When the system is in a confirmation state, the light feature may be the first color and may emit one or more pulses, which may indicate a confirmation. For example, to confirm a state or received command, a light feature may flash once to provide a visual confirmation signal to the user. When the system is in a "directional movement" state, the light feature may be the first color and follow a moving "chasing" pattern (e.g., portions of a light feature appear to move in a direction), which may indicate a directional movement, such as a pending motion or motion-in-progress, or a direction for a user to manually move a portion of the system (e.g., a joint). When the system is in a "potential action" state, the light feature may be a second color (e.g., yellow) and emit a steady "solid" pattern (e.g., not changing, such as consistently bright), or the light feature may follow a visual pattern that corresponds to another characteristic of the system (e.g., a ready state, or a non-automatic, automatic, or directional movement state). When the system is in an immediate action state, the light feature may be a third color (e.g., red), and the system may emit a solid pattern (or pulsing pattern), which may indicate that immediate action is required. While blue, yellow, and red have been provided as examples, other combinations are also possible, and specific states or groups of states may have other color assignments (e.g., green may indicate ready and movement states may be indicated by blue, or automatic movement may be indicated by purple). Other light feature pattern assignments may also be used.

Indication of Clutch States

In an example, the status of a break-away clutch feature may be communicated by a light feature, an integrated display, or one or more other features, alone or in combination. A system (e.g., system 200 or system 900 described above) may include a force sensor on a passive joint. The system may include a sensor on an active joint that senses an attempt to move. When a sensed parameter (e.g., force) crosses a threshold, the system releases a clutch, and the joint is permitted to move. When the joint stops moving, the system may re-apply the clutch (e.g., not permit the joint to move). The clutch release and re-engagement may be communicated through one or more light features. For example, from the user perspective, when the user pushes or presses or pulls hard enough on a structural feature (e.g., on an arm or joint), the joint breaks away from its commanded teleoperated position and permits manual movement, at which point a light feature may change (e.g., color or pattern or animation change) to indicate that state change (e.g., break-away clutch point has been reached). The system may then re-lock one or more joints when the user stops moving the structural feature (e.g., after a predefined period of non-movement or movement less than a threshold velocity), at which point the associated light feature pattern may change again. In another example, a system may exit or pause a following mode when a joint clutch is actuated (actively switched or break-away) to enter a clutch mode that permits manual (or assisted) movement, and then the system may return to the following mode automatically or in response to input after operating in clutch mode. These changes may be communicated via light features. Information on break-away clutching is found, e.g., in U.S. Pat. No. 9,452,020 B2 (filed Aug. 15, 2013) and in U.S. Patent Application Pub. No. US 2017/0172671 A1 (filed Mar. 17, 2015), both of which are incorporated herein by reference.

Light Feature Indications in Guided Processes

Light features may be used to facilitate a guided process for adjusting a manipulating system, such as the system 100 or 200 or 900. In an example, a light feature (e.g., light ring) at one or more specified joints (e.g., key joints) may light up when the joint is properly positioned or needs to be adjusted. For example, if a setup process needs an arm to be moved from a present angular orientation (e.g., a 90-degree orientation in which one arm link is perpendicular to a second arm link) to a second angular orientation (e.g., a 45-degree orientation), the light feature at the associated joint may be controlled to present a specified appearance (e.g., bright, or change color, or pulse) to identify the joint to be moved. The light feature may additionally or alternatively be controlled to indicate when a target joint displacement has been achieved (e.g., by presenting a specified color, such as green or blue). In some examples, light features at specified joints (e.g., key joints) may change color when the joints are positioned correctly.

In some examples, a light feature pattern may indicate a direction of movement. For example, a light feature may include a plurality of discrete light elements that form the light feature pattern, and the elements may sequentially light up so that the light portions appear to move along the light feature (e.g., the lights may appear to "run" or "chase" around a ring to indicate rotational movement). In various examples, a light feature may indicate a direction that a part of a device (e.g., an arm link) should be manually moved, or a light feature may indicate a direction that the part will move automatically when activated, or a light feature may indicate a direction that a part is moving (e.g., in response to a teleoperated control input), which provides supporting visual feedback to a user that the user is rotating or translating a joint in a correct direction.

In some examples, a light feature may communicate a target displacement, a range of motion limit, or a proximity to a range of motion limit. For example, a light feature may include a visually different location feature (e.g., a visual "hot spot" or bright spot), and a device may have an indicator proximate the light feature. The device may be configured so that the target or range of motion limit is reached when the location feature aligns with the indicator. The indicator may be a physical feature (e.g., a mark) on a device, or it may be a location feature on a light feature.

Example location features are illustrated in FIGS. 20A-B. FIGS. 20A-20B show a light feature 2012, which may be at a joint 2016 on the device 2000. The joint 2016 may allow the second arm portion 2014 of the device 2000 to rotate with respect to the first portion 2002. The light feature 2012 may have a location feature 2020, which may be a visual hot spot or other visually different feature, and which may represent a target location or a range of motion limit. The second arm portion 2014 of the device 2000 may include an indicator 2022. When the second arm portion 2014 of the device 2000 is rotated upward with respect to the first portion 2002 (or the first portion 2002 is rotated downward with respect to the second arm portion 2014), the indicator 2022 moves toward the location feature 2020 and eventually aligns with the location feature 2020 when the range of motion limit is reached, as shown in FIG. 20B.

In another example, an adjacent light feature 2010 may include a second location feature 2024 (e.g., hot spot), and the target displacement may be reached when the second location feature 2024 aligns with the first location feature 2020. The second location feature 2024 or first location feature 2020 or both may change appearance (e.g., change color) when the second location feature 2024 aligns with the first location feature 2020. In some examples, the second location feature 2024 may be considered aligned with the first location feature 2020 when the second location feature 2024 is within a specified displacement (e.g., a specified distance (e.g., 2 mm) or angular rotation (e.g., 2 degrees) or percentage (e.g., 1 percent of range of motion) of the first location feature 2020.

In another example, a light feature 2006 may include a third location feature 2026 and a fourth location feature 2028, which may represent a target displacement location or target displacement range, and alignment of the third location feature 2026 with the fourth location feature 2028 may indicate that a target location has been achieved, as shown in FIG. 20B. As the third location feature 2026 and fourth location feature 2028 merge or overlap, the third location feature 2026, fourth location feature 2028, or both, or an overlapping region, may change appearance, such as by changing color, or brightening, or changing pulse state (e.g., change from steady to pulsing). In another example, the fourth location feature 2028 may indicate a desired displacement or range of displacements, which may, for example, correspond to a specified location (e.g., center) between available range of motion limits. The range of motion limits may be mechanical limits for the joint, or they may be based upon other constraints such as proximity to other arms or a patient clearance requirement.

Any of the visual location feature examples described above may provide guidance for a user to move a device or device component, such as an arm or arm link (e.g., in system 100, 200, or 900), to a target position or range. A system may include a plurality of light features that each include one or more location features, so that a user may be guided through movement of multiple joints in the system. In some examples, the order of a sequence of movements at a plurality of joints may be indicated by an appearance (e.g., pulsing or color change or brightness change) of a light feature or location feature portion of a light feature. A first light feature pattern associated with a first joint to be moved is first activated until the first joint is in a proper displacement, at which time a second light feature pattern associated with a second joint to be moved is activated until the second joint is in a proper displacement, and so on. In some examples, responsive to a change in pose or configuration, the light feature patterns may be updated. For example, the position of a location feature that indicates a joint target location or range may be change to indicate a new target location or target range. Updating the position of one or more location features may provide guidance to a user regarding how to move an arm (or other device) to achieve a target position or range and may be dynamic based on the state of one or more other system components, such as another arm joint that is moved. Dynamic updating of light feature patterns allows visual guidance to be iterative, so that if a first light feature directs a first joint motion, and a second joint feature directs a second joint motion, the first light feature pattern may be updated to direct the user to adjust the first joint again based on the second joint's movement.

In another example, a light feature 2030 may include a fifth location feature 2032 and a sixth location feature 2034, which may indicate a joint or arm range of motion limit. The fifth location feature 2032 may abut the sixth location feature 2034 when the range of motion limit is reached, as shown in FIG. 20B. In some examples, the fifth location feature 2032, sixth location feature 2034, or both may change appearance when the sixth location feature 2034 approaches the fifth location feature 2032 (e.g., change color to yellow) or reaches the fifth location feature 2032 (e.g., reaches the end of range of motion, which may be indicated for example by a change to red, or flashing, or both). In some examples, an entire light feature pattern (or any portion thereof) may change appearance in addition or in alternative to one or both of the location features 2032, 2034 changing appearance.

Any of the light feature location techniques shown in FIGS. 20A-20B or explained above may be used individually or in any combination. While FIGS. 20A-B show a rotational example, the techniques for indicating range of motion limit or target displacement location may also be applied to different types of motion, such as angular motion (e.g., the articulation of an arm joint in system 100 or system 900) or translational motion (e.g., when a first part slides relative to a second part to align a light feature with an indicator on a device or to align with another light feature, the alignment may indicate a range of motion limit, or achievement of a target position).

Light Features on a User Control Unit

A user control unit may include one or more light features, which may indicate information about the control unit or an associated system, such as a user interaction with the user control unit, or a system state (e.g., lock state).

FIG. 17 is an illustration of a user control unit 1700, which may include a display portion 1720 and a user input portion 1730. The user control unit 1700 may, for example, be used to control a manipulator, such as the manipulator 1800 shown in FIGS. 18 and 19. The user control unit 1700 and manipulator 1800 may include some or all of the components of the system 1200 illustrated in FIG. 12 and described above. The user control unit 1700 may include one or more light features 1702, 1706, which may change appearance (e.g., change color or brightness or flash or pulse) in response to a system state or user interaction with the control unit 1700. For example, one or more light features 1702, 1706 may change appearance responsive to a user touch against a face 1740 of the control unit 1700 or other portion (e.g., side 1742, or front 1744) of the control unit 1700, or against a user input 1704, 1706. An appearance of a light feature 1702, 1706 change may indicate a lock state or control state of the system, such as whether the manipulator 1800 is being controlled by the control unit 1700.

As shown in FIG. 17, the user control unit 1700 may include a first user input 1704, which may, for example, be a scroll wheel. In some examples, the scroll wheel may control insertion and withdrawal of an instrument, such as a medical catheter. As shown, a first light feature 1702 is at the first user input 1704. The light feature 1702 may include an LED, which may be on a top surface 1740 of the control unit 1700, or the top surface 1740 may include a plurality of holes and the LED panel may be beneath the top surface 1740 under the holes (e.g., as described above in reference to FIG. 3A). The light feature 1702 may extend around the first user input 1704 (e.g., scroll wheel). For example, the light feature 1702 may extend part way around the first user input 1704 or all of the way around the first user input 1704. The light feature 1702 may be configured as a light ring. In some examples, the light feature 1702 may indicate a control state. For example, the light feature 1702 may become bright when the first user input 1704 is controlling or ready to control a device such as the manipulator 1800 or an attached instrument. In an example, the user control unit 1700 may detect user contact, presence, or proximity (e.g., of a hand), and the light feature 1702 may change appearance (e.g., change from dim to bright) when user contact, presence, or proximity is detected.

The user control unit 1700 may also include a user input 1708, which may for example be a track ball. In some examples, the user control unit 1700 and manipulator 1800 may be configured so that the track ball controls directional movement (e.g., left, right, up, or down steering) of the manipulator. For example, rolling the track ball to the left may steer a distal end of a steerable instrument mounted to the manipulator to the left, rolling the track ball to the right may steer the distal end of the instrument to the right, rolling the track ball forward may steer the distal end down, and rolling back may steer the instrument upward. A second light feature 1706 may be at second user input 1708, and second light feature 1706 may be configured similarly to first light feature 1702.

In some examples, one or more light features (e.g., 1702, 1706) may present a changed appearance in response to detection of a user input or of user contact, presence, or proximity. For example, one or more other light features on the user control unit, on a manipulating system controlled by the user control system unit as described below, or both, may change appearance to match the appearance of light feature 1702 when light feature 1702 changes in response to detected user input or user contact, presence, or proximity. As a more specific example, light features 1702 and 1706 may be rings that are dimly lit blue to indicate the surgical system is ready for use, and when a clinical user's hand comes near or touches first user input 1704, light features 1702 and 1706 change to a brightly lit blue to indicate the system is now under user control. In addition, one or more similar light features on corresponding manipulator 1800 optionally may change from a dimly lit to a brightly lit blue light ring to indicate to a clinician (e.g., a second clinician remote from the user control system) dear the manipulating system that it is under user control. And, when the first clinician at the user control unit moves the hand away from a user input, the light features change from the brightly lit blue to the dimly lit blue.

The light features may indicate other system states and events with various light feature patterns as described herein. The user control system 150 may also include other light features and light feature patterns, including controllable display features, as described herein.

Example Light Feature on a Manipulator System

Figure 18:
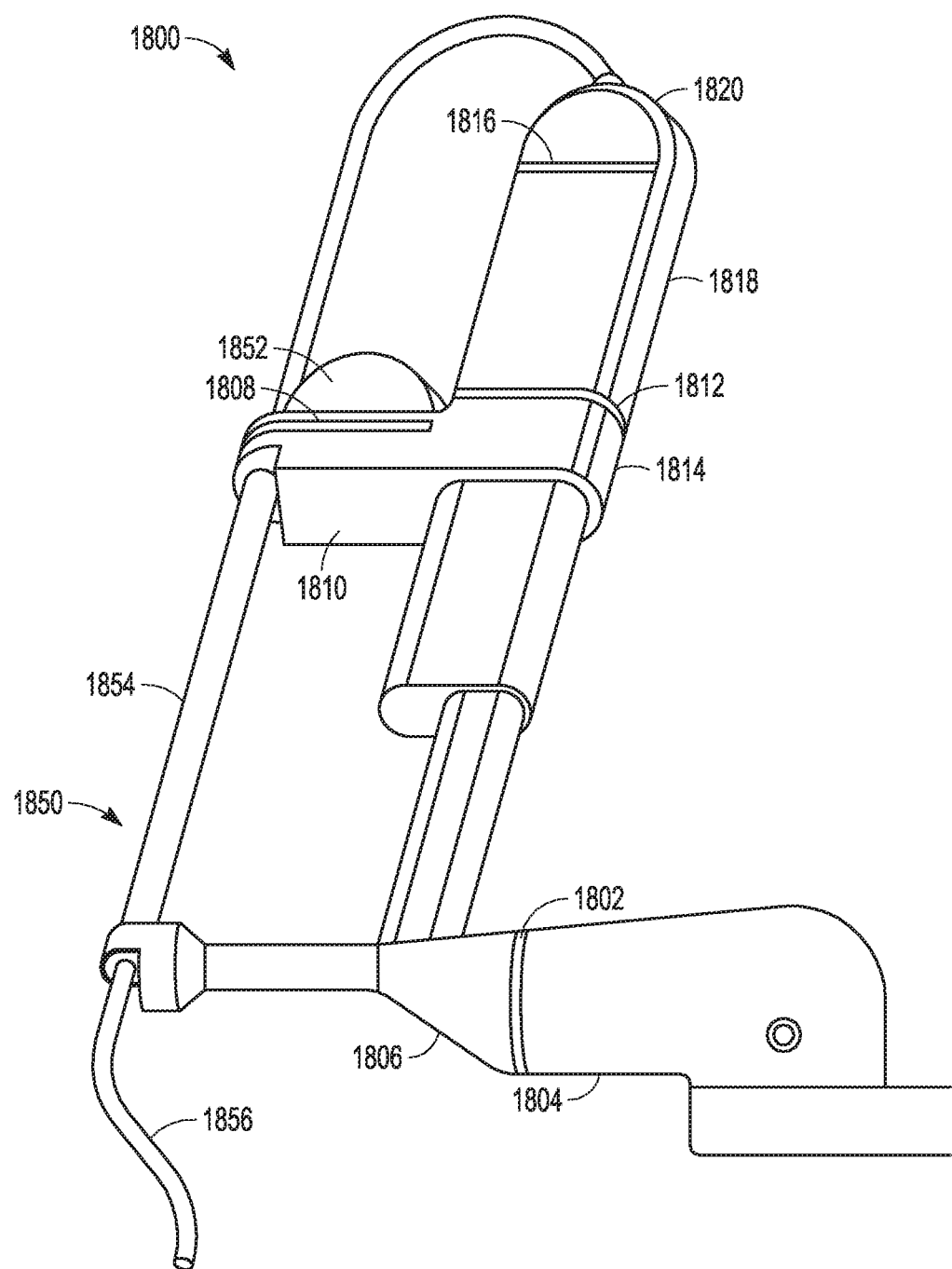
FIG. 18 is an illustration of a manipulator with light features.

FIG. 18 is an illustration of another example manipulator 1800 with light features. An instrument 1850 is shown mounted on the manipulator 1800. The instrument 1850 may include a proximal mounting portion 1852, an instrument shaft 1854 extending distally from the mounting portion 1852, and an instrument steerable distal working portion 1856 coupled to the distal end of instrument shaft 1854.

The manipulator 1800 may include a first light feature 1802 at a lower rotational joint between an arm link 1804 and a forearm link 1806 of the manipulator 1800. The forearm link 1806 may rotate relative to the arm link 1804 at a joint, and the light feature 1802 may be located at the joint. As shown, the long axes of links 1804, 1806 are coaxial and define the axis of rotation of link 1806 with reference to link 1804. First light feature 1802 may function as described herein.

The manipulator 1800 may include a second light feature 1808 at an interface where the instrument 1850 may be mounted to an instrument carriage portion 1810 of the manipulator 1800. The second light feature 1808 may, for example, indicate a connectivity state of the interface (e.g., instrument physically mounted, energy or communication between instrument and carriage is functioning, etc.) or a control state of the instrument 1850 or manipulator 1800. The manipulator 1850 may additionally or alternatively include a third light feature 1812 on a fixed or telescoping spar 1814 of the manipulator 1800, and the third light feature 1812 may function as described herein. The manipulator 1800 may include a fourth light feature 1816 at a top portion 1818 of the spar 1814, where an instrument adaptor 1820 may be connected.

As described herein, first, second, third, and fourth light features 1802, 1808, 1812, and 1816 may function individually or in any combination to indicate operating conditions or events at a corresponding location on manipulator 1800, or for manipulator 1800 in general, or for the teleoperated surgical system in general (e.g., including a corresponding control system unit, and optionally one or more auxiliary support systems).

Figure 19:
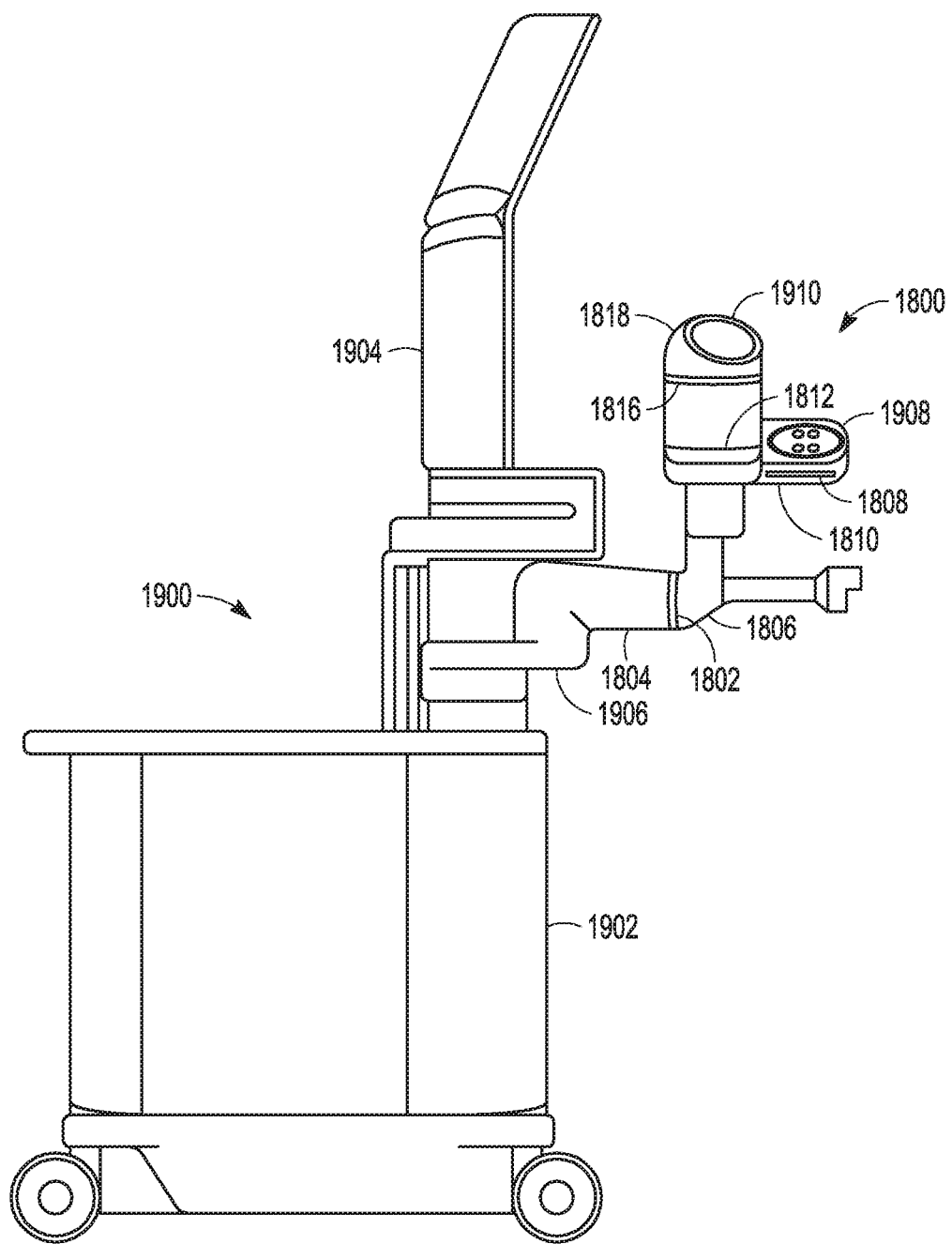
FIG. 19 is an illustration of a manipulator on a movable manipulator unit.

FIG. 19 is an illustration of the manipulator 1800 on a movable manipulator system unit 1900. The manipulator system unit 1900 may include a base 1902, a display system 1904 that may for example be configured to output information similar to a display on a corresponding user control system unit, and the manipulator 1800. The manipulator 1800 is shown in FIG. 19 with no instrument mounted, and so a first interface portion 1908 and second interface portion 1910 are visible. As described above, an instrument may be mounted to the manipulator 1800 at the first interface portion 1908 and second interface portion 1910, and a light feature 1808 may be at (e.g., extend around) the first interface portion 1908, a light feature 1816 may be at the second interface portion 1910, or both. The manipulator system unit 1900 may also include light features at other locations as described above or elsewhere herein (e.g., as shown in FIG. 9A), such as at the bottom of the base (e.g., near the floor) or where the display system 1904 or the manipulator arm 1906 meet the base.

Figure 21:
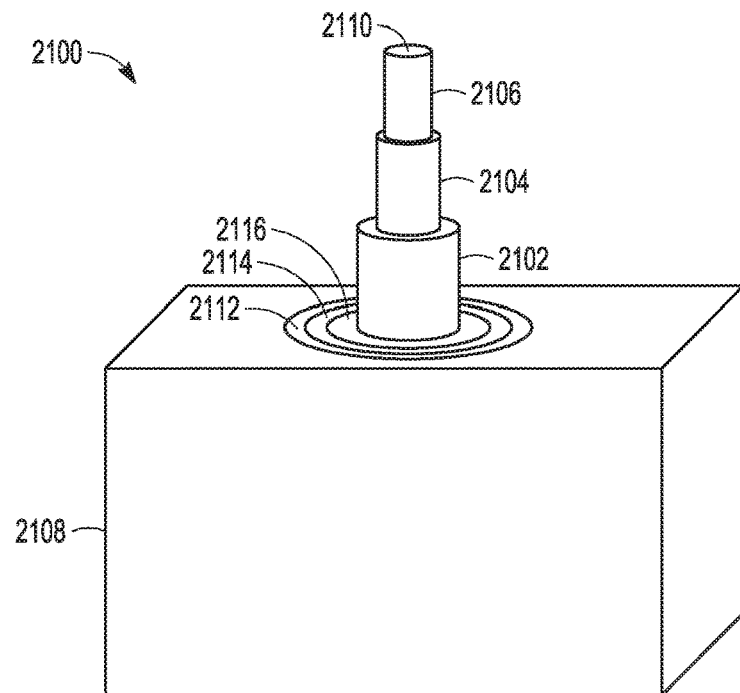
FIG. 21 is an illustration of a medical device that has light features around a telescoping column.

FIG. 21 is an illustration of a medical device 2100 that has a telescoping column 2110 extending from a base 2108, which may for example be a base of a manipulating system as shown in FIGS. 2A-2B, FIG. 9A, or FIG. 19. The telescoping column 2110 may have one, two, three, four, or more telescoping parts. As shown as an illustration, the telescoping column 2110 may have a first part 2102, a second part 2104 that extends from the first part 2102, and a third part 2106 that telescopes from the second part 2104. An arm, spar, or other device may be mounted to the distal third part 2106. The device 2100 may have a plurality of light features (e.g., light rings), which may correspond to the first part 2102, second part 2104, and third part 2106. For example, an outer ring 2112 may correspond to the first part 2102, a middle ring 2114 may correspond to the second part 2104, and an inner ring 2116 may correspond to the third part 2106. As shown, the rings are concentric around the column 2110, and the correlation between the relative size and position of the rings and the telescoping parts of the column 2110 may assist a user with understanding the relationship between the rings and telescoping parts. The rings may communicate information about the telescoping parts, such as rotational or translational range of motion (e.g., red indicates end of range of motion), target joint orientations, target telescoping link part translations, etc., as described herein. While three rings and corresponding telescoping parts are shown, more (e.g., 4, 5, or more) or fewer (e.g., 2) pairs of rings and corresponding parts could also be used.

Figure 22:
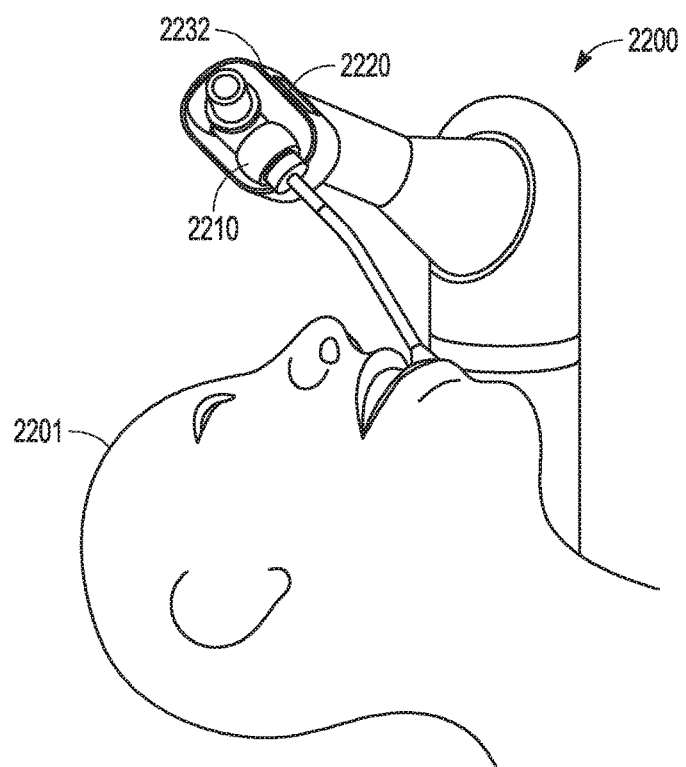
FIG. 22 is an illustration of a medical device system that includes a light feature at a swivel connector.

FIG. 22 is an illustration of an example light feature 2220 at a swivel connector 2210, which may couple to an endotracheal tube that extends into a patient 2201. The light feature 2220 may extend along a side 2232 of a mount portion of a manipulating system 2200 near the swivel connector 2210. In some examples, the light feature 2220 may extend around the mount portion to form a light ring. The mount portion may hold, for example, a guiding part for a flexible instrument catheter, an instrument cannula, or as shown an endotracheal tube swivel connector. The light appearance of the light feature 2220 (e.g., color or other light feature pattern) may indicate, for example, whether the swivel connector 2210 is in alignment (e.g., green or steady light) or out of alignment (e.g., red or pulsing may indicate out of alignment). And so in this example, a light feature is used to indicate the state of an interface connection. Further, the light feature optionally may be used to indicate the status of respiratory air flow through the swivel connector 2210 as an example of a flux through an interface.

Figure 23A:
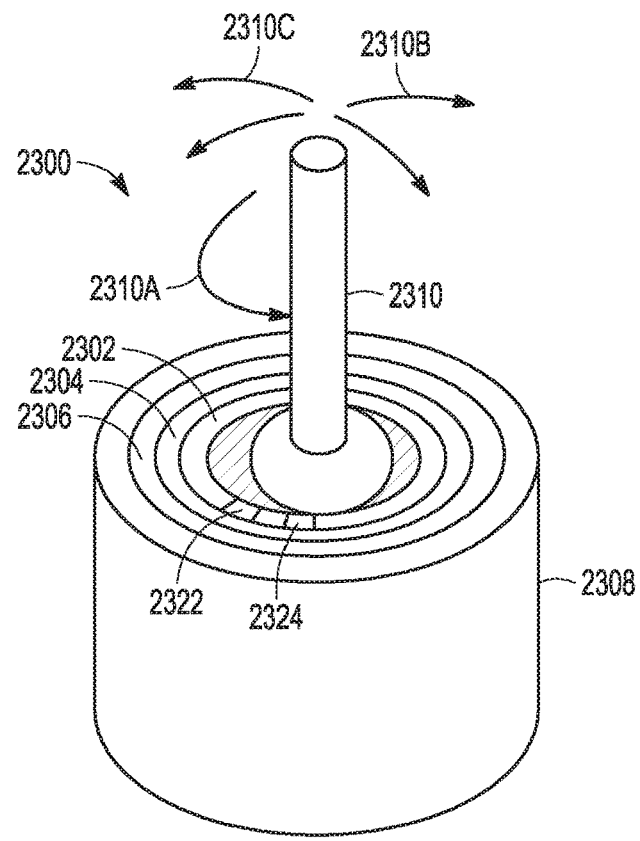
FIGS. 23A-23B are illustrations of a medical device that has light features around a joint with multiple degrees of freedom.
Figure 23B:
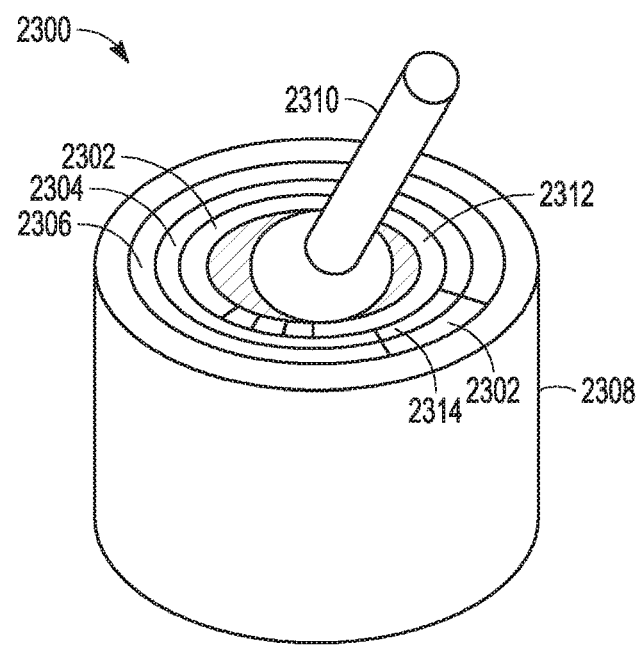

FIGS. 23A and 23B are illustrations of a medical device 2300 that has a plurality of light features 2302, 2304, 2306 around a joint that has multiple degrees of freedom. The medical device 2300 may have a first part 2308, which may for example be a portion of an arm, or a base, of the manipulating system 100, 900, or 1800. The first part 2308 may be coupled to a second part 2310 using a joint, such as a spherical joint, that has multiple degrees of freedom. For example, the joint may rotate in two or more orientation axes, as indicated by arrows in the figure. That is, second part 2310 may roll as indicated by arrow 2310a, pitch as indicated by arrow 2310b, and yaw as indicated by arrow 2310c. The light features 2302, 2304, 2306 surround the joint, and optionally may be concentric with each other. In some examples, a first light feature 2302 may correspond to roll motion. The first light feature 2302 may indicate, for example, direction of roll motion (e.g., an orientation direction a user should move part 2310, or a direction that a joint is moving, or a direction the joint is about to move). The light feature 2302 may include one or more location features 2322, 2324 (e.g., as described above), which may indicate a current orientation, indicated by location feature 2322, relative to a range of motion limit, indicated by location feature 2324. Responsive to roll (e.g., counter-clockwise) of the second part 2310 relative to the first part 2308, the location feature 2322 may move (counter-clockwise) toward the range of motion limit indicated by location feature 2324.

Light feature 2304 may correspond to rotational pitch and/or yaw motion, either alone or in combination with yaw. For example, responsive to yawing the second part 2310 from the orientation shown in FIG. 23A to the orientation shown in FIG. 23B, the light feature 2304 may change appearance (e.g., may change from green to yellow to indicate the approach of a range of motion limit). In some examples, a location feature 2314 on the light feature 2304 may change appearance. For example, the location feature 2314 may change to yellow, but the rest of the light feature 2304 may stay green.

In some examples, the light features 2304 and 2306 may both correspond to rotational motion. For example, the location feature 2314 may correspond to a first angular orientation (e.g., a present orientation), and a location feature 2316 on light feature 2306 may indicate the desirability or proximity to range of motion if the part 2310 is further rotated in a direction aligned with light the feature 2306.

While the light features 2302, 2304, 2306 are shown and described as discrete light features (e.g., separate rings), they also may be different portions of the same light feature. Further, it can be seen that one or more similar light feature displays can be adapted for use with translational motion of second part 2310 with reference to first part 2308, showing second part 2310's position in one, two, or three Cartesian DOFs in order to indicate translational information analogous to the rotational information described herein. And, it can be seen that one or more similar light features can be adapted for use with any combination of one, two, or three Cartesian orientations and one, two, or three Cartesian positions.

Figure 24:
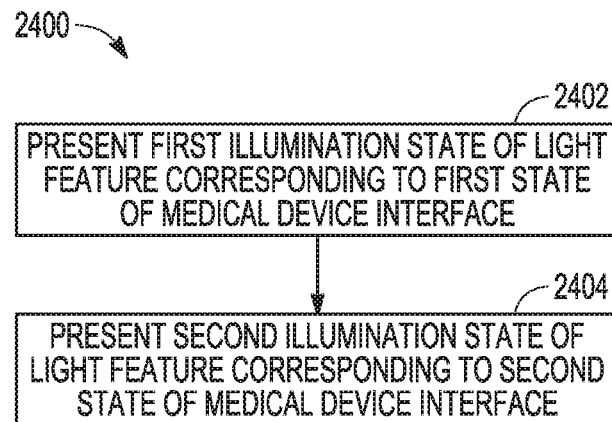
FIG. 24 is a flowchart illustration of a method of controlling a medical device having an interface.

FIG. 24 is a flowchart illustration of a method 2400 of controlling a medical device having an interface. The method 2400 may include, at 2402 presenting a first illumination state of the light feature corresponding to a first state of the interface. The method 2400 may include, at 2402, presenting a second illumination state of the light feature corresponding to a second state of the interface. In some examples, the first illumination state corresponds to a first joint displacement value and the second illumination state corresponds to a second joint displacement value. In some examples, the first illumination state corresponds to a first joint angle and the second illumination state corresponds to a second joint angle. In some examples, presenting the first illumination state includes presenting a first animated state in which an apparent movement of the light feature corresponds to a first movement at the interface, and presenting a second illumination state includes presenting a second animated state in which an apparent movement of the light feature corresponds to a second movement at the interface.

Figure 25:
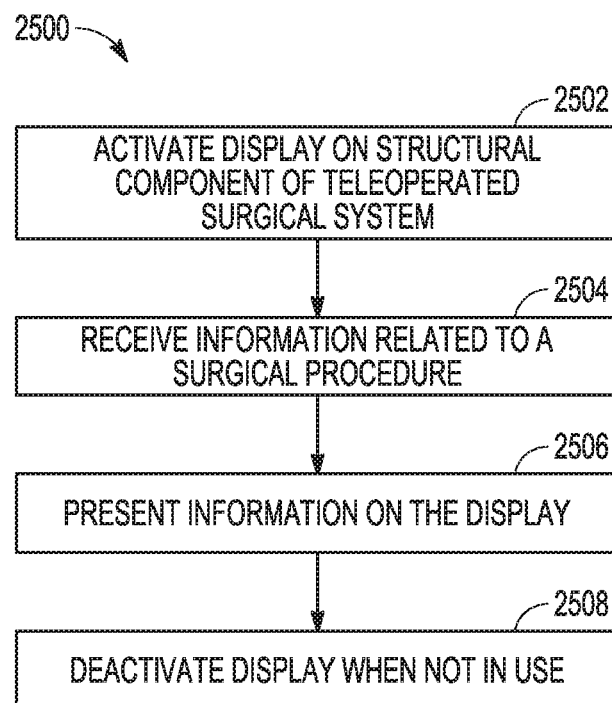
FIG. 25 is a flowchart illustration of a method of controlling an integrated display on a teleoperated surgical system.

FIG. 25 is a flowchart illustration of a method 2500 of controlling an integrated display on a teleoperated surgical system. The method 2500 may include, at 2502, activating a display on a structural component of the teleoperated surgical system to present information on the structural component. Activating the display may include, for example, activating a lighted display behind an array of micro-holes in the structural component.

The method 2500 may include, at 2504, receiving information related to a surgical procedure. Receiving information may include receiving information from a clinician's console and presenting information includes presenting a message or instruction on the integrated display.

The method 2500 may include, at 2506, presenting information on the integrated display based on the received information. In an example, the integrated display is on a first manipulator arm and presenting information includes presenting a first identifier for the first manipulator arm. The method may also include presenting a second identifier on a second manipulator arm, wherein the first manipulator arm is differentiable from the second manipulator arm based on the presentation of first identifier and the second identifier.

In some examples, the received information may include, for example, a present pose of a manipulator arm and the presented information includes an operating mode or status associated with the present pose.

In some examples receiving information may include receiving an elapsed time or a time to completion, and presenting information on the integrated display may include presenting the elapsed time or the time to completion.

In some examples, receiving information may include receiving an instrument type that is coupled to a manipulator arm and presenting information includes presenting the instrument type.

In various examples, the method may include indicating a safe grab point on an arm, indicating to interact with to manipulate an arm, presenting guided setup instructions on the integrated display, identifying an arm to service or adjust, indicating an instrument change to be performed on an identified manipulator arm, or communicating a range of motion status.

The method 2500 may include, at 2508, deactivating the display when the display is not in use, wherein the display is not visually detectable when the display is deactivated.

Figure 26:
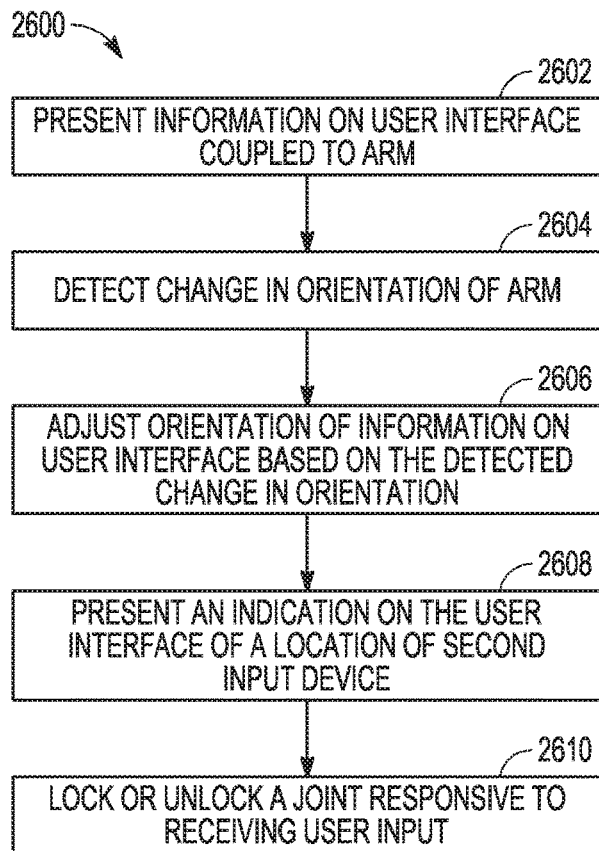
FIG. 26 is a flowchart illustration of a method of presenting information on a display on a teleoperated surgical system.

FIG. 26 is a flowchart illustration of a method 2600 of interacting with a user via a user interface on a teleoperated surgical system. The method 2600 may include, at 2602, presenting information on a first user interface coupled to an arm of the teleoperated surgical system. The method 2600 may include, at 2604, detecting a change in orientation of the arm. Detecting a change in orientation of the arm may include, for example, receiving information from an orientation sensor. The method 2600 may include, at 2606, adjusting an orientation of the information presented on the user interface based on the detected change in orientation of the arm.

The method 2600 may include, at 2608, presenting an indication on the user interface of a location of second input device. The method may also include receiving user input through the second input device.

The method 2600 may include, at 2610, locking or unlocking a joint responsive to receiving user input (e.g., responsive to receiving user input through the second input device.)

Figure 27:
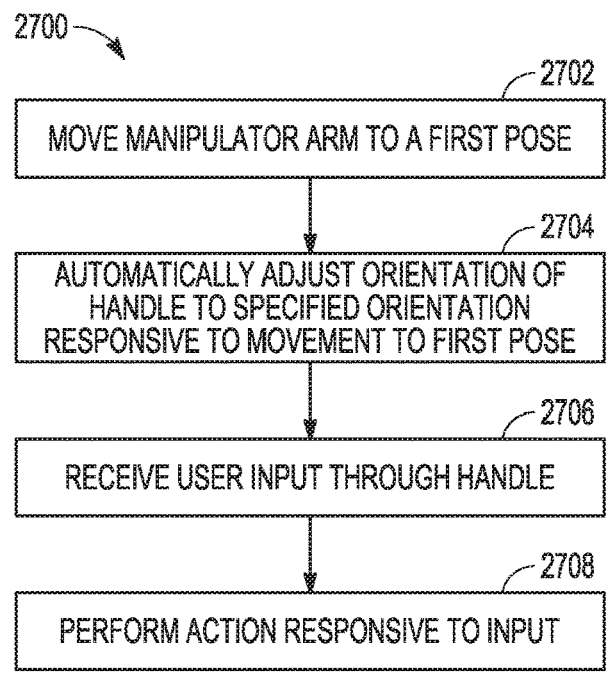
FIG. 27 is a flowchart illustration of a method of controlling a configuration of a manipulator arm and a handle of a teleoperated surgical system.

FIG. 27 is a flowchart illustration of a method 2700 of controlling a configuration of a manipulator arm and a handle of a teleoperated surgical system. The method may include, at 2702 moving a manipulator arm to a first pose.

The method 2700 may include, at 2704 automatically adjusting an orientation of a handle to a specified orientation responsive to movement of the manipulator arm to the first pose. Adjusting the orientation of the handle includes positioning the handle in a consistent orientation through a range of positions of the manipulator arm. The method may include, for example, positioning the handle in a horizontal orientation.

In some examples, the method may include determining a handle orientation based on a frame of reference. The frame of reference may include one or more user parameters. For example, the one or more user parameters includes a user height, and the method may include positioning the handle at an orientation based at least in part on the user height.

The method 2700 may include, at 2706, receiving a user input. In some examples, a specified orientation of the handle may be determined based at least in part on the user input.

In some examples, the method 2700 may include, at 2708, performing an action responsive to the input. For example, the method 2700 may include performing an egress procedure responsive to a user input and adjusting the orientation of the handle to an egress orientation as part of the egress procedure. In some examples, the method 2700 may include releasing the handle responsive to the user input, wherein the orientation of the handle is manually adjustable when the handle is released. In some examples, the method may include receiving a first user input indicating a first handle orientation when the arm is a first pose, and receiving a second user input indicating a second handle orientation when the arm is in a second pose, wherein a specified third orientation of the handle for a third pose of the arm is determined based at least in part on the first user input and the second user input.

Although aspects are in some instances described in the context of a modular, single-arm units of a manipulating system as part of a computer-assisted teleoperated surgical system, in other embodiments these aspects may be incorporated into one or more arms that are mounted on a surgical table (table base or side-rail), or on another object in the operating room, or are mounted on the floor or the ceiling or a wall of the operating room. In some examples, two or more arms with these aspects may be mounted on a manipulating system, or on another object in the operating room, or at a single location on a table, object, floor, ceiling, or wall in the operating room.

In addition, two single-arm manipulating systems located together are disclosed as examples, but disclosed aspects apply to more than two single-arm manipulating systems, such as three, four, or five single-arm manipulating systems, or to a combination of any number of single-arm manipulating systems and one or more multi-arm manipulating systems, such as a da Vinci® surgical system, commercialized by Intuitive Surgical, Sunnyvale, Calif.

Persons of skill in the art will understand that any of the features described above may be combined with any of the other example features, as long as the features are not mutually exclusive. All possible combinations of features are contemplated, depending on clinical or other design requirements. In addition, if manipulating system units are combined into a single system (e.g., telesurgery system), each individual unit may have the same configuration of features, or, one manipulating system may have one configuration of features and another manipulating system may have a second, different configuration of features. As stated above, an exhaustive list of all possible combinations of aspects and features would result in a prolix description, and it should be clear to skilled persons that various combinations of the aspects and features described herein are contemplated.

The examples (e.g., methods, systems, or devices) described herein may be applicable to surgical procedures, non-surgical medical procedures, diagnostic procedures, cosmetic procedures, and non-medical procedures or applications. The examples may also be applicable for training or for obtaining information, such as imaging procedures. The examples may be applicable to handling of tissue that has been removed from human or animal anatomies and will not be returned to a human or animal, or for use with human or animal cadavers. The examples may be used for industrial applications, general robotic uses, manipulation of non-tissue work pieces, as part of an artificial intelligence system, or in a transportation system.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A medical device configured for use with a teleoperated surgical system, the medical device comprising:
   a control system;
   a movable robotic manipulator arm; and
   a handle coupled to the robotic manipulator arm;
   wherein the handle is configured to be oriented at a first hold angle relative to the robotic manipulator arm on condition that the robotic manipulator arm is in a first pose;
   wherein the control system comprises programmed instructions to automatically orient the handle at a second hold angle toward a user on condition the control system positions the robotic manipulator arm in a second pose different from the first pose; and
   wherein in the second pose, the handle is in a different orientation relative to the robotic manipulator arm than in the first pose.

2. The medical device of claim 1, wherein an orientation of the handle is adjusted to present the handle at the second hold angle based upon a user profile.

3. The medical device of claim 2, wherein an orientation of the handle is user-adjustable.

4. The medical device of claim 2, wherein the control system comprises programmed instructions to move the handle relative to the robotic manipulator arm to maintain the handle at a specified orientation as the robotic manipulator arm moves between poses.

5. The medical device of claim 2, further comprising an orientation sensor, wherein control system comprises programmed instructions to receive information from the orientation sensor and adjust an orientation of the handle based on the information received from the orientation sensor.

6. The medical device of claim 2, wherein the medical device includes a user interface on the handle.

7. The medical device of claim 2, wherein the user profile includes a user height.

8. The medical device of claim 7, wherein an orientation of the handle is user-adjustable.

9. The medical device of claim 7, wherein the control system comprises programmed instructions to move the handle relative to the robotic manipulator arm to maintain the handle at a specified orientation as the robotic manipulator arm moves between poses.

10. The medical device of claim 7, further comprising an orientation sensor, wherein the control system comprises programmed instructions to receive information from the orientation sensor and adjust an orientation of the handle based on the information received from the orientation sensor.

11. The medical device of claim 7, wherein the medical device includes a user interface on the handle.

12. The medical device of claim 1, wherein an orientation of the handle is user-adjustable.

13. The medical device of claim 12, wherein the control system comprises programmed instructions to move the handle relative to the robotic manipulator arm to maintain the handle at a specified orientation as the robotic manipulator arm moves between poses.

14. The medical device of claim 1, wherein the control system comprises programmed instructions to move the handle relative to the robotic manipulator arm to maintain the handle at a specified orientation as the robotic manipulator arm moves between poses.

15. The medical device of claim 14, wherein the specified orientation is an angle or range of angles.

16. The medical device of claim 14, wherein the specified orientation is determined with respect to a specified frame of reference.

17. The medical device of claim 1, further comprising an orientation sensor, wherein the control system comprises programmed instructions to receive information from the orientation sensor and adjust an orientation of the handle based on the information received from the orientation sensor.

18. The medical device of claim 1, wherein the medical device includes a user interface on the handle.

19. The medical device of claim 18, wherein the control system comprises programmed instructions to, responsive to input via the user interface, release the handle to enable manual adjustment of an orientation of the handle.

20. The medical device of claim 18, wherein the robotic manipulator arm is controllable via the user interface.

21. The medical device of claim 18, wherein the medical device is configured to perform an auto-egress operation responsive to an input via the user interface.

22. A medical device configured for use with a teleoperated surgical system, the medical device comprising:
a control system;
a movable robotic manipulator arm; and
a handle coupled to the robotic manipulator arm;
wherein the control system comprises programmed instructions to automatically orient the handle in a first hold angle relative to the robotic manipulator arm on condition that the robotic manipulator arm is in a first pose;
wherein the control system comprises programmed instructions to automatically orient the handle in a second hold angle relative to the robotic manipulator arm on condition that the robotic manipulator arm is in a second pose different from the first pose; and
wherein in the second pose, the handle is in a different orientation relative to the robotic manipulator arm than in the first pose.

* * * * *

UNITED STATES PATENT AND TRADEMARK OFFICE
CERTIFICATE OF CORRECTION

PATENT NO. : 11,751,966 B2
APPLICATION NO. : 16/634489
DATED : September 12, 2023
INVENTOR(S) : Timothy B. Hulford et al.

It is certified that error appears in the above-identified patent and that said Letters Patent is hereby corrected as shown below:

In the Claims

Column 74, Claim 5, Line 50, after wherein, insert --the--.

Signed and Sealed this
Twenty-sixth Day of December, 2023

*Katherine Kelly Vidal*

Katherine Kelly Vidal
*Director of the United States Patent and Trademark Office*